(12) United States Patent  (10) Patent No.: US 7,728,005 B2
Okuzumi et al.  (45) Date of Patent: Jun. 1, 2010

(54) ETHER DERIVATIVE

(75) Inventors: Tatsuya Okuzumi, Kawasaki (JP); Tamotsu Suzuki, Kawasaki (JP); Youji Yamada, Kawasaki (JP); Shinichi Fujita, Kawasaki (JP); Yoichiro Shima, Kawasaki (JP); Yoriko Yamamoto, Kawasaki (JP); Tetsuo Yano, Kawasaki (JP); Tadakiyo Nakagawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1064 days.

(21) Appl. No.: 11/402,958

(22) Filed: Apr. 13, 2006

(65) Prior Publication Data

US 2006/0270693 A1   Nov. 30, 2006

Related U.S. Application Data

(63) Continuation of application No. PCT/JP2004/015556, filed on Oct. 14, 2004.

(30) Foreign Application Priority Data

Oct. 14, 2003 (JP) .............................. 2003-354086
Jul. 6, 2004 (JP) .............................. 2004-199934

(51) Int. Cl.
    A61K 31/47 (2006.01)
    C07D 217/22 (2006.01)
(52) U.S. Cl. ........................ 514/310; 546/143
(58) Field of Classification Search ........................ None
    See application file for complete search history.

(56) References Cited

U.S. PATENT DOCUMENTS

| 3,535,328 A | 10/1970 | Zielinski |
| 2003/0158188 A1 | 8/2003 | Lee et al. |
| 2003/0158198 A1 | 8/2003 | Lee et al. |

FOREIGN PATENT DOCUMENTS

| EP | 1 190 710 | 3/2002 |
| GB | 2 065 121 | 6/1981 |
| WO | WO 94/06770 | 3/1994 |
| WO | WO 00/50387 | 8/2000 |
| WO | WO 01/07409 A1 | 2/2001 |
| WO | WO 01/70734 | 9/2001 |
| WO | WO 02/08221 | 1/2002 |
| WO | WO 02/16317 | 2/2002 |
| WO | WO 02/16318 | 2/2002 |
| WO | WO 02/16319 | 2/2002 |
| WO | WO 02/072536 | 9/2002 |
| WO | WO 02/090326 | 11/2002 |
| WO | WO 03/014064 | 2/2003 |
| WO | WO 03/022809 | 3/2003 |
| WO | WO 03/027064 | 4/2003 |
| WO | WO 03/053945 | 7/2003 |
| WO | WO 03/055484 | 7/2003 |
| WO | WO 03/055848 | 7/2003 |
| WO | WO 03/070247 | 8/2003 |
| WO | WO 03/080578 | 10/2003 |
| WO | WO 03/095420 | 11/2003 |
| WO | WO 03/097586 | 11/2003 |

(Continued)

OTHER PUBLICATIONS

Venkatachalam et al, Bioorganic & Medicinal Chemistry Letters, (2001), vol. 11, pp. 523-528.*

(Continued)

*Primary Examiner*—Zinna N Davis
(74) *Attorney, Agent, or Firm*—Oblon, Spivak, McClelland, Maier & Neustadt, L.L.P.

(57) ABSTRACT

The present invention relates to an ether derivative represented by the formula (I), a pharmaceutically acceptable salt thereof, a hydrate thereof or a solvate thereof

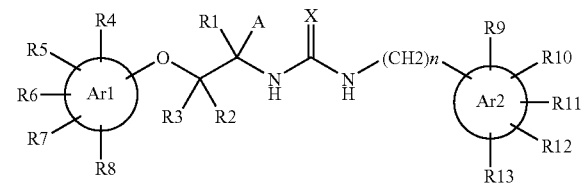

(I)

wherein each symbol is as defined in the description, and an ether derivative represented by the formula (III), a pharmaceutically acceptable salt thereof, a hydrate thereof or a solvate thereof

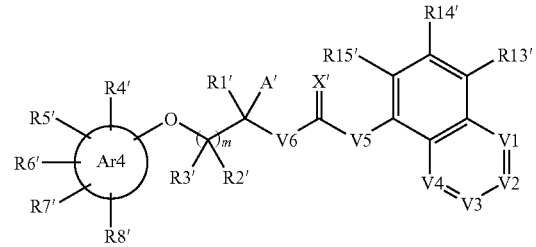

(III)

wherein each symbol is as defined in the description; a pharmaceutical composition containing the ether derivative; and a package containing the pharmaceutical composition and a description of use thereof. A pharmaceutical composition of the present invention, which contains this compound of the present invention has a superior anti-inflammatory and analgesic activity and is useful as various pharmaceutical agents such as an anti-inflammatory agent, an analgesic, a therapeutic agent for inflammatory bowel disease, a therapeutic agent for pollakiuria and/or incontinentia, a therapeutic agent for asthma and the like.

41 Claims, 4 Drawing Sheets

FOREIGN PATENT DOCUMENTS

| WO | WO 2004/007459 | 1/2004 |
| WO | WO 2004/024710 | 3/2004 |
| WO | WO 2004/028440 | 4/2004 |
| WO | WO 2004/052845 | 6/2004 |
| WO | WO 2004/052846 | 6/2004 |

OTHER PUBLICATIONS

West, Anthony R., Solid State Chemistry and its Applications, Wiley, New York, 1988, pp. 358 & 365.*

Leallyn B. Clapp. "Reactions of Ethylenimines. III. With Phenols", Journal of the American Chemical Society, vol. 73, XP-002458712, 1951, pp. 2584-2586.

D.G. Hayman et al.; "Hypoglycaemic agents"; J. Pharm. Pharmacol., vol. 16, pp. 538-548; 1964.

CAplus, DN: 64:75542, T. Agawa et al., "Thermal decomposition of adducts from isocyanates and diethyl malonate", Kogyo Kagaku Zasshi, 1965, 68(12), pp. 2370-2373.

D. Uzunov et al.; "Some aspects of the enantiorecognition of derivatized primary amines on a Pirkle-type chiral stationary phase utilizing tocainide and mexiletine as model compounds"; Journal of Chromatography, 1993. 645, pp. 233-239.

* cited by examiner

ETHER DERIVATIVE

CROSS REFERENCES TO RELATED APPLICATIONS

This application is a continuation of International Patent Application No. PCT/JP04/15556, filed on Oct. 14, 2004, and claims priority to Japanese Patent Application No. 2003-354086, filed on Oct. 14, 2003, and Japanese Patent Application No. 2004-199934, filed on Jul. 6, 2004.

TECHNICAL FIELD OF THE INVENTION

The present invention relates to an ether derivative having a superior anti-inflammatory and analgesic activity, and a pharmaceutical composition comprising the ether derivative as an active ingredient.

BACKGROUND OF THE INVENTION

It is considered that pain is developed by direct stimuli from damage and invasion of tissue based on various exogenous factors, amplified by various endogenous algetic substances produced by tissue damage and results in inflammatory conditions (Tanaka et al. ed.: NEW Yakurigaku, Nankodo Co., Ltd., Apr. 15, 2002, p354-355). In addition, there is a pain caused by functional abnormality of peripheral nervous system or central nervous system, rather than tissue damage, which is referred to as a neuropathic pain.

As therapeutic drugs for these pains, a wide variety of drugs have already been known, which are largely divided from the aspects of action mechanism into opioid analgesics containing narcotic analgesics such as morphine, codeine, opium alkaloids, buprenorphine, pentazocine and the like, and antipyretic analgesics (nonnarcotic analgesics) such as aspirin, indomethacin, acetaminophen and the like. While the former provides a strong analgesic effect by acting on the opioid receptor in the central nervous system, its use is limited because it causes severe side effects and dependency. While the latter acts on peripheral tissues to bring about an anti-inflammatory and analgesic effect, the level of the action is low and various side effects may express. Furthermore, a therapeutic drug effective for a neuropathic pain associated with diabetic neuropathy, trigeminal neuropathy, herpes zoster and the like has not been found yet, and the development of a pharmaceutical agent effective for a broad range of pains, including these pains, has been desired.

In recent years, during the course of studies relating to the algetic mechanism, a receptor of capsaicin (pungent component of red pepper), known to be an algetic substance, was cloned and named as a vanilloid receptor (hereinafter to be referred to as "VR1") (Nature, 389, p816 (1997)).

Since VR1 present in the capsaicin-sensitive sensory nerve is activated not only by a capsaicin-like substance but also by heat, acid ($H^+$) and the like, VR1 is considered to be involved in pains and inflammations associated with various pathologies.

To be specific, when VR1 is activated by stimuli of capsaicin and the like, the cation channel opens, the membrane is depolarized and neuropeptide is released, which in turn evokes pain and inflammation. Therefore, a substance that antagonizes activation of VR1 is potentially a superior therapeutic drug for pain and inflammation. In fact, capsazepine, known to be a VR1 receptor antagonist, has been reported to show a remarkable analgesic effect in animal models (Life Science, 69, p2911 (2001)).

On the other hand, VR1 agonist capsaicin is also considered to develop intense stimuli (pain) and then induce an analgesic effect or anti-inflammatory effect. It is postulated that capsaicin binds to a receptor to continuously open the VR1 cation channel, which in turn makes the sensory nerve unresponsive to stimuli (Pharmacol. Rev. 51, p159 (1999)). Since capsaicin has been, in fact, effectively used as an analgesic for pain in diseases such as diabetic neuropathy, rheumatoid arthritis and the like, a compound (VR1 agonist) having a capsaicin-like action mechanism is also expected to be a therapeutic drug for pain and inflammation.

In addition, a report has been documented that patients with not only pain but also inflammatory bowel diseases (Crohn's disease, ulcerative colitis etc.) show high expression of VR1, and therefore, a compound having a capsaicin-like action mechanism or an action mechanism that antagonizes responses of capsaicin is expected to be a good therapeutic drug for inflammatory bowel diseases.

As diseases involving the capsaicin-sensitive sensory nerve, pruritus, allergic and nonallergic rhinitis, (e.g., hyperactive bladder) pollakiuria and incontinentia, apoplexy, irritable bowel syndrome, respiratory diseases (asthma, chronic obstructive pulmonary disease etc.), dermatitis, gastric ulcer, duodenal ulcer, functional gastrointestinal diseases such as functional dyspepsia, gastroesophageal reflux disease and the like, and the like are known, and an antiobesity action on capsaicin has been reported. Therefore, a compound having a capsaicin-like action mechanism or an action mechanism that antagonizes responses of capsaicin is also useful as a therapeutic drug for these diseases and conditions.

As mentioned above, a compound having a capsaicin-like action mechanism or an action mechanism that antagonizes, responses of capsaicin is highly expected to be a therapeutic drug for neuropathic pain, for which existing analgesics are ineffective, such as diabetic neuropathy and the like, as well as pains caused by various diseases such as rheumatoid arthritis and the like, and further, being apart from pain, a therapeutic drug for various diseases in which VR1 is involved, such as ulcerative colitis and the like.

As the vanilloid receptor antagonist, the compounds of the following formulas (a), (b), (c) and (d) are described in US 2003/0158198 A, WO 02/16317, WO 02/072536 and WO 02/08221, respectively. In addition, the compounds of the following formulas (e) and (f) are described in WO 03/014064 and WO 03/080578, respectively.

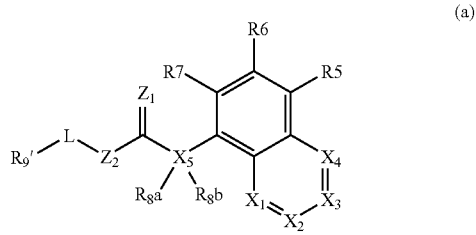

(a)

wherein $X_1$ is N or $CR_1$, $X_2$ is N or $CR_2$, $X_3$ is N, $NR_3$, or $CR_3$, $X_4$ is N or $CR_4$, $X_5$ is N and the like, $Z_1$ is O and the like, $Z_2$ is NH and the like, L is —$(CH_2)_mO(CH_2)_n$— and the like, m=0 and the like, n=2 and the like, and $R_9'$ is aryl, heterocycle and the like, provided that at least one of $X_1$, $X_2$, $X_3$ and $X_4$ is N.

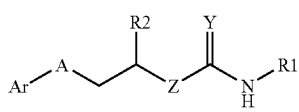

wherein R1 is Ar'—(CH$_2$)$_m$— and the like, m is 1-4, Y is O and the like, Z is NR3 and the like, R2 is hydrogen, C$_{1-6}$ lower alkyl group or Ar"—(CH$_2$)$_n$— and the like, p is 0-4 and the like, and A is O and the like.

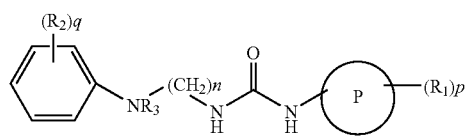

wherein P is phenyl or naphthyl, and n is 2 and the like.

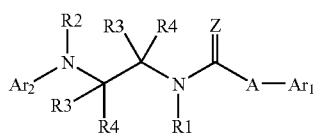

wherein A is NR$_A$ and the like, Z is O or S, R1 and R2 are H or alkyl, and R3 and R4 are H, halogen and the like.

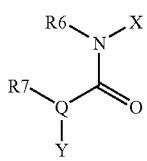

wherein Q is CH or N, R6 and R7 are H or methyl, X is phenylalkyl group and the like, Y is 7-hydroxy-1-naphthyl group and the like.

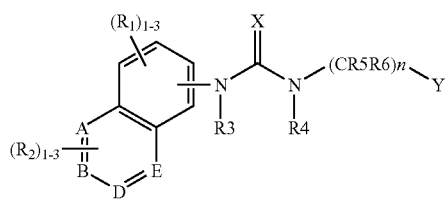

wherein X is O and the like, A, B, D and E are C or N, R3 and R4 are H and the like, R5 and R6 are H or alkyl and the like, n is 0-3, Y is aryl and the like.

Besides the above-mentioned, vanilloid receptor antagonists and capsaicin-like agonistic substances are known (US 2003/0158188 A, WO 03/070247, WO 02/072536, WO 02/16318, WO 02/16319, WO 00/50387, WO 03/053945, WO 03/027064). However, all of these compounds are structurally different from the compound of the formula (I) to be mentioned below.

In addition, the following compound (X-1) is a known compound (GB 2065121) and known as a thromboxane A2 synthesis enzyme inhibitor. However, it does not contain any description relating to the action mechanism described in the present invention, and while the following compounds (X-2) and (X-3) are known compounds (U.S. Pat. No. 3,535,328), it does not contain any description relating to the pharmacological effect and action mechanism described in the present invention.

Furthermore, the following compound (X-4)(described in Journal of Pharmacy and Pharmacology. 16, (8), p538-48 (1964)), the following compound (X-5) (described in Kogyo Kagaku Zasshi 68 (12), p2370-2373 (1965) and the following compounds (X-6) and (X-7) (described in Journal of Chromatography, 645(2), p233-239 (1993)) are known compounds but none of these documents contain a description relating to the pharmacological effect and action mechanism described in the present invention.

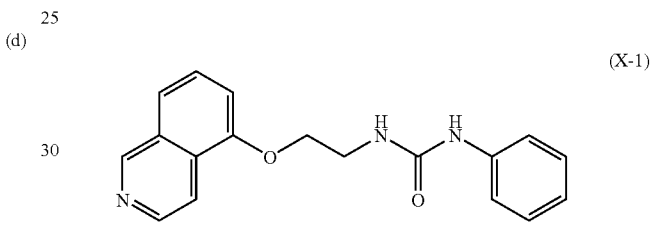

(X-1)

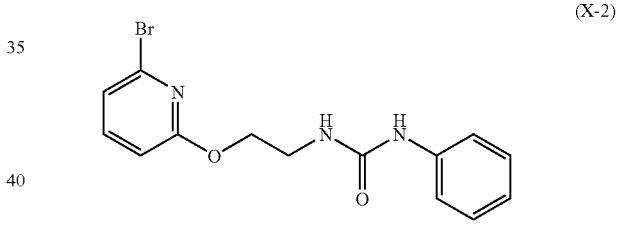

(X-2)

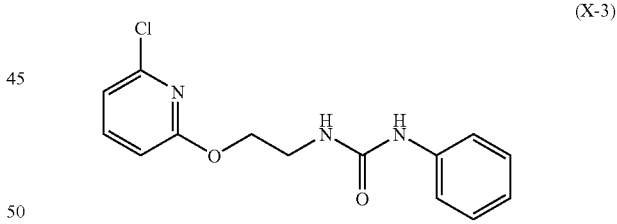

(X-3)

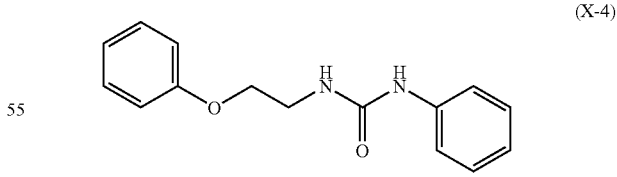

(X-4)

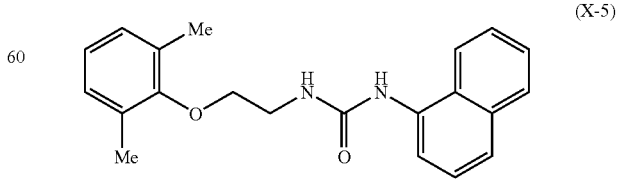

(X-5)

-continued

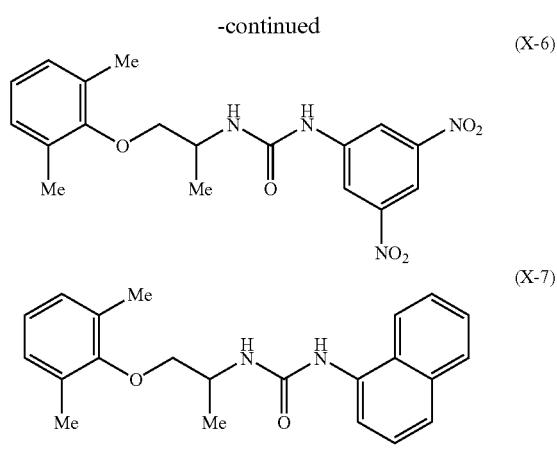

SUMMARY OF THE INVENTION

The problems to be solved by the present invention are provision of an ether derivative having superior anti-inflammatory and analgesic activity, and a pharmaceutical composition containing the ether derivative as an active ingredient.

The present inventors have conducted intensive studies in an attempt to solve the above-mentioned problems and found that an ether derivative having a particular chemical structure has a superior anti-inflammatory and analgesic activity, is useful as a pharmaceutical agent, and has a particularly strong capsaicin-like action or antagonistic action against response to capsaicin, and further found that an ether derivative having a particular chemical structure shows a large area under the blood concentration time curve and high bioavailability by oral administration, and is stable to metabolic enzymes in vivo, which resulted in the completion of the present invention.

Accordingly, the present invention relates to an ether derivative represented by the following formula (I) or (III), a pharmaceutical composition containing the ether derivative as an active ingredient, particularly, a pharmaceutical composition useful as a therapeutic agent for inflammatory bowel diseases (Crohn's disease, ulcerative colitis etc.), (e.g., hyperactive bladder) pollakiuria and/or incontinentia, irritable bowel syndrome, respiratory diseases (asthma, chronic obstructive pulmonary disease etc.), diabetic neuropathy, pruritus, esophageal reflux or articular rheumatism and the like, as a pharmaceutical agent having anti-inflammatory and analgesic activity.

Accordingly, the present invention provides:

(1) An ether derivative of the formula (I), a pharmaceutically acceptable salt thereof, a hydrate thereof, or a solvate thereof:

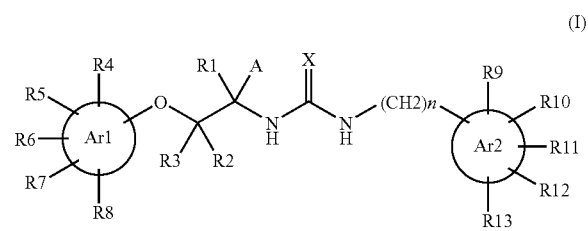

wherein
Ar1 and Ar2 are each independently an aryl group, a heteroaryl group, or a nonaromatic heterocyclic group,
X is an oxygen atom or a sulfur atom,
n is an integer of 0-2,
R1-R3 are each idenpendently a hydrogen atom or a $C_{1-6}$ alkyl group,
R4-R8 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{6-12}$ aryl-carbonylamino group, a $C_{1-6}$ alkyl group substituted by one or more hydroxy groups, a carboxyl group, a phenyl group, or a naphthyl group,
R9-R13 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{6-12}$ aryl-carbonylamino group, a $C_{1-6}$ alkyl group substituted by one or more hydroxy groups, a carboxyl group, a $C_{1-6}$ alkoxy group substituted by one or more amino groups, or a $C_{1-6}$ alkoxy group substituted by one or more hydroxy groups, and
A is a hydrogen atom, a $C_{1-6}$ alkyl group, a $C_{1-6}$ alkyl group substituted by one or more hydroxy groups, a $C_{1-6}$ alkyl group substituted by one or more carboxyl groups, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, or a group represented by the formula (II):

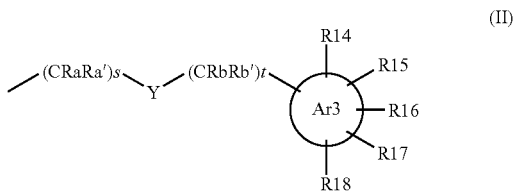

wherein
Ar3 is an aryl group, a heteroaryl group, or a nonaromatic heterocyclic group,
Y is —O—, —$CH_2$—, —NR19, —S—, —S(O)—, —$SO_2$—, —$NR19SO_2$—, —$SO_2NR19$-, —C(O)NR19-, —NR19C(O)—, —NR19C(O)O—or —OC(O)NR19-,
Ra, Ra', Rb, and Rb' are each independently a hydrogen atom or a $C_{1-6}$ alkyl group,
s is an integer of 1 or 2,
t is an integer of 0-2, R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{16}$ alkylsulfonylamino group, a formylamino group, a $C_{1-6}$ alkyl-carbonylamino group, a $C_{2-6}$ alkenyl-carbonylamino group, a $C_{6-12}$ aryl-carbonylamino group, a $C_{1-6}$ alkyl group substituted by one or more hydroxy groups, a carboxyl group, a $C_{1-6}$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{16}$ alkyl groups, a $C_{1-6}$ alkoxy-carbonyl group, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and R19 is hydrogen atom or a $C_{16}$ alkyl group, provided that:

(1) when Ar2 is a bicyclic heteroaryl containing at least one nitrogen atom, then A is a group other than a hydrogen atom, (2) when n is an integer of 1-2, then A is a group represented by the formula (II) wherein Y is —O—, —NR19-, —S—, —S(O)—, —SO$_2$—, —NR19SO$_2$—, —SO$_2$NR19-, —C(O)NR19-, —NR19C(O)—, —NR19C(O)O— or —OC(O)NR19-), and (3) the following compounds (X-1)-(X-7) are excluded (X-1)

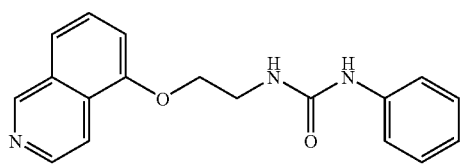

(X-2)

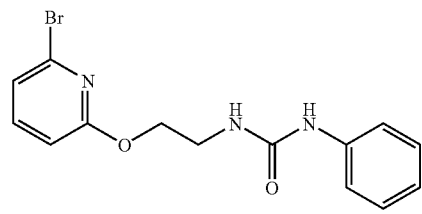

(X-3)

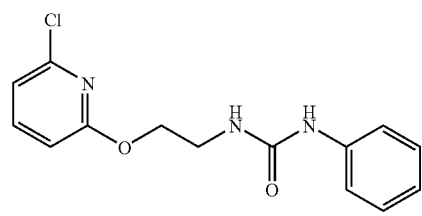

(X-4)

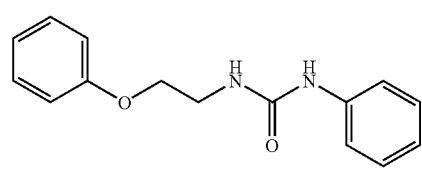

(X-5)

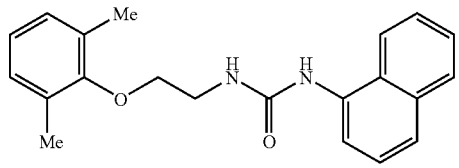

(X-6)

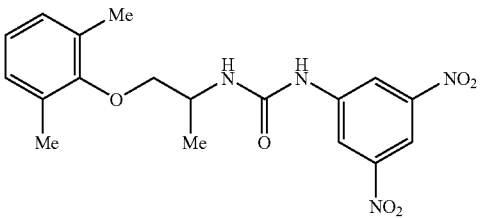

(X-7)

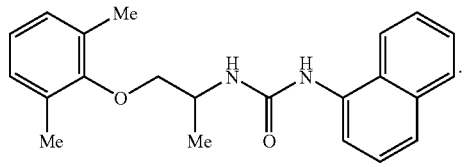

(2) An ether derivative represented by the formula (I), a pharmaceutically acceptable salt thereof, a hydrate thereof, or a solvate thereof:

(I)

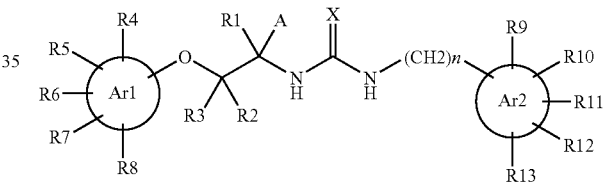

wherein

Ar1 and Ar2 are each independently a phenyl group, a naphthyl group, a heteroaryl group, an indolinyl group, or an isoindolinyl group, X is an oxygen atom or a sulfur atom, n is an integer of 0-2, R1-R3 are each independently a hydrogen atom or a $C_{1-6}$ alkyl group, R4-R8 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a $C_{1-6}$ acylamino group, a $C_{1-6}$ alkyl group substituted by one or more hydroxy groups, a carboxyl group, a phenyl group, or a naphthyl group, R9-R13 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by a $C_{1-6}$ alkyl groups, a $C_{1-6}$ alkylsulfonylamino group, a $C_{1-6}$ acylamino group, a $C_{1-6}$ alkyl group substituted by one or more hydroxy groups, a carboxyl group, a $C_{1-6}$ alkoxy group substituted by one or more amino groups, or a $C_{1-6}$ alkoxy group substituted by one or more hydroxy groups, and A is a hydrogen atom, a $C_{1-6}$ alkyl group, a $C_{1-6}$ alkyl group substituted by one or more hydroxy groups, a $C_{1-6}$ alkyl group substituted by one or more carboxyl groups, a $C_{1-6}$ alkyl group substituted by one or more amino groups, a $C_{1-6}$ alkyl group substituted by one or more amino groups which are monosubstituted by a $C_{1-6}$ alkyl group, a $C_{1-6}$ alkyl group substituted by one or more amino groups which are disubstituted by $C_{1-6}$ alkyl groups, or a group represented by the formula (II),

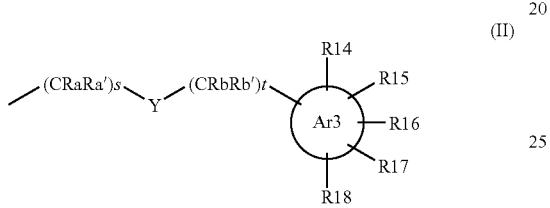

(II)

wherein
Ar3 is a phenyl group, a naphthyl group, a heteroaryl group, an indolinyl group, or an isoindolinyl group,
Y is —O—, —CH$_2$—, —NR19-, —S—, —S(O)—, —SO$_2$—, —NR19SO$_2$—, —SO$_2$NR19-, —C(O)NR19-, —NR19C(O)—, —NR19C(O)O— or —OC(O)NR19-,
Ra, Ra', Rb and Rb' are each independently a hydrogen atom or a $C_{1-6}$ alkyl group,
s is an integer of 1 or 2,
t is an integer of 0-2,
R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a $C_{1-6}$ acylamino group, a $C_{1-6}$ alkyl group substituted by one or more hydroxy groups, a carboxyl group, a $C_{1-6}$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkoxy-carbonyl group, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and
R19 is a hydrogen atom or a $C_{1-6}$ alkyl group,
provided that:
(1) when Ar2 is a bicyclic heteroaryl containing at least one nitrogen atom, then A is a group other than a hydrogen atom,
(2) when n is an integer of 1-2, then A is a group represented by the formula (II) (Y is —O—, —NR19-, —S—, —S(O)—, —SO$_2$—, —NR19SO$_2$—, —SO$_2$NR19-, —C(O)NR19-, —NR19C(O)—, —NR19C(O)O— or —OC(O)NR19-), and (3) the following compounds (X-1)-(X-7) are excluded:

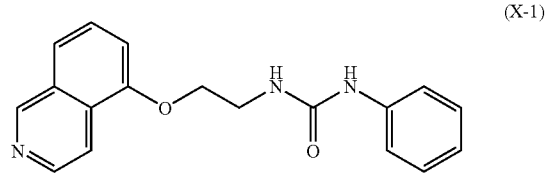

(X-1)

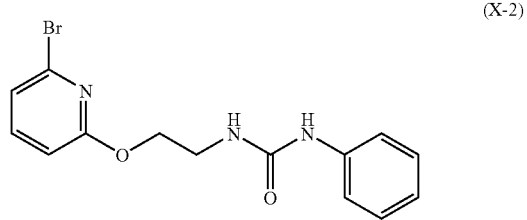

(X-2)

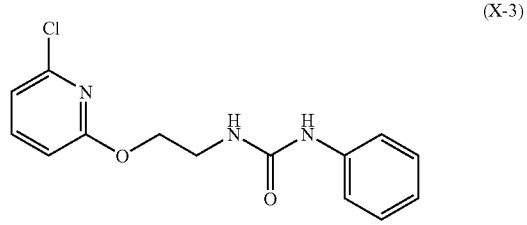

(X-3)

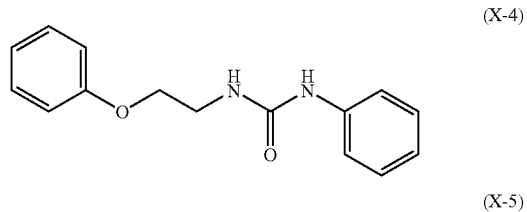

(X-4)

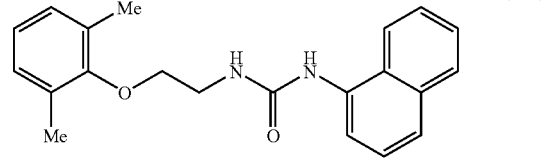

(X-5)

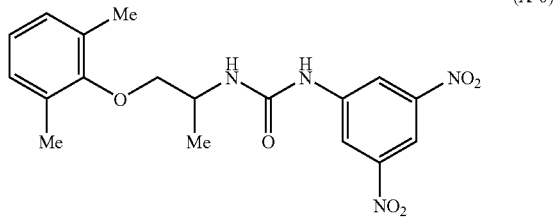

(X-6)

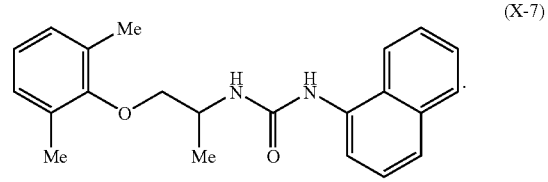

(X-7)

(3) An ether derivative represented by the formula (III), a pharmaceutically acceptable salt thereof, a hydrate thereof, or a solvate thereof:

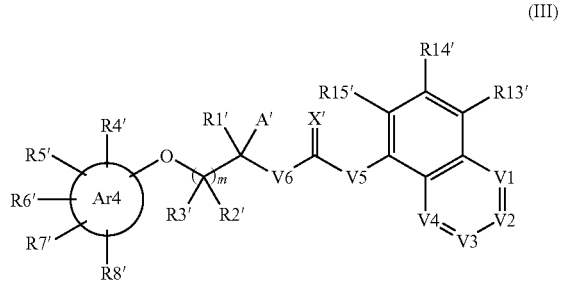

(III)

wherein

Ar4 is an aryl group or a heteroaryl group,

X' is an oxygen atom, a sulfur atom, N—CN, or N—OH,

V1 is a nitrogen atom, N→O, or CR9',

V2 is a nitrogen atom, N→O, or CR10',

V3 is a nitrogen atom or CR11',

V4 is a nitrogen atom or CR12',

V5 is NRc or CReRe',

V6 is NRd or CRfRf', m is an integer of 1-3,

R1'-R3' are each independently a hydrogen atom or a $C_{1-6}$ alkyl group and when m is 2 or 3, R2' and R3' are present in a plurality each of R2' and R3' may be the same or different, R4'-R15' are each independently a hydrogen atom, a halogen atom, a hydroxy group, a cyano group, a nitro group, a carboxyl group, a $C_{1-6}$ alkyl group optionally having one or more substituents, a $C_{2-6}$ alkenyl group optionally having one or more substituents, a $C_{2-6}$ alkynyl group optionally having one or more substituents, a $C_{3-8}$ cyclic alkyl group optionally containing one or more hetero atoms in the ring, an aryl group optionally having one or more substituents, a heteroaryl group optionally having one or more substituents, a $C_{1-6}$ alkyl group substituted by one or more aryl groups which optionally have one or more substituents, a alkyl group substituted by one or more heteroaryl groups which optionally have one or more substituents, a $C_{1-6}$ alkoxy group optionally having one or more substituents, a $C_{1-6}$ alkylthio group optionally having one or more substituents, a $C_{1-6}$ alkoxy group substituted by one or more aryl groups which optionally have one or more substituents, a $C_{1-6}$ alkylthio group substituted by one or more aryl groups which optionally have one or more substituents, a $C_{1-6}$ alkoxy group substituted by one or more heteroaryl groups which optionally have one or more substituents, a $C_{1-6}$ alkylthio group substituted by one or more heteroaryl groups which optionally having one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$ alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$ alkyl groups, a $C_{1-6}$ alkanoyl group, a $C_{7-12}$ aroyl group optionally having one or more substituents, a $C_{1-6}$ alkylsulfonylamino group, an arylsulfonylamino group optionally having one or more substituents, a heteroarylsulfonylamino group optionally having one or more substituents, a formylamino group, a $C_{1-6}$ alkyl-carbonylamino group, a $C_{2-6}$ alkenyl-carbonylamino group, a $C_{6-12}$ aryl-carbonylamino group, a $C_{1-6}$ perfluoroalkyl-carbonylamino group, a $C_{2-6}$ perfluoroalkenyl-carbonylamino group, a $C_{6-12}$ perfluoroaryl-carbonylamino group, a $C_{1-6}$ alkylsulfonyl group, or a $C_{1-6}$ alkylsulfinyl group, or of R4', R5', R6', R7' and R8', those bonded to adjacent carbon atoms are optionally bonded to each other to form, together with the constituent carbon atoms of Ar4, a saturated or unsaturated ring, wherein the ring formed optionally contains one or more hetero atoms, A' is a hydrogen atom, a halogen atom, a hydroxy group, a cyano group, a nitro group, a carboxyl group, a $C_{1-6}$ alkyl group optionally having one or more substituents, a $C_{2-6}$ alkenyl group optionally having one or more substituents, a $C_{2-6}$ alkynyl group optionally having one or more substituents, a $C_{3-8}$ cyclic alkyl group which optionally contains one or more hetero atoms in the ring, an aryl group optionally having one or more substituents, a heteroaryl group optionally having one or more substituents, a $C_{1-6}$ ailcyl group substituted by one or more aryl groups which optionally have one or more substituents, a $C_{1-6}$ alkyl group substituted by one or more heteroaryl groups which optionally have one or more substituents, a $C_{1-6}$ alkoxy group optionally having one or more substituents, a $C_{1-6}$ alkylthio group optionally having one or more substituents, a $C_{1-6}$ alkoxy group substituted by one or more aryl groups which optionally have one or more substituents, a $C_{1-6}$ alkylthio group substituted by one or more aryl groups which optionally have one or more substituents, a $C_{1-6}$ alkoxy group substituted by one or more heteroaryl groups which optionally have one or more substituents, a $C_{1-6}$ alkylthio group substituted by one or more heteroaryl groups which optionally have one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$ alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$ alkyl groups, a $C_{1-6}$ alkanoyl group optionally having one or more substituents, a $C_{7-12}$ aroyl group optionally having one or more substituents, a $C_{1-6}$ alkylsulfonylamino group, an arylsulfonylamino group optionally having one or more substituents, a heteroarylsulfonylamino group optionally having one or more substituents, a formylamino group, a $C_{1-6}$ alkyl-carbonylamino group, a $C_{2-6}$ alkenyl -carbonylamino group, a $C_{6-12}$ aryl-carbonylamino group, a $C_{1-6}$ alkylsulfonyl group, a $C_{1-6}$ alkylsulfinyl group, or a group represented by the formula (II):

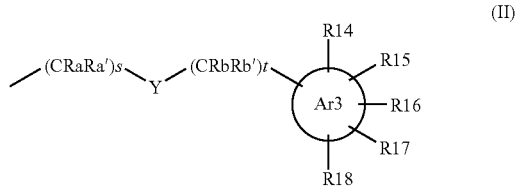

(II)

wherein

Ar3 is an aryl group, a heteroaryl group, or a nonaromatic heterocyclic group, Y is —O—, —CH₂—, —NR19-, —S—, S(O)—, —SO2—, —NR19SO2—, —SO2NR19-, —C(O)NR19-, -NR19C(O)—, —NR19C(O)O— or —OC(O)NR19-, Ra, Ra', Rb, and Rb' are each independently a hydrogen atom or a $C_{1-6}$ alkyl group, s is an integer of 1 or 2, t is an integer of 0-2, R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{7-12}$ aryl-carbonylamino group, a $C_{1-6}$ alkyl group substituted by one or more hydroxy groups, a carboxyl group, a $C_{1-6}$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkoxy-carbonyl group, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and R19 is hydrogen atom or a $C_{1-6}$ alkyl group, and Rc, Rd, Re, Re', Rf, and Rf' are each independently a hydrogen atom or a $C_{1-6}$ alkyl group, provided that:

(1) when at least one of V1, V2, V3, and V4 is a nitrogen atom, then at least one of R1', R2', R3', and A' is a group other than a hydrogen atom, and (2) the following compounds (X-5) and (X-7) are excluded:

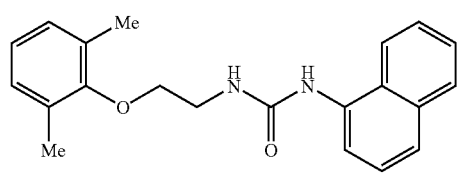

(X-5)

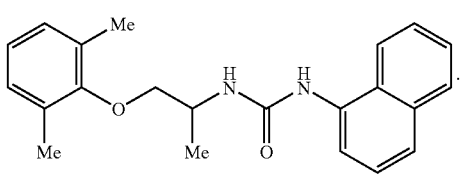

(X-7)

(4) An ether derivative represented by the formula (III), a pharmaceutically acceptable salt thereof, a hydrate thereof, or a solvate thereof:

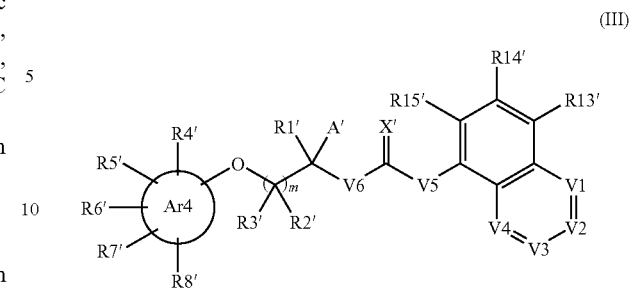

(III)

wherein

Ar4 is a phenyl group, a naphthyl group, or a heteroaryl group,

X' is an oxygen atom, a sulfur atom, N—CN, or N—OH,

V1 is a nitrogen atom, N→O, or CR9',

V2 is a nitrogen atom, N→O, or CR10',

V3 is a nitrogen atom or CR11',

V4 is a nitrogen atom or CR12',

V5 is NRc or CReRe',

V6 is NRd or CRfRf', m is an integer of 1-3,

R1'-R3' are each independently a hydrogen atom or a $C_{1-6}$ alkyl group and when m is 2 or 3, and R2' or R3' are present in a multiplicity each of R2' or R3' may be the same or different, R4'-R15' are each independently a hydrogen atom, a halogen atom, a hydroxy group, a cyano group, a nitro group, a carboxyl group, a $C_{1-6}$ alkyl group optionally having one or more substituents, a $C_{2-6}$ alkenyl group optionally having one or more substituents, a $C_{2-6}$ alkynyl group optionally having one or more substituents, a $C_{3-8}$ cyclic alkyl group which optionally contains one or more hetero atoms in the ring, an aryl group optionally having one or more substituents, a heteroaryl group optionally having one or more substituents, a $C_{1-6}$ alkyl group substituted by one or more aryl groups which optionally have one or more substituents, a $C_{1-6}$ alkyl group substituted by one or more heteroaryl groups which optionally have one or more substituents, a $C_{1-6}$ alkoxy group optionally having one or more substituents, a $C_{1-6}$ alkylthio group optionally having one or more substituents, a $C_{1-6}$ alkoxy group substituted by one or more aryl groups which optionally have one or more substituents, a $C_{1-6}$ alkylthio group substituted by one or more aryl groups which optionally have one or more substituents, a $C_{1-6}$ alkoxy group substituted by one or more heteroaryl groups which optionally have one or more substituents, a $C_{1-6}$ alkylthio group substituted by one or more heteroaryl groups which optionally have one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$ alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$ alkyl groups, a $C_{1-6}$ alkanoyl group, a $C_{7-12}$ aroyl group optionally having one or more substituents, a $C_{1-6}$ alkylsulfonylamino group, an arylsulfonylamino group optionally having one or more substituents, a heteroarylsulfonylamino group optionally having one or more substituents, a $C_{1-6}$ acylamino group, a $C_{2-6}$ perfluoroacylamino group, a $C_{1-6}$ alkylsulfonyl group, or a $C_{1-6}$ alkylsulfinyl group, or of R4', R5', R6', R7', and R8', those bonded to adjacent carbon atoms are optionally bonded to each other to form, together with the constituent carbon atoms of Ar4, a saturated or unsaturated ring, wherein the ring formed optionally contains one or more hetero atoms, A' is a hydrogen atom, a halogen atom, a hydroxy group, a cyano group, a nitro group, a carboxyl group, a $C_{1-6}$ alkyl group optionally having one or more substituents, a $C_{2-6}$ alkenyl group optionally having one or more substituents, a $C_{2-6}$ alkynyl group optionally having one or more substituents, a $C_{3-8}$ cyclic alkyl group which optionally contains one or more hetero atoms in the ring, an aryl group optionally having one or more substituents, a heteroaryl group optionally having one or more substituents, a $C_{1-6}$ alkyl group substituted by one or more aryl groups which optionally have one or more substituents, a $C_{1-6}$ alkyl group substituted by one or more heteroaryl groups which optionally have one or more substituents, a $C_{1-6}$ alkoxy group optionally having one or more substituents, a $C_{1-6}$ alkylthio group optionally having one or more substituents, a $C_{1-6}$ alkoxy group substituted by one or more aryl groups which optionally have one or more substituents, a $C_{1-6}$ alkylthio group substituted by one or more aryl groups which optionally have one or more substituents, a $C_{1-6}$ alkoxy group substituted by one or more heteroaryl groups which optionally have one or more substituents, a $C_{1-6}$ alkylthio group substituted by one or more heteroaryl groups which optionally have one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$ alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$ alkyl groups, a $C_{1-6}$ alkanoyl group, a $C_{7-12}$ aroyl group optionally having one or more substituents, a $C_{1-6}$ alkylsulfonylamino group, an arylsulfonylamino group optionally having one or more substituents, a heteroarylsulfonylamino group optionally having one or more substituents, a $C_{1-6}$ acylamino group, a $C_{1-6}$ alkylsulfonyl group, a $C_{1-6}$ alkylsulfinyl group, or a group represented by the formula (II):

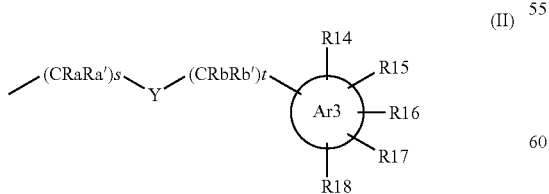

(II)

wherein

Ar3 is an aryl group, a heteroaryl group, or a nonaromatic heterocyclic group,

Y is —O—, —CH$_2$—, —NR19-, —S—, —S(O)—, —SO$_2$—, —NR19SO$_2$—, —SO$_2$NR19-, —C(O)NR19-, —NR19C(O)—, —NR19C(O)O— or —OC(O)NR19-,

Ra, Ra', Rb, and Rb' are each independently a hydrogen atom or a $C_{1-6}$ alkyl group, s is an integer of 1 or 2, t is an integer of 0-2, R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{7-12}$ aryl-carbonylamino group, a $C_{1-6}$ alkyl group substituted by one or more hydroxy groups, a carboxyl group, a $C_{1-6}$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkoxy-carbonyl group, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and R19 is hydrogen atom or a $C_{1-6}$ alkyl group, and Rc, Rd, Re, Re', Rf, and Rf' are each independently a hydrogen atom or a $C_{1-6}$ alkyl group, provided that:

(1) when at least one of V1, V2, V3, and V4 is a nitrogen atom, then at least one of R1', R2', R3', and A' is a group other than a hydrogen atom, and (2) the following compounds (X-5) and (X-7) are excluded:

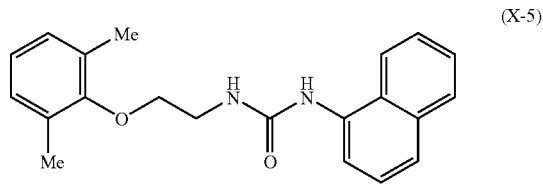

(X-5)

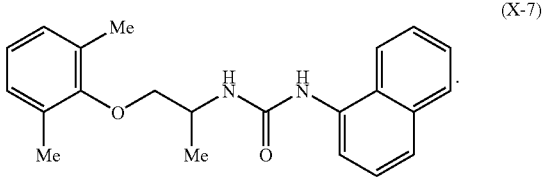

(X-7)

DETAILED DESCRIPTION OF THE INVENTION

Figure 1:
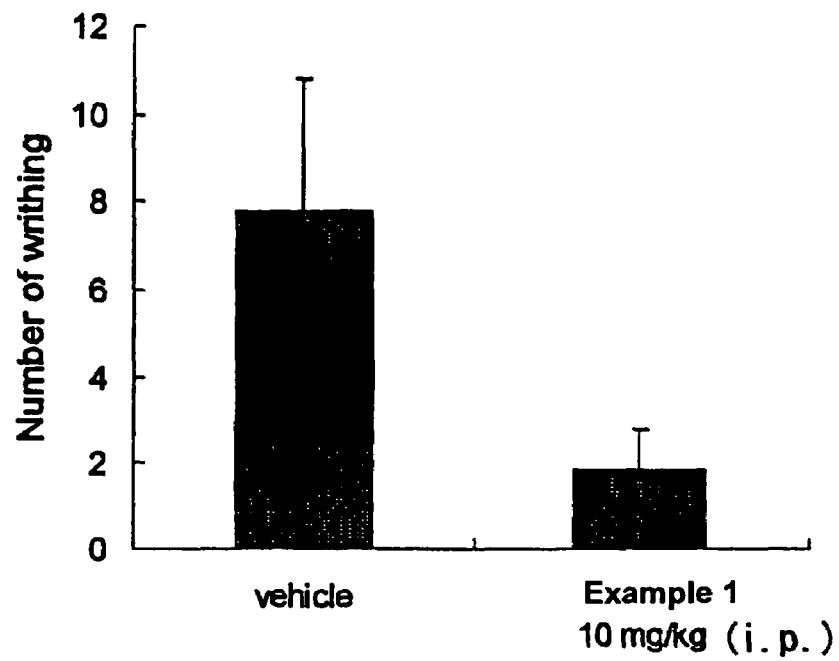
FIG. 1 shows the number of writhing in the acetic acid-induced writhing method when the compound of the present invention was administered.
Figure 1:
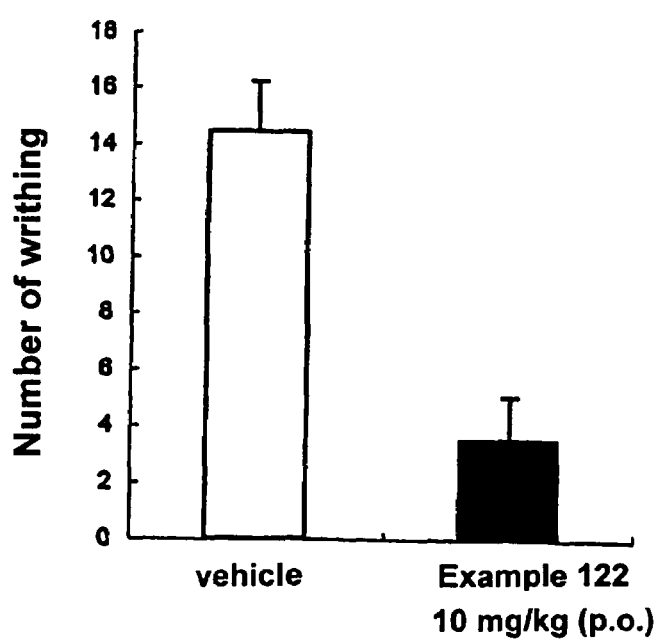

The "aryl group" in the formulas (I) and (III) shows a monocyclic or bicyclic aromatic ring group consisting of carbon atoms and, for example, phenyl group and naphthyl group can be mentioned. The "heteroaryl group" is a 5- or 16-membered monocyclic, or bicyclic aromatic heterocyclic group containing, as a ring atom, 1 to 3, preferably 1 or 2, hetero atoms selected from an oxygen atom, a sulfur atom and a nitrogen atom. For example, pyridyl group, pyridazinyl group, pyrimidinyl group, pyrazinyl group, furyl group, thienyl group, pyrrolyl group, isoxazolyl group, oxazolyl group, isothiazolyl group, thiazolyl group, pyrazolyl group, imidazolyl group, benzofuranyl group, benzothienyl group, indolyl group, isoindolyl group, benzoxazolyl group, benzthiazolyl group, benzimidazolyl group, indazolyl group, benzisoxazolyl group, benzisothiazolyl group, quinolyl group, isoquinolyl group, cinnolinyl group, phthalazinyl group, quinazolinyl group and quinoxalinyl group can be mentioned.

As the "halogen atom", fluorine, chlorine, bromine and iodine can be mentioned.

As an alkyl group as a component of the "alkyl group", "perfluoroalkyl group", "alkoxy group", "perfluoroalkoxy group", "alkyl-carbonyl group", "amino group monosubstituted by alkyl group", "amino group disubstituted by alkyl group", "alkylthio group", "alkylsulfinyl group", "alkylsulfonyl group", "alkylsulfonylamino group", "alkoxy-carbonyl group", "alkoxy-carbonylamino group" and the like, straight chain or branched $C_{1-6}$ alkyl groups such as methyl, ethyl, propyl, isopropyl, butyl, isobutyl, t-butyl, n-pentyl, isopentyl, n-hexyl, isohexyl and the like can be mentioned.

As the "alkenyl group", a straight chain or branched $C_{2-6}$ alkenyl group containing each isomer, such as vinyl, allyl, propenyl, butenyl, pentenyl, hexenyl, heptenyl and the like can be mentioned.

As the "alkynyl group", a straight chain or branched $C_{2-6}$ alkynyl group containing each isomer, such as ethynyl, propynyl, butynyl, pentynyl and the like can be mentioned.

As the "cycloalkyl group", a saturated or unsaturated $C_{3-8}$ cycloalkyl group such as cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl and the like can be mentioned.

As the "nonaromatic heterocyclic group", a 5- to 7-membered monocyclic, or bicyclic nonaromatic heterocyclic group containing, as a ring atom, 1 or 2 hetero atoms selected from an oxygen atom, a sulfur atom and a nitrogen atom can be mentioned. For example, pyrrolidinyl, pyrazolidinyl, imidazolidinyl, pyrrolinyl, pyrazolinyl, imidazolinyl, tetrahydrofuranyl, tetrahydrothiophenyl, thiazolidinyl, piperidinyl, piperazinyl, quinuclidinyl, tetrahydropyranyl, morpholinyl, thiomorpholinyl, dioxolanyl, homopiperidinyl, homopiperazinyl, indolinyl, isoindolinyl, chromanyl and isochromanyl can be mentioned.

As an acyl group as a component of the "acylamino group", a saturated or unsaturated $C_{1-15}$, preferably $C_{1-6}$, aliphatic or aromatic acyl group such as formyl group, a $C_{1-6}$ alkyl-carbonyl group (e.g., acetyl, propionyl, butyryl, valeryl, pivaloyl, and the like), $C_{2-6}$ alkenyl-carbonyl group (e.g., acryloyl, crotonoyl and the like), $C_{6-12}$ aryl-carbonyl group (e.g., benzoyl, naphthoyl, toluoyl etc.) and the like can be mentioned. As the "acylamino group", for example, formylamino group, $C_{1-6}$ alkyl-carbonylamino group, $C_{2-6}$ alkenyl-carbonylamino group, $C_{6-12}$ aryl-carbonylamino group and the like can be mentioned.

As an "acyl" as a component of the "perfluoroacylamino group", for example, those similar to the "acyl" mentioned above in the aforementioned explanation of the "acylamino group" can be mentioned (except formyl group). "perfluoroacylamino group", for example, $C_{1-6}$ perfluoroalkyl-carbonylamino group, $C_{2-6}$ perfluoroalkenyl-carbonylamino group, $C_{6-12}$ perfluoroaryl-carbonylamino group and the like can be mentioned.

As the "alkanoyl group", for example, a $C_{1-6}$ alkanoyl group [for example, formyl group, $C_{1-6}$ alkyl-carbonyl group (e.g., acetyl, propionyl, butyryl, valeryl, pivaloyl, etc.) and the like] can be mentioned.

As the "aroyl group", for example, $C_{6-12}$, preferably $C_{7-12}$, aroyl group [for example, $C_{6-12}$ aryl-carbonyl group (e.g., phenylcarbonyl, naphthylcarbonyl etc.) and the like] can be mentioned.

The "perfluoroalkyl group" is an alkyl group wherein hydrogen atoms are all substituted by fluorine atom and, for example, trifluoromethyl, pentafluoroethyl and the like can be mentioned.

With regard to the "optionally having one or more substituents" here, the substituent may be single or plural and, as the substituent, hydrogen atom, halogen atom, hydroxy group, cyano group, nitro group, carboxyl group, $C_{1-6}$ alkyl group, $C_{2-6}$ alkenyl group, $C_{2-6}$ alkynyl group, $C_{3-8}$ cyclic alkyl group (optionally containing one or more hetero atoms in the ring), aryl group, heteroaryl group, $C_{1-6}$ alkoxy group, $C_{1-6}$ alkylthio group, $C_{1-6}$ alkoxy group or alkylthio group substituted by aryl group, $C_{1-6}$ alkoxy group or alkylthio group substituted by heteroaryl group, $C_{3-8}$ cyclic alkyl(optionally containing one or more hetero atoms in the ring)oxy group, aryloxy group, heteroaryloxy group, $C_{1-3}$ perfluoroalkoxy group, $C_{1-3}$ perfluoroalkylthio group, $C_{1-6}$ alkoxy group substituted by hydroxy group, $C_{1-6}$ alkoxy group substituted by $C_{1-6}$ alkoxy group, amino group, amino group monosubstituted by $C_{1-6}$ alkyl group, amino group disubstituted by $C_{1-6}$ alkyl group, $C_{1-6}$ alkoxy -carbonyl group, $C_{1-6}$ alkyl-carbonyloxy group, $C_{3-8}$ cycloalkylcarbonyloxy group (optionally containing one or more hetero atoms in the ring), carbamoyl group, carbamoyl group monosubstituted by $C_{1-6}$ alkyl group, carbamoyl group disubstituted by $C_{1-6}$ alkyl group, sulfamoyl group, sulfamoyl group monosubstituted by $C_{1-6}$ alkyl group, sulfamoyl group disubstituted by $C_{1-6}$ alkyl group, $C_{1-6}$ alkanoyl group, $C_{7-12}$ aroyl group (preferably a $C_{7-12}$ aroyl group), $C_{1-6}$ alkylsulfonylamino group, arylsulfonylamino group, heteroarylsulfonylamino group, $C_{1-6}$ acylamino group, $C_{1-6}$ alkoxy-carbonylamino group, $C_{1-6}$ alkylsulfonyl group, $C_{1-6}$ alkylsulfinyl group, $C_{1-6}$ alkoxy group substituted by amino group, $C_{1-6}$ alkoxy group substituted by amino group monosubstituted by $C_{1-6}$ alkyl group, $C_{1-6}$ alkoxy group substituted by amino group disubstituted by $C_{1-6}$ alkyl group, and the like can be mentioned.

In the formula (I), as Ar1, a phenyl group or a pyridyl group is preferable.

As Ar2, a phenyl group, a pyridyl group, a naphthyl group, a quinolyl group or an isoquinolyl group is preferable.

As X, an oxygen atom or a sulfur atom is preferable.

As n, an integer of 1 or 2 is preferable.

As R1-R3, a hydrogen atom is preferable.

As R4-R8, a hydrogen atom, a halogen atom, a $C_{1-6}$ alkyl group or a $C_{1-3}$ perfluoroalkyl group is preferable.

As R9-R13, a hydrogen atom, a halogen atom, a $C_{1-6}$ alkyl group, a $C_{1-3}$ perfluoroalkyl group, a hydroxyl group, a $C_{1-6}$ alkoxy group, a $C_{1-6}$ alkylsulfonylamino group or a $C_{1-6}$ alkoxy group substituted by one or more amino groups is preferable.

As A, a hydrogen atom or a group represented by the formula (II) is preferable.

As Ar3, a phenyl group or a pyridyl group is preferable.

As Y, an oxygen atom, —$SO_2$— or —NHC(O)— is preferable.

As Ra, Ra', Rb and Rb', a hydrogen atom or a $C_{1-6}$ alkyl group is preferable.

As s, an integer of 1 or 2 is preferable.

As t, an integer of 0 or 1 is preferable.

As R14-R18, a hydrogen atom, a halogen atom, a $C_{1-6}$ alkyl group, a $C_{1-3}$ perfluoroalkyl group, a hydroxyl group, a $C_{1-6}$ alkoxy group, a cyano group, a $C_{1-6}$ alkylthio group, a $C_{1-6}$ alkylsulfinyl group, a $C_{1-6}$ alkylsulfonyl group, an amino group, an amino group monosubstituted by a $C_{1-6}$ alkyl group, an amino group disubstituted by $C_{1-6}$ alkyl groups, a $C_{1-6}$ alkylsulfonylamino group, a $C_{1-6}$ acylamino group, a $C_{1-6}$ alkyl group substituted by one or more hydroxy groups, a carboxyl group, a $C_{1-6}$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkyl group substituted by one or more amino groups, a $C_{1-6}$ alkyl group substituted by one or more amino groups monosubstituted by a $C_{1-6}$ alkyl group or a $C_{1-6}$ alkyl group substituted by one or more amino groups disubstituted by $C_{1-6}$ alkyl groups is preferable.

As R19, a hydrogen atom is preferable.

A compound wherein preferable groups mentioned for the above-mentioned Ar1, Ar2, X, n, R1-R19, A, Ar3, Y, Ra, Ra', Rb, Rb', s and t are combined is more preferable.

(5) The ether derivative of the above-mentioned (1) or (2), having the formula (I), wherein A is a hydrogen atom, Ar1 is a phenyl group or a pyridyl group, Ar2 is a phenyl group, a naphthyl group or a pyridyl group, X is an oxygen atom, n is 0, and R1-R3 are each a hydrogen atom, a pharmaceutically acceptable salt thereof, a hydrate thereof or a solvate thereof is preferable.

(6) The ether derivative of the above-mentioned (1) or (2), having the formula (I), wherein A is a group represented by the formula (II), Ar1 is a phenyl group, a pyridyl group, a pyridazinyl group, a pyrimidinyl group or a pyrazinyl group, Ar2 is a phenyl group, a naphthyl group, a pyridyl group, a pyridazinyl group, a pyrimidinyl group, a pyrazinyl group, a furyl group, a thienyl group, a pyrrolyl group, an isoxazolyl group, an oxazolyl group, an isothiazolyl group, a thiazolyl group, a pyrazolyl group, an imidazolyl group, a benzofuranyl group, a benzothienyl group, an indolyl group, an isoindolyl group, a benzoxazolyl group, a benzthiazolyl group, a benzimidazolyl group, an indazolyl group, a benzisoxazolyl group, a benzisothiazolyl group, a quinolyl group, an isoquinolyl group, a cinnolinyl group, a phthalazinyl group, a quinazolinyl group, a quinoxalinyl group, an indolinyl group or an isoindolinyl group, X is an oxygen atom, n is 0, and R1-R3 are each a hydrogen atom, a pharmaceutically acceptable salt thereof, a hydrate thereof or a solvate thereof is preferable.

(7) The ether derivative of the above-mentioned (1) or (2), having the formula (I), wherein A is a group represented by the formula (II), Ar1 is a phenyl group or a pyridyl group, Ar2 is a phenyl group, a naphthyl group, a pyridyl group, a quinolyl group, an isoquinolyl group, an indolyl group or an isoindolyl group, X is an oxygen atom, n is 0, R1-R3 are each a hydrogen atom, Ar3 is a phenyl group or a pyridyl group, Y is —O—, —$SO_2$— or —NHC(O)—, Ra, Ra', Rb and Rb' are each a hydrogen atom, s is 1, t is 0 or 1, and R14-R18 are each a same group as described in the above-mentioned (1) or (2), a pharmaceutically acceptable salt thereof, a hydrate thereof or a solvate thereof is preferable.

In the formula (III), as a group represented by Ar4, a phenyl group, a naphthyl group, a pyridyl group, a quinolyl group, an isoquinolyl group or a pyrimidinyl group is preferable, and a phenyl group is more preferable.

As a group represented by X', an oxygen atom, a sulfur atom, N—CN or N—OH is preferable, and an oxygen atom is more preferable.

As a group represented by V1, V2, V3 or V4, a nitrogen atom, N→O, C—H, C—OH, C—$NH_2$, C-(halogen atom), C—($C_{1-6}$ alkyl group), C—($C_{1-6}$ alkoxy group), C—($C_{1-6}$ alkylsulfonylamino group), C-(amino group mono- or di-substituted by $C_{1-6}$ alkyl group), C—($C_{1-6}$ alkoxy group substituted by amino group mono- or di-substituted by $C_{1-6}$ alkyl group) or C—($C_{1-6}$ alkoxy group substituted by amino group) is preferable, and the following combination is more preferable:

combination 1 [V1:C—H, V2:N, V3:C—H, V4:C—H]
combination 2 [V1:C—H, V2:N→O, V3:C—H, V4:C—H]
combination 3 [V1:C—$NH_2$, V2:N, V3:C—H, V4:C—H]
combination 4 [V1:N, V2:C—H, V3:C—H, V4:C—H]
combination 5 [V1:C—H, V2:C—H, V3:C—OH, V4:C—H]

As a group represented by V5 or V6, NH or $CH_2$ is preferable, and NH is more preferable.

m is preferably 1-3, more preferably 1.

As a group represented by R1', R2' or R3', a hydrogen atom or a $C_{1-6}$ alkyl group is preferable, and a hydrogen atom is more preferable.

As a group represented by R4', R5', R6', R7' or R8', a hydrogen atom, a $C_{1-6}$ alkyl group, a halogen atom, a $C_{1-6}$ alkoxy group, a $C_{1-6}$ alkylthio group, a trifluoromethyl group, an aryl group, a cyano group, a nitro group, an amino group or an amino group mono- or di-substituted by $C_{1-6}$ alkyl group(s) is preferable, and a hydrogen atom, a $C_{1-6}$ alkyl group or a halogen atom is more preferable.

It is also preferable that, of R4', R5', R6', R7' and R8', those bonded to the adjacent carbon atoms be bonded to each other to form, together with the constituent carbon atoms of Ar4, an unsaturated ring (optionally containing one or more hetero atoms in the ring), and it is more preferable that, of R4', R5', R6', R7' and R8', those bonded to the adjacent carbon atoms be bonded to each other to form, together with Ar4, a tetrahydronaphthalene ring or an indan ring. As R13', R14' or R15', a hydrogen atom, a $C_{1-6}$ alkyl group, a halogen atom or an amino group is preferable, and a hydrogen atom, a halogen atom or an amino group is more preferable. As a group represented by A', a hydrogen atom (except when at least one of V1, V2, V3 and V4 is a nitrogen atom), a $C_{1-6}$ alkyl group, a group represented by the formula (II), a $C_{1-6}$ alkyl group substituted by a $C_{1-6}$ alkoxy group, a $C_{1-6}$ alkyl group substituted by a $C_{1-6}$ alkyl-carbonyloxy group, a $C_{1-6}$ alkyl group substituted by a $C_{3-8}$ cycloalkylcarbonyloxy group or a $C_{1-6}$ alkyl group substituted by a $C_{1-6}$ alkylthio group is preferable, and a $C_{1-6}$ alkyl group, a group represented by the formula (II) or a $C_{1-6}$ alkyl group substituted by a $C_{1-6}$ alkyl-carbonyloxy group is more preferable.

A compound wherein preferable groups mentioned for the above-mentioned Ar4, X', V1, V2, V3, V4, V5, V6, m, R1'-R8', R13'-R15' and A' are combined is more preferable.

(8) The ether derivative of the above-mentioned (3) or (4), having the formula (III), wherein
m is 1, and
V5 and V6 are each NH,
a pharmaceutically acceptable salt thereof, a hydrate thereof or a solvate thereof is preferable.

(9) The ether derivative of the above-mentioned (8), having the formula (III), wherein
X' is an oxygen atom,
a pharmaceutically acceptable salt thereof, a hydrate thereof or a solvate thereof is preferable.

(10) The ether derivative of the above-mentioned (8), having the formula (III), wherein
V1 is CR9',
V2 is a nitrogen atom or N→O,
V3 is CR11', and
V4 is CR12',
a pharmaceutically acceptable salt thereof, a hydrate thereof or a solvate thereof is preferable.

(11) The ether derivative of the above-mentioned (8), having the formula (III), wherein
V1 is CR9',
V2 is CR10',
V3 is C—OH, and
V4 is CR12',
a pharmaceutically acceptable salt thereof, a hydrate thereof or a solvate thereof is preferable.

(12) The ether derivative of the above-mentioned (8), having the formula (III), wherein
A' is a hydrogen atom or a $C_{1-6}$ alkyl group optionally having one or more substituents, and
R1', R2' and R3' are each a hydrogen atom,
a pharmaceutically acceptable salt thereof, a hydrate thereof or a solvate thereof is preferable.

(13) The ether derivative of the above-mentioned (8), having the formula (III), wherein
Ar4 is a phenyl group, a naphthyl group, a pyridyl group, a quinolyl group, an isoquinolyl group or a pyrimidinyl group, and R4', R5', R6', R7' and R8' are each independently a hydrogen atom, a $C_{1-6}$ alkyl group, a halogen atom, a $C_{1-6}$ alkoxy group, a $C_{1-6}$ alkylthio group, a trifluoromethyl group, an aryl group, a cyano group, a nitro group, an amino group or an amino group mono- or di-substituted by $C_{1-6}$ alkyl group(s), or of R4', R5', R6', R7' and R8', those bonded to the adjacent carbon atoms are bonded to each other to form, together with the constituent carbon atoms of Ar4, an unsaturated ring (optionally containing one or more hetero atoms in the ring), a pharmaceutically acceptable salt thereof, a hydrate thereof or a solvate thereof is preferable.

(14) The ether derivative of the above-mentioned (10), having the formula (III), wherein
X' is an oxygen atom,
A' is a $C_{1-6}$ alkyl group optionally having one or more substituents, and
R1', R2' and R3' are each a hydrogen atom,
a pharmaceutically acceptable salt thereof, a hydrate thereof or a solvate thereof is preferable.

(15) The ether derivative of the above-mentioned (11), having the formula (III), wherein
X' is an oxygen atom,
A' is a hydrogen atom or a $C_{1-6}$ alkyl group optionally having one or more substituents, and
R1', R2' and R3' are each a hydrogen atom, a pharmaceutically acceptable salt thereof, a hydrate thereof or a solvate thereof is preferable.

(16) The ether derivative of the above-mentioned (10), having the formula (III), wherein
X' is an oxygen atom,
Ar4 is a phenyl group, a naphthyl group, a pyridyl group, a quinolyl group, an isoquinolyl group or a pyrimidinyl group, and
R4', R5', R6', R7' and R8' are each independently a hydrogen atom, a $C_{1-6}$ alkyl group, a halogen atom, a $C_{1-6}$ alkoxy group, a $C_{1-6}$ alkylthio group, a trifluoromethyl group, an aryl group, a cyano group, a nitro group, an amino group or an amino group mono- or di-substituted by $C_{1-6}$ alkyl group(s), or
of R4', R5', R6', R7' and R8', those bonded to the adjacent carbon atoms are bonded to each other to form, together with the constituent carbon atoms of Ar4, an unsaturated ring (optionally containing one or more hetero atoms in the ring), a pharmaceutically acceptable salt thereof, a hydrate thereof or a solvate thereof is preferable.

(17) The ether derivative of the above-mentioned (11), having the formula (III), wherein
X' is an oxygen atom,
Ar4 is a phenyl group, a naphthyl group, a pyridyl group, a quinolyl group, an isoquinolyl group or a pyrimidinyl group, and
R4', R5', R6', R7' and R8' are each independently a hydrogen atom, a $C_{1-6}$ alkyl group, a halogen atom, a $C_{1-6}$ alkoxy group, a $C_{1-6}$ alkylthio group, a trifluoromethyl group, an aryl group, a cyano group, a nitro group, an amino group or an amino group mono- or di-substituted by $C_{1-6}$ alkyl group(s), or
of R4', R5', R6', R7' and R8', those bonded to the adjacent carbon atoms are bonded to each other to form, together with the constituent carbon atoms of Ar4, an unsaturated ring (optionally containing one or more hetero atoms in the ring), a pharmaceutically acceptable salt thereof, a hydrate thereof or a solvate thereof is preferable.

(18) The ether derivative of the above-mentioned (9), having the formula (III), wherein
V1 is CH,
V2 is a nitrogen atom or N→O,
V3 is CH,
V4 is CH,
A' is a $C_{1-6}$ alkyl group optionally having one or more substituents, and
R1', R2' and R3' are each a hydrogen atom,
a pharmaceutically acceptable salt thereof, a hydrate thereof or a solvate thereof is preferable.

(19) The ether derivative of the above-mentioned (9), having the formula (III), wherein
V1 is CH,
V2 is CH,
V3 is C—OH,
V4 is CH,
A' is a hydrogen atom, or a $C_{1-6}$ alkyl group optionally having one or more substituents, and
R1', R2' and R3' are each a hydrogen atom, a pharmaceutically acceptable salt thereof, a hydrate thereof or a solvate thereof is preferable.

(20) The ether derivative of the above-mentioned (9), having the formula (III), wherein
Ar4 is a phenyl group,
R4', R5', R6', R7' and R8' are each independently a hydrogen atom, a $C_{1-6}$ alkyl group or a halogen atom, or
of R4', R5', R6', R7' and R8', those bonded to the adjacent carbon atoms are bonded to each other to form, together with Ar4, a tetrahydronaphthalene ring or an indan ring,
V1 is CH,
V2 is a nitrogen atom or N→O,
V3 is CH,
V4 is CH,
A' is a $C_{1-6}$ alkyl group, and
R1', R2' and R3' are each a hydrogen atom,
a pharmaceutically acceptable salt thereof, a hydrate thereof or a solvate thereof.

(21) The ether derivative of the above-mentioned (9), having the formula (III), wherein
Ar4 is a phenyl group,
R4', R5', R6', R7' and R8' are each independently a hydrogen atom, a $C_{1-6}$ alkyl group or a halogen atom, or
of R4', R5', R6', R7' and R8', those bonded to the adjacent carbon atoms are bonded to each other to form, together with Ar4, a tetrahydronaphthalene ring or an indan ring,
V1 is CH,
V2 is CH,
V3 is C—OH,
V4 is CH,
A' is a hydrogen atom or a $C_{1-6}$ alkyl group, and
R1', R2' and R3' are each a hydrogen atom,
a pharmaceutically acceptable salt thereof, a hydrate thereof or a solvate thereof is preferable.

In addition, the ether derivatives of the above-mentioned (9), which are shown below, pharmaceutically acceptable salts thereof, hydrates thereof and solvates thereof are preferable.

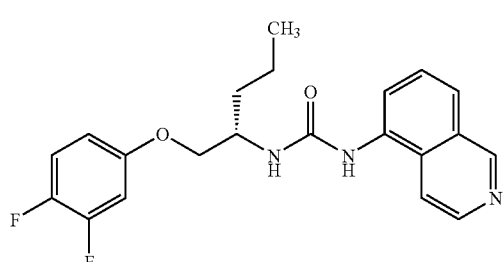

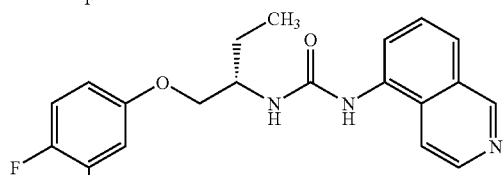

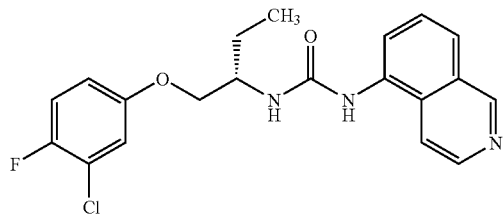

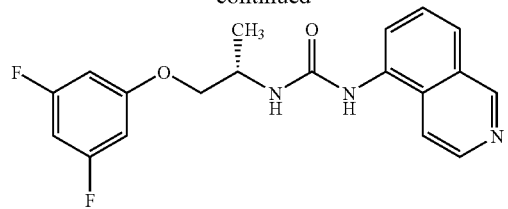

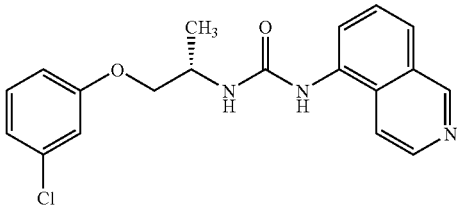

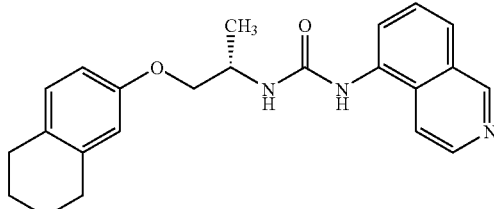

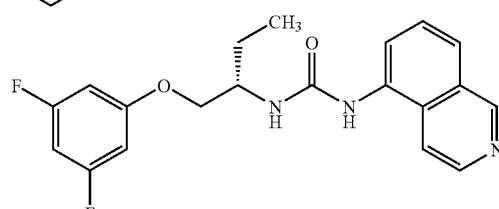

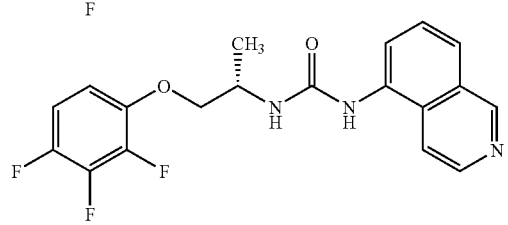

Furthermore, the compounds described in Examples are preferable, the compounds described in Examples 21, 24, 27, 38, 39, 40, 42, 44, 48, 49, 50, 51, 52, 53, 57, 62, 63, 70, 72, 73, 79, 80, 87, 90, 91, 92, 94, 96, 109, 110, 114, 122, 134, 192, 193, 194, 195, 196, 197, 198, 199, 200, 201, 202, 204, 207, 208, 210, 215, 216, 217, 218, 219, 220, 221 and 222 are more preferable, and the compounds described in Examples 38, 40, 42, 48, 49, 50, 51, 52, 53, 70, 73, 80, 91, 92, 94, 96, 134, 192, 193, 200, 201, 202, 204, 215, 216, 217, 218, 219, 220, 221 and 222 are further preferable.

When the compound of the present invention can take the form of a salt, the salt thereof may be any as long as it is pharmaceutically acceptable and when, for example, an acidic group is present in the formula, ammonium salt, salts with alkali metal such as sodium and the like, salts with alkaline earth metal such as calcium, magnesium and the like, aluminum salt, zinc salt, salts with organic amines such as triethylamine, ethanolamine, morpholine, piperidine, dicyclohexyl amine and the like, and salts with basic amino acids such as arginine, lysin and the like can be mentioned. When a basic salt is present in the formula, salts with inorganic acids such as hydrochloric acid, sulfuric acid, phosphoric acid, nitric acid, hydrobromide acid and the like, salts with organic carboxylic acids such as acetic acid, citric acid, benzoic acid, maleic acid, fumaric acid, tartaric acid, succinic acid, tannic acid, butyric acid, hibenzoic acid, pamoic acid, enanthic acid, decanoic acid, teoclic acid, salicylic acid, lactic acid, oxalic acid, mandelic acid, malic acid and the like, salts with organic sulfonic acids such as methanesulfonic acid, benzenesulfonic acid, p-toluenesulfonic acid and the like can be mentioned.

As a method for forming a salt, mixing the compound of the present invention with a necessary salt or base at a suitable amount ratio in a solvent and a dispersing agent, and cation exchange or anion exchange from form of other salt can be mentioned.

As pharmaceutically acceptable salts in the present invention, salts with inorganic acids such as hydrochloric acid, hydrobromide acid, sulfuric acid, nitric acid, phosphoric acid and the like, salts with inorganic bases such as sodium, potassium, magnesium, calcium, aluminum, lithium and the like, salts with organic acids such as formic acid, oxalic acid, maleic acid, tartaric acid, citric acid, benzoic acid, benzenesulfonic acid, toluenesulfonic acid, trifluoroacetic acid and the like, salts with organic bases such as trimethylamine, triethylamine, diethanolamine, triethanolamine, dibenzylethylenediamine, dicyclohexylamine, procaine and the like, salts with amino acids such as arginine, aspartic acid, glutamic acid, lysin, ornithine and the like, and the like can be mentioned.

The ether derivatives (I) and (III) of the present invention encompasses an optical isomer, a geometric isomer and a mixture thereof at any ratio.

The present invention also encompasses solvates (e.g., hydrate, alcohol solvate etc.) of the compound represented by the formula (I) or (III).

The compound of the present invention can also be converted to a prodrug. The prodrug in the present invention refers to a compound that can be converted in the body to produce the compound of the present invention. For example, when the active form contains a carboxyl group or a phosphoryl group, an ester thereof, an amide thereof and the like can be mentioned. When the active form contains an amino group, an amide thereof, carbamate thereof and the like can be mentioned. When the active form contains a hydroxyl group, an ester thereof, a carbonate thereof, a carbamate thereof and the like can be mentioned. When the active form is a nitrogen-containing heterocycle, an N-oxide thereof and the like can be mentioned. When the compound of the present invention is converted to a prodrug, it may be bound with an amino acid or a sugar.

Furthermore, the present invention encompasses a metabolite of the compound of the present invention. The metabolite of the compound of the present invention refers to a compound resulting from conversion of the compound of the present invention due to metabolic enzymes and the like in vivo. For example, a compound wherein a hydroxyl group has been introduced by metabolism onto the benzene ring of the compound of the present invention, a compound wherein an alkoxy group of the compound of the present invention has been converted to a hydroxyl group by metabolism, a compound wherein a nitrogen atom on the nitrogen-containing heterocycle of the compound of the present invention has been converted to N-oxide by oxidative metabolism, and the like can be mentioned. In addition, a compound wherein a carboxylic acid moiety of the compound of the present invention, or a hydroxyl group of the compound of the present invention, which has been added by metabolism, is bonded to glucuronic acid, glucose, or amino acid, and the like can be mentioned.

The compound of the present invention shows high capsaicin-like action or high antagonistic action against response of capsaicin, as well as superior bioavailability and sustainability after oral administration. It also shows superior sustainability by parenteral administration. They reflect superior properties in capsaicin-like action or antagonistic action against response of capsaicin, plasma peptide binding, solubility, liver clearance, systemic clearance, enteric permeability and the like.

Since the compound of the present invention is low in systemic clearance and superior in plasma residence time, the dose and the frequency of administration can be reduced.

The compound of the present invention shows high membrane permeability, is stable to metabolism in vivo, and superior in the area under the plasma concentration time curve and bioavailability by oral administration.

Furthermore, the compound of the present invention is also superior in safety.

The ether derivative (I) of the present invention can be produced, for example, by the following reaction scheme.

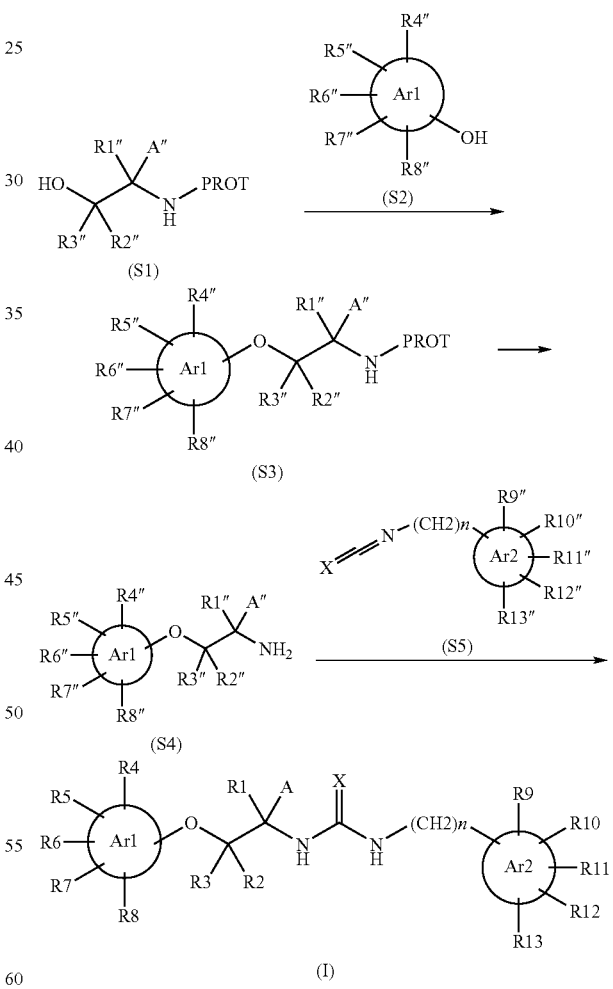

wherein PROT is an amino-protecting group such as a t-butoxycarbonyl group, a benzyloxycarbonyl group and the like; R1"-R13" and A" show R1-R13 and A, or groups convertible to R1-R13 and A in certain stages of synthesis; simultaneously, R1"-R8" and A" show R1-R8 and A in the formula (I), or groups convertible to R1-R8 and A in certain stages of synthesis; and other symbols are as defined above.

Ether (S3) can be obtained by reacting aminoalcohol (S1) having desired substituent(s) and protected in a suitable form with phenol (S2) under the conditions of Mitsunobu reaction and the like. Amine (S4) can be obtained by treating the obtained (S3) under appropriate deprotection conditions. The amino-protecting group PROT and deprotection conditions thereof are described in GREENE, T. W.; WUTS P. G.: PROTECTIVE GROUPS IN ORGANIC SYNTHESIS (SECOND EDITION), JOHN WILEY & SONS, INC. and the like. For example, when PROT is a t-butoxycarbonyl group, a method including treatment with a dioxane solution of hydrogen chloride and the like, and the like can be mentioned. When, for example, PROT is a benzyloxycarbonyl group, a method including reaction in the presence of a suitable catalyst such as palladium-carbon and the like in a hydrogen atmosphere and the like can be mentioned. By reacting the obtained amine (S4) with isocyanate or isothiocyanate (S5) having desired substituent(s) in a solvent such as dichloromethane, acetonitrile and the like in the presence of a base such as triethylamine and the like, as necessary, (I) can be obtained.

As a different method to obtain (S3), the following method can be mentioned. That is, aminoalcohol (S1) having desired substituent(s) and protected in a suitable form is reacted with methanesulfonyl chloride, p-toluenesulfonyl chloride and the like in a solvent such as dichloromethane and the like in the presence of a suitable base such as triethylamine and the like, then reacted with lithium chloride, lithium bromide and the like in a solvent such as dimethylformamide and the like and then reacted with phenol (S2) in a solvent such as dimethylformamide and the like in the presence of a base such as potassium carbonate and the like, and the like to give ether (S3).

Compound (S10), which is an ether derivative (III) of the present invention wherein V5 is N-Rc, V6 is N-Rd, and X' is an oxygen atom or a sulfur atom, can be produced, for example, by the following method.

-continued

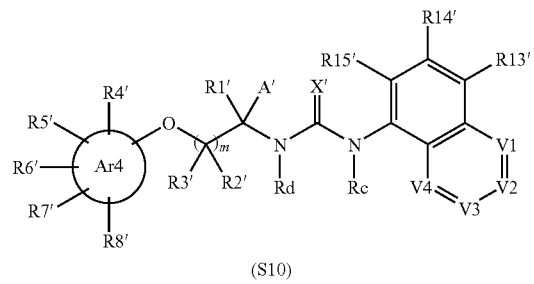

(S10)

wherein R13"-R15", V1'-V4', Rc' and Rd' show R13'-R15', V1-V4, Rc and Rd, or groups convertible to R13'-R15', V1-V4, Rc and Rd in certain stages of synthesis; and other symbols are as defined above.

Carbamate (S8) can be synthesized by reacting aniline (S6) having desired substituent(s) with aryl chloroformate (S7) in a solvent such as tetrahydrofuran, dichloromethane and the like, in the presence of a suitable base such as triethylamine, saturated aqueous sodium hydrogen carbonate and the like. A compound of the formula (S10) wherein X' is an oxygen atom can be obtained by reacting the obtained (S8) with amine (S9) in a solvent such as dimethyl sulfoxide and the like, in the presence of a suitable base such as diisopropylethylamine and the like. A compound of the formula (S10) wherein X' is a sulfur atom can be obtained when aryl chlorothioformate is used instead of aryl chloroformate as (S7) in the above-mentioned reaction. When m=1, amine (S9) can be synthesized in the same manner as in (S4), when m>1, it can be synthesized in the same manner as in the synthesis of (S4) by using the corresponding aminoalcohol protected in a suitable form as a starting material.

Furthermore, compound (S13), which is an ether derivative (III) of the present invention wherein V5 is N—H, V6 is N—H and X' is N—CN or N—OH can be produced, for example, by the following method.

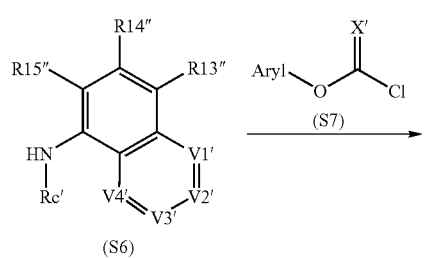

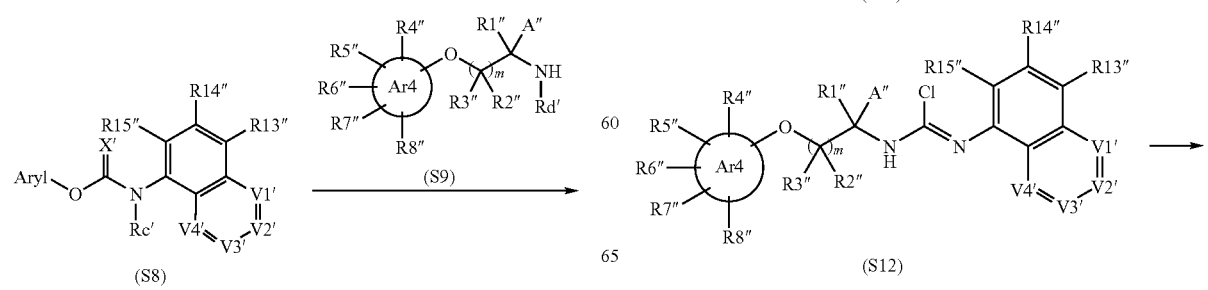

-continued

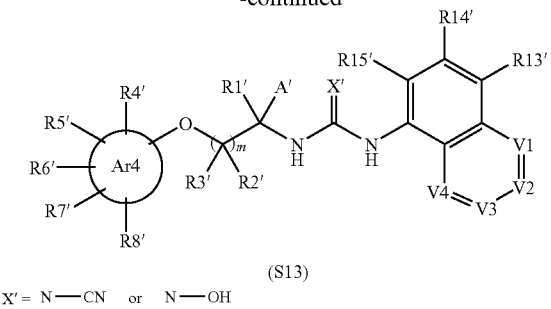

(S13)

X' = N—CN or N—OH (S11) obtained by the synthesis of (S10) wherein X'═O, RC═Rd═H is reacted with phosphoryl chloride and the like to give chloride (S12). The obtained (S12) is reacted with cyanamide in a solvent such as dichloromethane and the like, in the presence of a suitable base such as diisopropylethylamine and the like to give (S13) wherein X'═N—CN. (S13) wherein X'═N—OH can be obtained when hydroxylamine is used instead of cyanamide.

Compound (S15), which is an ether derivative (III) of the present invention wherein V1, V3 and V4 are each C—H, V2 is N→O, V5 is N-Rc and V6 is N-Rd can be produced, for example, by the following method.

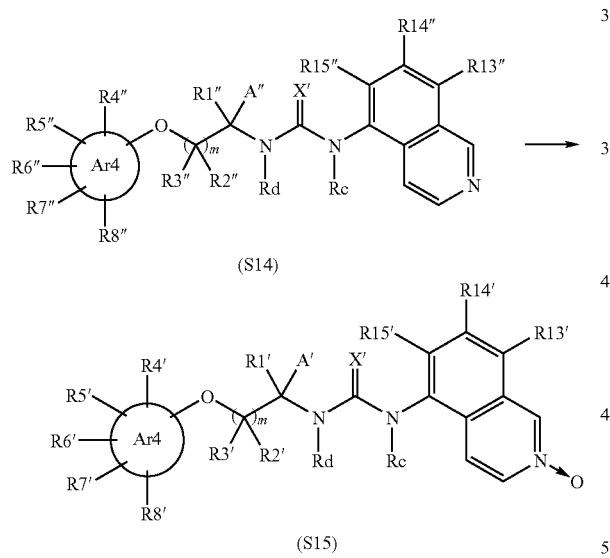

(S14) obtained by the synthesis of (S10) wherein V1═V3═V4═C—H, V2═N is reacted with an oxidant such as mCPBA and the like in a solvent such as dichloromethane and the like to give (S15).

It is also possible to synthesize a compound wherein V2, V3 and V4 are each C—H, and V1 is N→O using the corresponding starting material and according to a method similar to that of the synthesis of (S15).

A compound wherein R13' is $NH_2$, R14' and R15' are each a hydrogen atom, V1, V3 and V4 are each C—H, V2 is N, V5 is N-Rc, and V6 is N-Rd can be synthesized, for example, by the method shown in Example 134 or a method analogous thereto.

Various compounds of the present invention and intermediates thereof obtained by the above-mentioned production method can be converted to those having various substituents by further subjecting to the reactions such as alkylation, acylation, halogenation, nucleophilic substitution, reduction, oxidization and the like. The alkylation, acylation, halogenation, nucleophilic substitution, reduction and oxidization can be performed by, for example, the methods described in Zikken Kagaku Kouza (4th ed.), ed. The Chemical Society of Japan (1992) (Maruzen) and the like.

The representative examples of the present invention shown below can be synthesized in almost the same manner as in the above or adding methods obvious to those of ordinary skill in the art. In each structural formula, P1 is any of the substituents described in Tables 1 and 2, and P2 is any of the substituents described in Table 3. An optically active form of each structural formula is also encompassed. In the formula p-1, P2 shows a structural formula other than No. 73-No. 83.

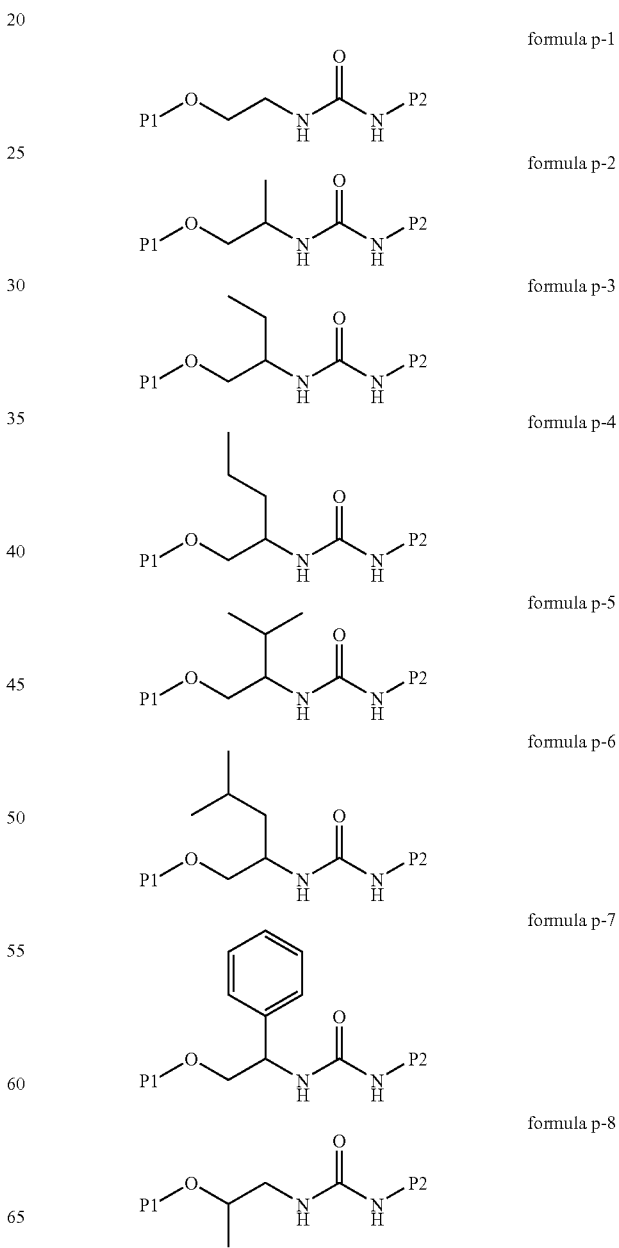

-continued
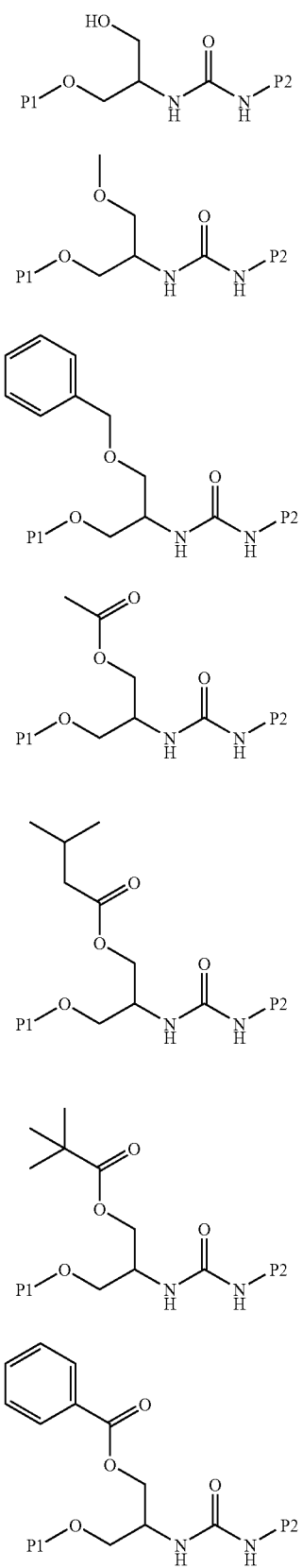
formula p-9
formula p-10
formula p-11
formula p-12
formula p-13
formula p-14
formula p-15
-continued
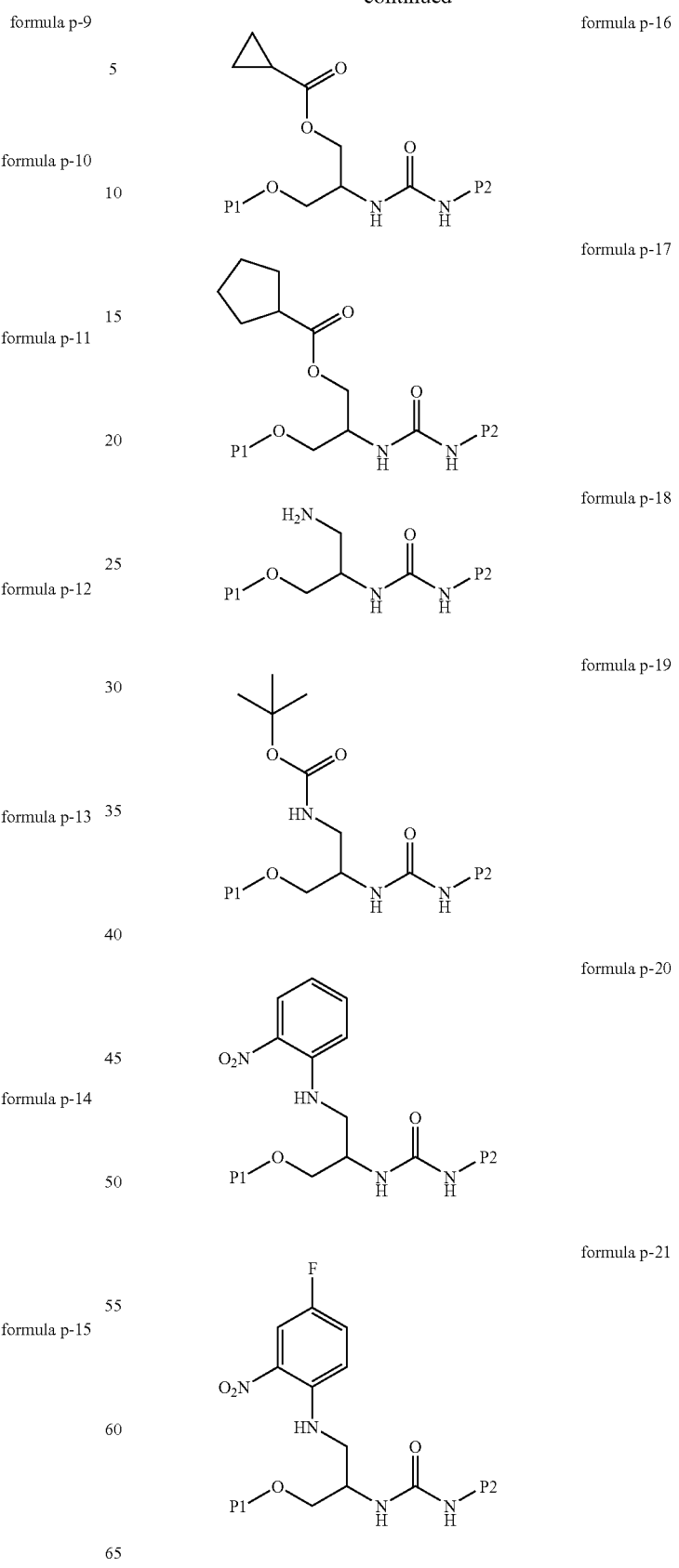
formula p-16
formula p-17
formula p-18
formula p-19
formula p-20
formula p-21

-continued
formula p-22
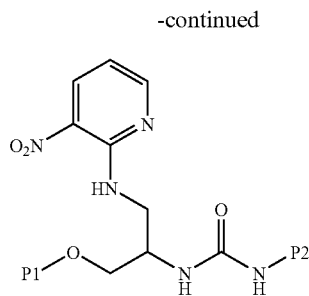
formula p-23
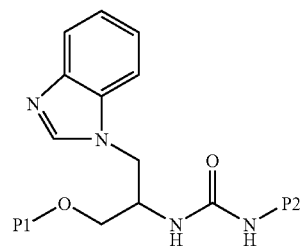
formula p-24
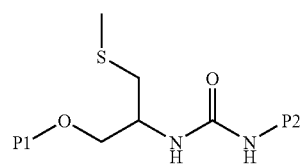
formula p-25
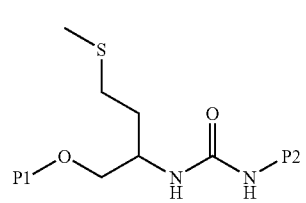
formula p-26
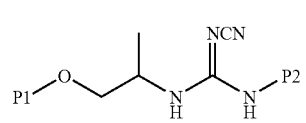
formula p-27
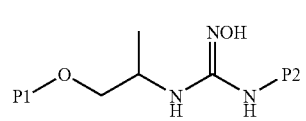
TABLE 1-continued
| No. | P1 |
|---|---|
| 1 | 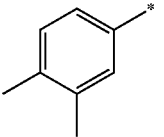 |
| 2 | 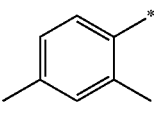 |
| 3 | 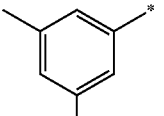 |
| 4 | 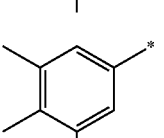 |
| 5 | 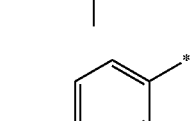 |
| 6 | 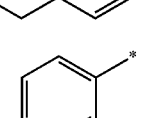 |
| 7 | 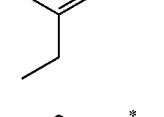 |
| 8 | 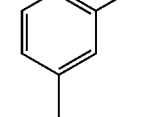 |
| 9 | 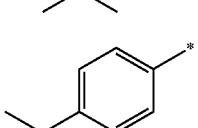 |
| 10 | 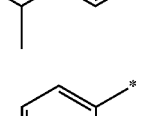 |
| 11 | 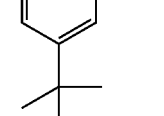 |
| 12 | 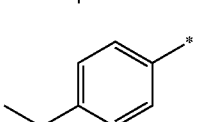 |

TABLE 1-continued

| No. | P1 |
|-----|----|
| 13 | 2,3-dihydro-1H-inden-5-yl |
| 14 | 5,6,7,8-tetrahydronaphthalen-2-yl |
| 15 | 3-fluoro-4-methylphenyl |
| 16 | 4-fluoro-3-methylphenyl |
| 17 | 4-chloro-3-methylphenyl |
| 18 | 2-fluorophenyl |
| 19 | 3-fluorophenyl |
| 20 | 4-fluorophenyl |
| 21 | 3-chlorophenyl |
| 22 | 4-chlorophenyl |
| 23 | 3-bromophenyl |
| 24 | 4-bromophenyl |
| 25 | 3-iodophenyl |
| 26 | 4-iodophenyl |
| 27 | 2,3-difluorophenyl |
| 28 | 2,4-difluorophenyl |
| 29 | 3,4-difluorophenyl |
| 30 | 3,5-difluorophenyl |
| 31 | 2,5-difluorophenyl |
| 32 | 2,4,5-trifluorophenyl |

TABLE 1-continued
| No. | P1 |
|---|---|
| 33 | 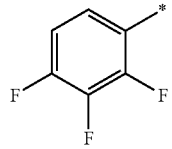 |
| 34 | 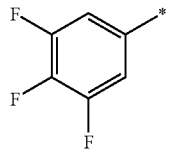 |
| 35 | 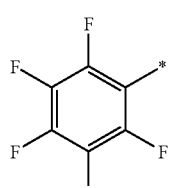 |
| 36 | 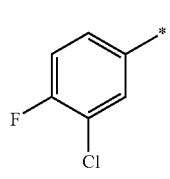 |
| 37 | 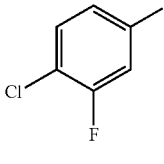 |
| 38 | 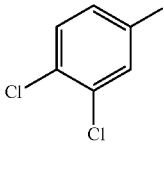 |
| 39 | 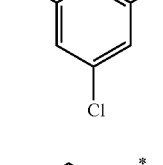 |
| 40 | 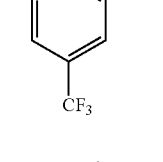 |
| 41 | 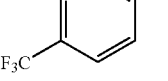 |
| 42 | 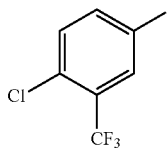 |
| 43 | 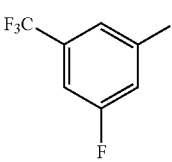 |
| 44 | 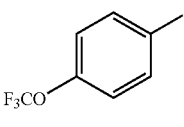 |
| 45 | 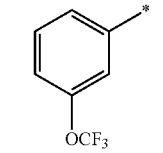 |
TABLE 2
| No. | P1 |
|---|---|
| 46 | 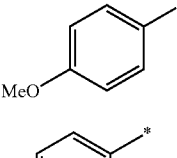 |
| 47 | 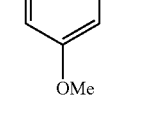 |
| 48 | 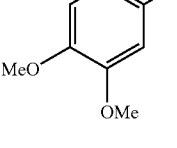 |
| 49 | 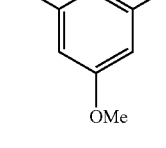 |
| 50 | 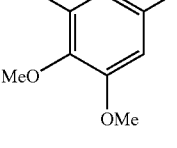 |

TABLE 2-continued
| No. | P1 |
|---|---|
| 51 | 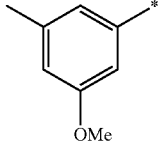 |
| 52 | 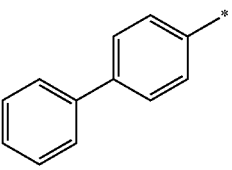 |
| 53 | 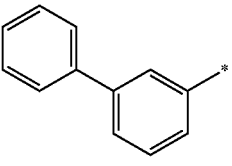 |
| 54 | 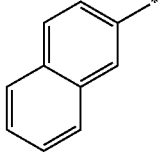 |
| 55 | 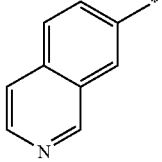 |
| 56 | 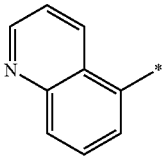 |
| 57 | 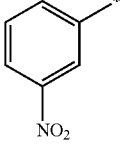 |
| 58 | 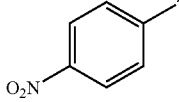 |
| 59 | 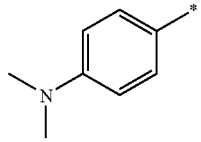 |
| 60 | 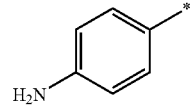 |
| 61 | 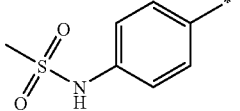 |
| 62 | 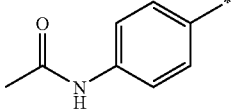 |
| 63 | 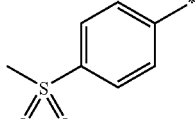 |
| 64 | 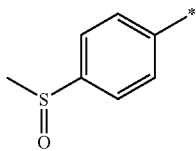 |
| 65 | |
| 66 | |
| 67 | |
| 68 | |
| 69 | |

TABLE 2-continued
| No. | P1 |
|---|---|
| 70 | 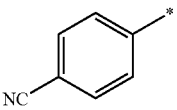 |
| 71 | 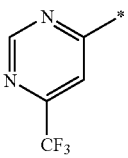 |
| 72 | 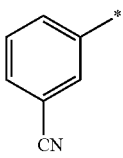 |
TABLE 3
| No. | P2 |
|---|---|
| 73 | 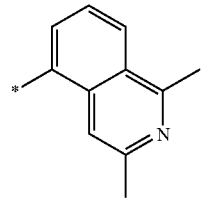 |
| 74 | 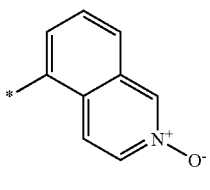 |
| 75 | 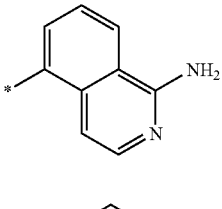 |
| 76 | 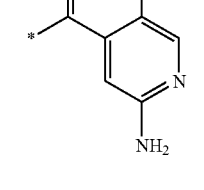 |
| 77 | 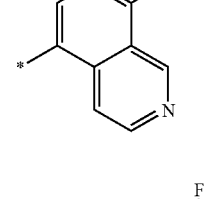 |
TABLE 3-continued
| No. | P2 |
|---|---|
| 78 | 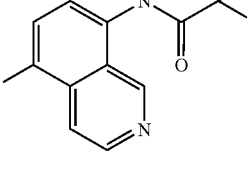 |
| 79 | 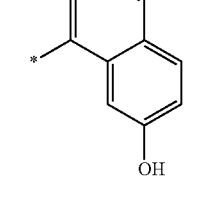 |
| 80 |  |
| 81 |  |
| 82 |  |
| 83 |  |
| 84 |  |

TABLE 3-continued

| No. | P2 |
|---|---|
| 85 | 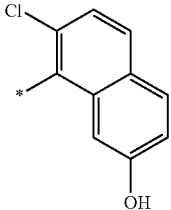 |

While the dose of the compound of the present invention varies depending on the kind of disease, pathology, age, administration route, compound and treatment period, it is generally 0.001-500 mg, preferably 0.001-1000 mg, more preferably 0.01-200 mg, per day for an adult by oral or parenteral (e.g., intravenous, subcutaneous, intramuscular, suppository, intestinal infusion, ointment, sublingual, instillation etc.) routes, which is administered once or in several portions.

The dose of the compound of the present invention is preferably 0.5 mg-5 g by oral administration and 1 μg-1 g by parenteral administration, for an adult.

The compound of the present invention is advantageously superior in the stability in acid or basic solution and can be applied, for example, to various dosage forms.

The compound of the present invention or a salt thereof can be administered as it is or in the form of a pharmaceutical composition containing various pharmaceutically acceptable carriers.

As the pharmaceutically acceptable carrier, various organic or inorganic carrier substances conventionally used as materials for pharmaceutical preparations can be mentioned. For example, excipient, lubricant, binder, disintegrant, water-soluble polymer and basic inorganic salt for solid preparations, solvent, dissolution aids, suspending agent, isotonicity agent, buffering agent and soothing agent for liquid preparations, and the like can be mentioned. Where necessary, conventional additives such as preservative, antioxidant, coloring agent, sweetening agent, souring agent, foaming agent, flavoring and the like can also be used.

As the dosage form of such pharmaceutical compositions, for example, tablet, powder, pill, granule, capsule, suppository, liquid, sugar-coated agent, depot, syrup, suspension, emulsion, troche, sublingual, adhesive agent, oral disintegrant (tablet), inhalant, intestinal infusion, plaster, tape and eye drop can be mentioned, which can be produced using ordinary preparation auxiliaries and by a conventional method.

The administration mode of the therapeutic agent of the present invention may be any of oral administration by solid preparation or liquid and parenteral administration by preparations such as subcutaneous, intramuscular or intravenous injection, adhesive agent, suppository, inhalant and the like. As the solid preparation, powder, granule, tablet, pill, capsule and the like and troche for internal application can be mentioned, and as the liquid, solution, syrup, emulsion, suspension and the like can be mentioned, all of which can be produced by methods known per se.

The therapeutic agent of the present invention is formulated into preparations by adding appropriate pharmaceutically acceptable vehicle, carrier, such as excipient, binder, lubricant, disintegrant, coating, solvent, dissolution aids, suspending agent, emulsifier, isotonicity agent and the like, as necessary for formulation of preparations. Where necessary, additives such as preservative, antioxidant, coloring agent, sweetening agent, flavor and the like can be added. The amount of the active ingredient in the composition or preparation is appropriately determined so that a suitable dose in the prescribed range can be achieved.

As the excipient, lactose, mannitol, glucose, hydroxypropylcellulose, micro crystalline cellulose, starch, polyvinylpyrrolidone, magnesium aluminometasilicate and the like can be mentioned, as the binder, pregelatinized starch, sucrose, gelatin, gum arabic, methylcellulose, carboxymethylcellulose, carboxymethylcellulose sodium, crystalline cellulose, sucrose, D-mannitol, trehalose, dextrin, hydroxypropylcellulose, hydroxypropylmethylcellulose, polyvinylpyrrolidone, polyvinyl alcohol and the like can be mentioned, as the lubricant, stearic acid, magnesium stearate, calcium stearate, talc, colloidal silica and the like can be mentioned, as the disintegrant, carboxymethylcellulose calcium, lactose, sucrose, starch, carboxymethylcellulose, croscarmellose sodium, sodium carboxymethyl starch, crystalline cellulose and the like can be mentioned, and as the coating, sucrose, gelatin, hydroxypropylcellulose, hydroxypropylmethylcellulose phthalate and the like can be mentioned.

As the solvent, hydrophilic solvents such as purified water, physiological brine, Ringer's solution, ethanol, propylene glycol, glycerol, polyethylene glycol, macrogol and the like, and oily solvents such as olive oil, peanut oil, sesame oil, camellia oil, rape seed oil, fatty acid monoglyceride, fatty acid diglyceride, higher fatty acid ester, liquid paraffin and the like can be mentioned, as the dissolution aids, polyethylene glycol, propylene glycol, D-mannitol, trehalose, benzyl benzoate, ethanol, sodium carbonate, sodium citrate, sodium salicylate, glutamic acid, aspartic acid and the like can be mentioned, as the suspending agent, sodium lauryl sulfate, lecithin, glyceryl monostearate, polyvinyl alcohol, polyvinyl pyrrolidone, carboxymethylcellulose sodium, methylcellulose, hydroxymethylcellulose, hydroxyethylcellulose, hydroxypropylcellulose, polysorbates, polyoxyethylene hydrogenated castor oil, gum arabic, bentonite and the like can be mentioned, as the emulsifier, gum arabic, gelatin, lecithin, egg yolk, cetanol, glyceryl monostearate, methylcellulose, carboxymethylcellulose sodium, stearic acid and the like can be mentioned, and as the isotonicity agent, sodium chloride, potassium chloride, glucose, fructose, mannitol, sorbitol, lactose, saccharose, glycerol, urea and the like can be mentioned.

As the preservative, paraoxybenzoates, chlorobutanol, benzyl alcohol, phenethyl alcohol, dehydroacetic acid, sorbic acid and the like can be mentioned, and as the antioxidant, sulfite, ascorbic acid and the like can be mentioned.

Any other pharmaceutical additive can be used for the production of the therapeutic agent of the present invention, and a sustained-release preparation can be prepared on demand.

The pharmaceutical preparation of the present invention can be formed into a package also containing a written matter explaining use of the pharmaceutical preparation.

The ether derivative of the present invention can be used concurrently with other analgesic, anti-inflammatory agent or therapeutic drug for each disease mentioned above. In this case, a concomitant drug may be contained in the same preparation with the ether derivative, or may be administered, as a separate preparation, simultaneously or with an appropriate time difference in association with each other.

EXAMPLES

The present invention is explained concretely and in detail in the following by referring to Examples, which are not to be construed as limitative. The structures of respective Examples are shown in Tables 8-31.

EXAMPLE

Example 1

N-(2-bromophenyl)-N'-[2-(4-fluorophenoxy)ethyl] urea

Step 1: t-butyl 2-bromoethylcarbamate

To 2-bromoethylamine hydrobromide (10 g) were added di-t-butyl dicarbonate (12.8 g), triethylamine (16.9 ml) and tetrahydrofuran (120 ml), and the mixture was stirred at room temperature for 15 hrs. The mixture was diluted with ethyl acetate. After washing with 1% aqueous $KHSO_4$ solution, the organic layer was dried over anhydrous sodium sulfate. The solvent was evaporated to give t-butyl 2-bromoethylcarbamate as a crude product (12.4 g).

Step 2: t-butyl 2-(4-fluorophenoxy)ethylcarbamate

To the crude product (700 mg) of t-butyl 2-bromoethylcarbamate obtained in Step 1 were added 4-fluorophenol (875 mg), potassium carbonate (1.08 g) and DMF (7 ml), and the mixture was stirred overnight at 90° C. The solvent was evaporated, and the mixture was diluted with ethyl acetate. After washing with water, the organic layer was dried over anhydrous sodium sulfate, and the solvent was evaporated. The obtained crude product was purified by silica gel chromatography (ethyl acetate-hexane) to give t-butyl 2-(4-fluorophenoxy)ethylcarbamate (390 mg).

Step 3: N-(2-bromophenyl)-N'-[2-(4-fluorophenoxy)ethyl] urea

To t-butyl 2-(4-fluorophenoxy)ethylcarbamate (190 mg) obtained in Step 2 was added 4N solution (3 ml) of hydrogen chloride in dioxane, and the mixture was stirred at room temperature for 4 hrs. The solvent was evaporated. To the obtained solid were added acetonitrile (4 ml), 2-bromophenyl isocyanate (109 µl) and triethylamine (405 µl), and the mixture was stirred overnight at room temperature. Water was added to the reaction mixture, and the precipitated solid was collected by filtration and dried to give N-(2-bromophenyl)-N'-[2-(4-fluorophenoxy)ethyl]urea (205 mg).

Examples 2-14

The compounds of Examples 2-14 were synthesized in the same manner as in the Steps of Example 1 except that 4-fluorophenol in Step 2 of Example 1 was changed to the corresponding various phenols and 2-bromophenyl isocyanate in Step 3 of Example 1 was changed to corresponding various isocyanates. In addition, derivatives having various substituents can be synthesized by known various exchange of substituents in each Steps in Example 1. The final compounds were purified by silica gel chromatography (hexane-ethyl acetate) or reversed-phase high performance liquid chromatography (reversed-phase HPLC) (water-acetonitrile, each containing 0.1% trifluoroacetic acid (TFA)).

Example 15

N-{(1S)-2-(benzyloxy)-1-[(3-methylphenoxy)methyl]ethyl}-N'-1-naphthyl urea

Step 1: t-butyl (1R)-2-(benzyloxy)-1-(hydroxymethyl)ethylcarbamate

O-benzyl-N-(t-butoxycarbonyl)-L-serine (2 g) was dissolved in tetrahydrofuran (20 ml), triethylamine (1.22 ml) was added, and ethyl chloroformate (713 µl) was further added dropwise at 0° C. After stirring the reaction mixture at room temperature for 30 min, the reaction mixture was filtered, and one piece of ice was added to the filtrate. Sodium borohydride (515 mg) was further added, and the mixture was stirred at room temperature for 6 hrs. The reaction mixture was diluted with ethyl acetate and, after washing with water, the organic layer was dried over anhydrous sodium sulfate. The solvent was evaporated and the obtained crude product was purified by silica gel chromatography (ethyl acetate-hexane) to give t-butyl (1R)-2-(benzyloxy)-1-(hydroxymethyl)ethylcarbamate (1.7 g)

Step 2: t-butyl (1S)-2-(benzyloxy)-1-[(3-methylphenoxy)methyl]ethylcarbamate

To t-butyl (1R)-2-(benzyloxy)-1-(hydroxymethyl)ethylcarbamate (3.23 g) obtained in Step 1 were added dichloromethane (40 ml), methanesulfonyl chloride (1.07 ml) and triethylamine (3.20 ml), and the mixture was stirred at 0° C. for 3 hrs. The reaction mixture was diluted with dichloromethane and, after washing with water, the organic layer was dried over anhydrous sodium sulfate. The solvent was evaporated to give a crude product. To this crude product were added dimethylformamide (30 ml) and lithium chloride (2.4 g), and the mixture was stirred overnight at 40° C. The solvent was evaporated, and the residue was diluted with ethyl acetate and washed with water. The organic layer was dried over anhydrous sodium sulfate, and the solvent was evaporated to give a crude product. To this crude product were added dimethylformamide (20 ml), potassium carbonate (2.4 g) and m-cresol (1.47 ml), and the mixture was stirred overnight at 90° C. The mixture was diluted with ethyl acetate and, after washing with water, the organic layer was dried over anhydrous sodium sulfate. The solvent was evaporated and the obtained crude product was purified by silica gel chromatography (ethyl acetate-hexane) to give t-butyl (1S)-2-(benzyloxy)-1-[(3-methylphenoxy)methyl]ethylcarbamate (1.5 g).

Step 3: N-{(1S)-2-(benzyloxy)-1-[(3-methylphenoxy)methyl]ethyl}-N'-1-naphthyl urea To t-butyl (1S)-2-(benzyloxy)-1-[(3-methylphenoxy)methyl]ethylcarbamate (60 mg) obtained in Step 2 was added 4N solution (2 ml) of hydrogen chloride in dioxane, and the mixture was stirred overnight at room temperature. The solvent was evaporated, acetonitrile (2 ml), 1-naphthyl isocyanate (32 µl) and triethylamine (85 µl) were added to the obtained solid, and the mixture was stirred at room temperature for 2 hrs. The reaction mixture was diluted with ethyl acetate and, after washing with water, the organic layer was dried over anhydrous sodium sulfate. The solvent was evaporated and the obtained crude product was purified by reversed-phase high performance liquid chromatography (reversed-phase HPLC) (water-acetonitrile, each containing 0.1% trifluoroacetic acid (TFA)) to give N-{(1S)-2-(benzyloxy)-1-[(3-methylphenoxy)methyl]ethyl}-N'-1-naphthyl urea (6.5 mg).

Example 16

N-{(1S)-2-(benzyloxy)-1-[(3-methylphenoxy)methyl]ethyl}-N'-2-bromophenyl urea

The compound of Example 16 was synthesized in the same manner as in the Steps of Example 15 except that 1-naphthyl isocyanate was changed to the corresponding isocyanate in Step 3 of Example 15.

Example 17

N-{(1R)-2-(benzyloxy)-1-[(3-methylphenoxy)methyl]ethyl}-N'-2-bromophenyl urea

The compound of Example 17 was obtained in the same manner as in Example 16 and using O-benzyl-N-(t-butoxycarbonyl)-D-serine as a starting material.

Example 18

N-(1-naphthyl)-N'-(1-phenylmethanesulfonylmethyl-2-m-tolyloxyethyl)urea

Step 1: (1-benzylsulfanylmethyl-2-hydroxyethyl)carbamic acid tert-butyl ester (1-Benzylsulfanylmethyl-2-hydroxyethyl)carbamic acid tert-butyl ester (7.5 g) was obtained in the same manner as in Step 1 of Example 15 and using S-benzyl-N-(t-butoxycarbonyl)-D-cysteine (10 g) as a starting material.

Step 2: (1-benzylsulfanylmethyl-2-m-tolyloxyethyl)carbamic acid tert-butyl ester (1-Benzylsulfanylmethyl-2-m-tolyloxyethyl)carbamic acid tert-butyl ester (3.0 g) was obtained in the same manner as in Step 2 of Example 15 and using (1-benzylsulfanylmethyl-2-hydroxyethyl)carbamic acid tert-butyl ester (4.8 g) obtained in Step 1 as a starting material.

Step 3: (1-phenylmethanesulfonylmethyl-2-m-tolyloxyethyl)carbamic acid tert-butyl ester To (1-benzylsulfanylmethyl-2-m-tolyloxyethyl)carbamic acid tert-butyl ester (500 mg) obtained in Step 2 were added dichloromethane (8 ml) and m-chloroperbenzoic acid (490 mg), and the mixture was stirred under ice-cooling for 3 hrs. The reaction mixture was diluted with dichloromethane and, after washing with 1N aqueous sodium hydroxide solution, the organic layer was dried over anhydrous sodium sulfate. The solvent was evaporated and the obtained crude product was purified by reversed-phase high performance liquid chromatography (reversed-phase HPLC) (water-acetonitrile, each containing 0.1% trifluoroacetic acid (TFA)) to give (1-phenylmethanesulfonylmethyl-2-m-tolyloxyethyl)carbamic acid tert-butyl ester (240 mg).

Step 4: N-(1-naphthyl)-N'-(1-phenylmethanesulfonylmethyl-2-m-tolyloxyethyl)urea

N-(1-Naphthyl)-N'-(1-phenylmethanesulfonylmethyl-2-m-tolyloxyethyl)urea (21 mg) was obtained in the same manner as in Step 3 of Example 15 and using (1-phenylmethanesulfonylmethyl-2-m-tolyloxyethyl)carbamic acid tert-butyl ester (80 mg) obtained in Step 3 as a starting material.

Example 19

N-(2-bromophenyl)-N'-(1-phenylmethanesulfonylmethyl-2-m-tolyloxyethyl)urea

The compound of Example 19 was synthesized in the same manner as in the Steps of Example 18 except that 1-naphthyl isocyanate was changed to the corresponding isocyanate in Step 4 of Example 18.

Example 20

N-[2-(3-naphthalen-1-yl-ureido)-3-m-tolyloxypropyl]benzamide

Step 1: (2-benzyloxycarbonylamino-3-hydroxypropyl)carbamic acid tert-butyl ester To N-(benzyloxycarbonyl)-DL-asparagine (7.5 g) were added ethyl acetate (36 ml), acetonitrile (36 ml), water (18 ml) and iodosobenzene diacetate (10 g), and the mixture was stirred overnight at room temperature. The reaction mixture was filtered and, after washing the obtained solid with ethyl acetate, dioxane (180 ml), water (40 ml), 1N aqueous sodium hydroxide solution (10 ml) and di-t-butyl dicarbonate (6.1 g) were added, and the mixture was stirred overnight at room temperature. The reaction mixture was diluted with ethyl acetate and washed with 0.5N hydrochloric acid. The solvent was evaporated to give 2-benzyloxycarbonylamino-3-tert-butoxycarbonylaminopropionic acid as a crude product. The crude product was treated in the same manner as in Step 1 of Example 15 to give (2-benzyloxycarbonylamino-3-hydroxypropyl)carbamic acid tert-butyl ester (2 g).

Step 2: (2-benzyloxycarbonylamino-3-m-tolyloxypropyl)carbamic acid tert-butyl ester (2-Benzyloxycarbonylamino-3-m-tolyloxypropyl)carbamic acid tert-butyl ester (4.8 g) was obtained in the same manner as in Step 2 of Example 15 and using (2-benzyloxycarbonylamino-3-hydroxypropyl)carbamic acid tert-butyl ester (6.5 g) obtained in Step 1 as a starting material.

Step 3: [1-(benzoylaminomethyl)-2-m-tolyloxyethyl]carbamic acid benzyl ester

To (2-benzyloxycarbonylamino-3-m-tolyloxypropyl)carbamic acid tert-butyl ester (220 mg) obtained in Step 2 was added 4N solution (2 ml) of hydrogen chloride in dioxane, and the mixture was stirred at room temperature for 1 hr. The solvent was evaporated, dichloromethane (7 ml), benzoyl chloride (96 µl) and triethylamine (265 µl) were added to the obtained solid, and the mixture was stirred at room temperature for 1 hr. The reaction mixture was diluted with ethyl acetate and, after washing with water, the organic layer was dried over anhydrous sodium sulfate. The solvent was evaporated and the obtained crude product was purified by silica gel chromatography (ethyl acetate-hexane) to give [1-(benzoylaminomethyl)-2-m-tolyloxyethyl]carbamic acid benzyl ester (200 mg).

Step 4: N-[2-(3-naphthalen-1-yl-ureido)-3-m-tolyloxypropyl]benzamide

To [1-(benzoylaminomethyl)-2-m-tolyloxyethyl]carbamic acid benzyl ester (70 mg) obtained in Step 3 were added 5% palladium-carbon (wet, 90 mg), ethanol (4 ml) and ethyl acetate (4 ml), and the mixture was stirred for 1 hr under hydrogen atmosphere. After celite filtration, the solvent was evaporated. Acetonitrile (3 ml) and 1-naphthyl isocyanate (85 µl) were added to the obtained crude product, and the mixture was stirred at room temperature for 2 hrs. The reaction mixture was diluted with ethyl acetate and, after washing with water, the organic layer was dried over anhydrous sodium sulfate. The solvent was evaporated and the obtained crude product was purified by reversed-phase high performance liquid chromatography (reversed-phase HPLC) (water-acetonitrile, each containing 0.1% trifluoroacetic acid (TFA)) to give N-[2-(3-naphthalen-1-yl-ureido)-3-m-tolyloxypropyl]benzamide (2.2 mg).

Example 21

N-[(1S)-2-(3-fluorophenoxy)-1-methylethyl]-N'-(isoquinolin-5-yl)urea TFA salt

Step 1: t-butyl (1S)-2-hydroxy-1-methylethylcarbamate

To L-alaninol (5 g) were added di-t-butyl dicarbonate (17 g), triethylamine (9 ml) and dichloromethane (100 ml), and the mixture was stirred at room temperature for 2 hrs. The mixture was diluted with dichloromethane and, after washing with water, the organic layer was dried over anhydrous magnesium sulfate. The solvent was evaporated and the obtained crude product was purified by silica gel chromatography (ethyl acetate-hexane) to give the title compound (5.9 g).

Step 2: (2S)-2-[(t-butoxycarbonyl)amino]propyl methanesulfonate

To the compound (5.9 g) obtained in Step 1 were added methanesulfonyl chloride (3.1 ml), triethylamine (9.0 ml) and dichloromethane (150 ml), and the mixture was stirred at 0° C. for 2 hrs. The mixture was diluted with dichloromethane and, after washing with water, the organic layer was dried over anhydrous magnesium sulfate. The solvent was evaporated to give the title compound as a crude product.

Step 3: t-butyl (1S)-2-chloro-1-methylethylcarbamate

To the crude product obtained in Step 2 were added lithium chloride (2.8 g) and dimethylformamide (100 ml), and the mixture was stirred overnight at 40° C. The mixture was diluted with ethyl acetate and, after washing with water, the organic layer was dried over anhydrous magnesium sulfate. The solvent was evaporated and the obtained crude product was purified by silica gel chromatography (ethyl acetate-hexane) to give the title compound (3.6 g).

Step 4: t-butyl (1S)-2-(3-fluorophenoxy)-1-methylethylcarbamate

To the compound (500 mg) obtained in Step 3 were added 3-fluorophenol (84 µl), potassium carbonate (250 mg) and DMF (2 ml), and the mixture was stirred overnight at 95° C. The reaction mixture was diluted with ethyl acetate. After washing with water, the organic layer was dried over anhydrous magnesium sulfate. The solvent was evaporated to give the title compound as a crude product.

Step 5: (2S)-1-(3-fluorophenoxy)-2-propylamine

To the crude product obtained in Step 4 was added 4N solution (2 ml) of hydrogen chloride in dioxane, and the mixture was stirred at room temperature for 2 hrs. After evaporation of the solvent, the residue was dissolved in ethyl acetate, and the mixture was washed with 1N hydrochloric acid. After basifying the aqueous layer with 1N aqueous sodium hydroxide, the mixture was extracted with ethyl acetate. The organic layer was dried over anhydrous magnesium sulfate. The solvent was evaporated to give the title compound as a crude product.

Step 6: phenyl isoquinolin-5-ylcarbamate

To 5-aminoisoquinoline (2.7 g) were added phenyl chloroformate (2.85 ml), pyridine (2.0 ml) and tetrahydrofuran (50 ml), and the mixture was stirred for 3 hrs. The reaction mixture was diluted with dichloromethane, and washed with water and saturated aqueous sodium hydrogen carbonate. The organic layer was dried over anhydrous sodium sulfate, and the solvent was evaporated. Diethyl ether was added to the residue, and the precipitate was collected by filtration to give the title compound (3 g).

Step 7: N-[(1S)-2-(3fluorophenoxy)-1-methylethyl]-N'-(isoquinolin-5-yl)urea TFA salt To the crude product (60 mg) obtained in Step 5 were added phenyl isoquinolin-5-ylcarbamate (64 mg), diisopropylethylamine (85 µl) and dimethyl sulfoxide (2 ml), and the mixture was stirred at room temperature for 2 hrs. The mixture was diluted with ethyl acetate. After washing with water, the organic layer was dried over anhydrous magnesium sulfate. The solvent was evaporated and the residue was purified by reversed-phase high performance liquid chromatography (reversed-phase HPLC) (water-acetonitrile, each containing 0.1% trifluoroacetic acid (TFA)) to give the title compound (18 mg).

Examples 22-81

Synthesis of Compounds of Examples 22-81

The compounds of Examples 22-81 were synthesized in the same manner as in Example 21 except that 3-fluorophenol was changed to the corresponding phenol in Step 4 of Example 21.

Example 82

N-[(1S)-2-(4-aminophenoxy)-1-methylethyl]-N'-(isoquinolin-5-yl)urea 2 TFA salt

To N-(isoquinolin-5-yl)-N'-[(1S)-1-methyl-2-(4-nitrophenoxy)ethyl]urea (4.7 mg) obtained in Example 45 were added ethanol (1 ml) and tin(II) chloride dihydrate (30 mg), and the mixture was stirred at 70° C. for 5 hrs. The reaction mixture was diluted with ethyl acetate. After washing with 1N aqueous sodium hydroxide solution, the organic layer was dried over magnesium sulfate, and the solvent was evaporated. The obtained residue was purified by reversed-phase high performance liquid chromatography (reversed-phase HPLC) (water-acetonitrile, each containing 0.1% trifluoroacetic acid (TFA)) to give N-[(1S)-2-(4-aminophenoxy)-1-methylethyl]-N'-(isoquinolin-5-yl)urea 2 TFA salt (1.7 mg).

Example 83

N-(isoquinolin-5-yl)-N'-{(1S)-2-[4-(dimethylamino)phenoxy]-1-methylethyl} urea 2 TFA salt To N-[(1S)-2-(4-aminophenoxy)-1-methylethyl]-N'-(isoquinolin-5-yl)urea (30 mg) obtained in Example 82 were added acetonitrile (3 ml), acetic acid (0.10 ml) and 37% aqueous formaldehyde solution (0.10 ml), and the mixture was stirred at room temperature for 30 min. Sodium triacetoxyborohydride (57 mg) was added to the reaction mixture, and the mixture was further stirred at room temperature for 30 min. The reaction mixture was diluted with ethyl acetate. After washing with 1N aqueous potassium hydroxide solution, the solvent was evaporated. The residue was purified by reversed-phase high performance liquid chromatography (reversed-phase HPLC) (water-acetonitrile, each containing 0.1% trifluoroacetic acid (TFA)) to give N-(isoquinolin-5- yl)-N'-{(1S)-2-[4-(dimethylamino)phenoxy]-1-methylethyl}urea 2 TFA salt (1.7 mg).

Example 84

N-{(1S)-2-[3-(dimethylamino)-4-nitrophenoxy]-1-methylethyl}-N'-(isoquinolin-5-yl)urea TFA salt The compound of Example 84 was synthesized in the same manner as in Example 21 except that 3-fluorophenol was changed to 3-fluoro-4-nitrophenol in Example 21.

Examples 85-108

Synthesis of Compounds of Examples 85-108

The compounds of Examples 85-108 were synthesized in the same manner as in Example 21 except that L-alaninol was changed to the corresponding aminoalcohol in Step 1 of Example 21 and 3-fluorophenol was changed to the corresponding phenol in Step 4 of Example 21.

Examples 109-115

The compounds of Examples 109-115 were synthesized by the operation similar to that in Steps 1-5 of Example 21 and Step 7 of Example 21 except that L-alaninol was changed to the corresponding aminoalcohol in Step 1 of Example 21, 3-fluorophenol was changed to the corresponding phenol in Step 4 of Example 21, and phenyl isoquinolin-5-ylcarbamate was changed to phenyl 7-hydroxy-1-naphthylcarbamate in Step 7 of Example 21. In addition, phenyl 7-hydroxy-1-naphthylcarbamate, was synthesized as shown below.

Synthesis of phenyl 7-hydroxy-1-naphthylcarbamate
To 8-amino-2-naphthol (100 mg) were added phenyl chloroformate (87 µl), saturated aqueous sodium hydrogen carbonate (0.5 ml), dichloromethane (1 ml) and water (0.5 ml), and the mixture was stirred for 3 hrs. The reaction mixture was diluted with dichloromethane. After washing with 1N hydrochloric acid, the organic layer was dried over anhydrous sodium sulfate, and the solvent was evaporated. Diethyl ether and hexane were added to the residue, and the precipitate was collected by filtration to give the title compound (160 mg). NMR data of Example 109: $^1$H-NMR (300 MHz, DMSO-$d_6$) δ3.49 (2H, m), 4.06 (2H, s), 6.79 (4H, m), 7.10 (2H, m), 7.30 (2H, m), 7.75 (2H, m), 8.34 (1H, s), 9.69 (1H, s).

Example 116

N-[(2R)-2-(3-fluorophenoxy)propyl]-N'-isoquinolin-5-yl)urea TFA salt

To (2R)-1-amino-2-propanol (1.25 g) were added di-t-butyl dicarbonate (9.5 g), triethylamine (6.9 ml) and dichloromethane (50 ml), and the mixture was stirred at room temperature for 2 hrs. The mixture was diluted with dichloromethane. After washing with water, the organic layer was dried over anhydrous sodium sulfate. The solvent was evaporated to give t-butyl (2R)-2-hydroxypropylcarbamate as a crude product. To the obtained crude product (1 g) were added methanesulfonyl chloride (533 µl), triethylamine (1.2 ml) and dichloromethane (15 ml), and the mixture was stirred at 0° C. for 1 hr. The mixture was diluted with dichloromethane. After washing with water, the organic layer was dried over anhydrous sodium sulfate. The solvent was evaporated to give (1R)-2-[(t-butoxycarbonyl)amino]-1-methylethyl methanesulfonate as a crude product. The entire amount of the obtained crude product was used for the following reaction. To the crude product were added lithium bromide (994 mg) and dimethylformamide (10 ml), and the mixture was stirred at 40° C. for 18 hrs. The mixture was diluted with ethyl acetate. After washing with water, the organic layer was dried over anhydrous sodium sulfate. The solvent was evaporated to give t-butyl (2S)-2-bromopropylcarbamate as a crude product. The half amount of the obtained crude product was used for the following reaction. To the crude product were added 3-fluorophenol (50 µl), potassium carbonate (150 mg) and DMF (2 ml), and the mixture was stirred overnight at 95° C. The mixture was diluted with ethyl acetate. After washing with water, the organic layer was dried over anhydrous sodium sulfate. The solvent was evaporated to give t-butyl (2R)-2-(3-fluorophenoxy)propylcarbamate as a crude product. The entire amount of the obtained crude product was used for the following reaction. 4N Solution (2 ml) of hydrogen chloride in dioxane was added to the crude product and, after stirring the mixture at room temperature for 2 hrs, the solvent was evaporated. To the residue were added phenyl isoquinolin-5-ylcarbamate (15 mg) obtained in Step 6 of Example 21, diisopropylethylamine (100 µl) and dimethyl sulfoxide (1 ml), and the mixture was stirred overnight at room temperature. The mixture was diluted with ethyl acetate. After washing with water, the organic layer was dried over anhydrous sodium sulfate. The solvent was evaporated and the residue was purified by reversed-phase high performance liquid chromatography (reversed-phase HPLC) (water-acetonitrile, each containing 0.1% trifluoroacetic acid (TFA)) to give the title compound (13 mg).

Example 117

Synthesis of Compound of Example 117

The compound of Example 117 was synthesized in the same manner as in Example 116 except that 3-fluorophenol was changed to the corresponding phenol in Example 116.

Example 118

N-(isoquinolin-5-yl)-N'-{(1S)-2-methoxy-1-[(3-methylphenoxy)methyl]ethyl}urea TFA salt Step 1: t-butyl (1S)-2-hydroxy-1-[(3-methylphenoxy)methyl]ethylcarbamate
To t-butyl (1S)-2-(benzyloxy)-1-[(3-methylphenoxy)methyl]ethylcarbamate (3.8 g) obtained in Step 2 of Example 15 were added 10% palladium-carbon (wet, 1 g) and ethanol (30 ml), and the mixture was stirred for 2 days under hydrogen atmosphere. After celite filtration, the solvent was evaporated. The obtained crude product was purified by silica gel chromatography (ethyl acetate-hexane) to give the title compound (3.0 g).

Step 2: N-(isoquinolin-5-yl)-N'-{(1S)-2-methoxy-1-[(3-methylphenoxy)methyl]ethyl}urea TFA salt
To (1S)-2-hydroxy-1-[(3-methylphenoxy)methyl]ethylcarbamic acid tert-butyl ester obtained in Step 1 were added benzene (1 ml), 50% aqueous sodium hydroxide solution (1 ml), methyl iodide (13 µl) and tetrabutylammonium hydrogen sulfate (12 mg), and the mixture was stirred overnight at room temperature. The reaction mixture was diluted with ethyl acetate and washed with water. The organic layer was dried over magnesium sulfate and the solvent was evaporated. To the obtained crude product was added 4N solution (2 ml) of hydrogen chloride in dioxane, and the mixture was stirred at room temperature for 2 hrs. The solvent was evaporated, dimethyl sulfoxide (1 ml), phenyl isoquinolin-5-ylcarbamate (50 mg) obtained in Step 6 of Example 21 and N,N-diisopropylethylamine. (0.35 ml) were added to the obtained solid, and the mixture was stirred overnight at room temperature. The reaction mixture was diluted with ethyl acetate. After washing with water, the solvent was evaporated. The obtained crude product was purified by reversed-phase high performance liquid chromatography (reversed-phase HPLC) (water-acetonitrile, each containing 0.1% trifluoroacetic acid (TFA)) to give N-(isoquinolin-5-yl)-N'-{(1S)-2-methoxy-1-[(3-methylphenoxy)methyl]ethyl} urea TFA salt (29 mg).

Example 119

N-{(1S)-2-hydroxy-1-[(3-methylphenoxy)methyl]ethyl}-N'-(isoquinolin-5-yl)urea TFA salt To (1S)-2-hydroxy-1-[(3-methylphenoxy)methyl]ethylcarbamic acid tert-butyl ester obtained Step 1 of Example 118 was added 4N solution (2 ml) of hydrogen chloride in dioxane, and the mixture was stirred at room temperature for 90 min. The solvent was evaporated, dimethyl sulfoxide (2 ml), phenyl isoquinolin-5-ylcarbamate (113 mg) obtained in Step 6 of Example 21, N,N-diisopropylethylamine (0.12 ml) were added to the obtained solid, and the mixture was stirred at room temperature for 2 hrs. The reaction mixture was diluted with ethyl acetate. After washing with water, the solvent was evaporated. The obtained crude product was purified by reversed-phase high performance liquid chromatography (reversed-phase HPLC) (water-acetonitrile, each containing 0.1% trifluoroacetic acid (TFA)) to give N-{(1S)-2-hydroxy-1-[(3-methylphenoxy)methyl]ethyl}-N'-(isoquinolin-5-yl)urea TFA salt (104 mg).

Example 120

N-{(1S)-2-acetoxy-1-[(3-methylphenoxy)methyl]ethyl}-N'-(isoquinolin-5-yl)urea TFA salt To N-{(1S)-2-hydroxy-1-[(3-methylphenoxy)methyl]ethyl}-N'-(isoquinolin-5-yl)urea (15 mg) obtained in Example 119 were added pyridine (1 ml), acetyl chloride (6.1 μl) and 4-dimethylaminopyridine (1 mg), and the mixture was stirred at room temperature for 2.5 hrs. The reaction mixture was diluted with ethyl acetate and washed with water. The organic layer was dried over magnesium sulfate, and the solvent was evaporated. The obtained crude product was purified by reversed-phase high performance liquid chromatography (reversed-phase HPLC) (water-acetonitrile, each containing 0.1% trifluoroacetic acid (TFA)) to give N-{(1S)-2-acetoxy-1-[(3-methylphenoxy)methyl]ethyl}-N'-(isoquinolin-5-yl)urea TFA salt (3.0 mg).

Examples 121-125

Synthesis of Compounds of Examples 121-125

The compounds of Examples 121-125 were synthesized in the same manner as in Example 120 except that acetyl chloride was changed to the corresponding acid chloride in Example 120.

Example 126 t-butyl (2S)-3-(3-fluorophenoxy)-2-{[(isoquinolin-5-ylamino)carbonyl]amino}propylcarbamate TFA salt Step 1: (2S)-3-amino-2-{[(benzyloxy)carbonyl]amino}propionic acid To N-(benzyloxycarbonyl)-L-asparagine (7.5 g) were added ethyl acetate (36 ml), acetonitrile (36 ml), water (18 ml) and iodosobenzene diacetate (10 g), and the mixture was stirred overnight at room temperature. The reaction mixture was filtered, and the obtained solid was washed with ethyl acetate to give the title compound.

Step 2: methyl (2S)-3-amino-2-{[(benzyloxy)carbonyl]amino}propanoate hydrochloride To the compound obtained in Step 1 were added methanol (100 ml) and thionyl chloride (2.4 ml), and the mixture was stirred overnight at room temperature. The solvent was evaporated to give the title compound as a crude product.

Step 3: methyl (2S)-2-{[(benzyloxy)carbonyl]amino}-3-[(t-butoxycarbonyl)amino]propanoate To the compound obtained in Step 2 were added di-t-butyl dicarbonate (9.2 g), triethylamine (12 ml) and tetrahydrofuran (100 ml), and the mixture was stirred overnight at room temperature. The solvent was evaporated and ethyl acetate was added to the residue. After washing with water, the organic layer was dried over anhydrous sodium sulfate. The solvent was evaporated to give the title compound as a crude product.

Step 4: (2S)-(2-benzyloxycarbonylamino-3-hydroxypropyl)carbamic acid tert-butyl ester To the compound obtained in Step 3 were added 2M solution (24 ml) of lithium borohydride in tetrahydrofuran and tetrahydrofuran (100 ml), and the mixture was stirred at 0° C. for 1 hr. Water was added to the reaction mixture, and the mixture was diluted with ethyl acetate. After washing with water and 1N hydrochloric acid, the organic layer was dried over anhydrous sodium sulfate. The solvent was evaporated and the obtained crude product was purified by silica gel chromatography (ethyl acetate-hexane) to give the title compound (7.0 g).

Step 5: (2S)-{2-benzyloxycarbonylamino-3-(3-fluorophenoxy)}carbamic acid tert-butyl ester The title compound (1.4 g) was obtained in the same manner as in Step 2 of Example 15 except that the compound (2 g) obtained in Step 4 was used as a starting material and m-cresol was changed to 3-fluorophenol in Step 2 of Example 15.

Step 6: t-butyl (2S)-2-amino-3-(3-fluorophenoxy)propylcarbamate

To the compound (1.4 g) obtained in Step 5 were added 10% palladium-carbon (wet, 200 mg) and ethyl acetate (15 ml), and the mixture was stirred for 1 hr under hydrogen atmosphere. After celite filtration, the solvent was evaporated to give the title compound as a crude product.

Step 7: t-butyl (2S)-3-(3-fluorophenoxy)-2-{[(isoquinolin-5-ylamino)carbonyl]amino}propylcarbamate TFA salt To the crude product obtained in Step 6 were added phenyl isoquinolin-5-ylcarbamate (1.1 g), diisopropylethylamine (1.2 ml) and dimethyl sulfoxide (15 ml), and the mixture was stirred overnight. The mixture was diluted with ethyl acetate. After washing with water, the organic layer was dried over anhydrous sodium sulfate. The solvent was evaporated and the residue was purified by silica gel chromatography (ethyl acetate-hexane) and a part thereof was purified by reversed-phase high performance liquid chromatography (reversed-phase HPLC) (water-acetonitrile, each containing 0.1% trifluoroacetic acid (TFA)) to give the title compound (27 mg).

Example 127

N-{(1R)-2-amino-1-[(3-fluorophenoxy)methyl]ethyl}-N'isoquinolin-5-yl)urea 2 TFA salt Step 1: t-butyl (2R)-3-(3-fluorophenoxy)-2-{[(isoquinolin-5-ylamino)carbonyl]amino}propylcarbamate The title compound was obtained in Steps 1-7 of Example 126 except that N-(benzyloxycarbonyl)-L-asparagine was changed to N-(benzyloxycarbonyl)-D-asparagine in Step 1 of Example 126.

Step 2: N-{(1R)-2-amino-1-[(3-fluorophenoxy)methyl]ethyl}-N'-(isoquinolin-5-yl)urea 2 TFA salt To t-butyl (2R)-3-(3-fluorophenoxy)-2-{[(isoquinolin-5-ylamino)carbonyl]amino}propylcarbamate (10 mg) obtained in Step 1 was added 4N solution (2 ml) of hydrogen chloride in dioxane, and the mixture was stirred at room temperature for 90 min. The solvent was evaporated and the obtained solid was purified by reversed-phase high performance liquid chromatography (reversed-phase HPLC) (water-acetonitrile, each containing 0.1% trifluoroacetic acid (TFA)) to give the title compound (10 mg).

Examples 128/129

N-(isoquinolin-5-yl)-N'-{(1S)-1-[(4-methylphenoxy)methyl]-3-(methylthio)propyl}urea TFA salt and
N-(isoquinolin-5-yl)-N'-[(1S)-3-(4-methylphenoxy)-1-(methylthiomethyl)propyl]urea TFA salt Step 1: (1S)-1-chloromethyl-3-(methylthio)propylcarbamic acid tert-butyl ester To (S)-(−)-methioninol (0.46 ml) were added di-t-butyl dicarbonate (0.88 g), triethylamine (0.77 ml) and dichloromethane (10 ml), and the mixture was stirred at room temperature for 24 hrs. Thereto were added methanesulfonyl chloride (0.34 ml) and triethylamine (1.0 ml), and the mixture was further stirred for 2 hrs. The reaction mixture was diluted with dichloromethane. After washing with water, the organic layer was dried over anhydrous magnesium sulfate. The solvent was evaporated to give a crude product. To this crude product were added dimethylformamide (10 ml) and lithium chloride (0.47 g), and the mixture was stirred overnight at 45° C. The solvent was evaporated, and the residue was diluted with ethyl acetate and washed with water. The organic layer was dried over anhydrous magnesium sulfate, and the solvent was evaporated to give (1S)-1-chloromethyl-3-(methylthio)propylcarbamic acid tert-butyl ester as a crude product (0.6 g).

Step 2: N-(isoquinolin-5-yl)-N'-{(1S)-1-[(4-methylphenoxy)methyl]-3-(methylthio)propyl}urea TFA salt and N-(isoquinolin-5-yl)-N'-[(1S)-3-(4-methylphenoxy)-1-(methylthiomethyl)propyl]urea TFA salt To the crude product (0.15 g) of (1S)-1-chloromethyl-3-(methylthio)propylcarbamic acid tert-butyl ester obtained in Step 1 were added dimethylformamide (5 ml), potassium carbonate (0.12 g) and p-cresol (0.17 ml), and the mixture was stirred overnight at 90° C. Then, the mixture was diluted with ethyl acetate. After washing with water, the organic layer was dried over anhydrous magnesium sulfate, and the solvent was evaporated. 4N Solution (2 ml) of hydrogen chloride in dioxane was added to the obtained crude product, and the mixture was stirred at room temperature for 4 hrs. The solvent was evaporated, and dimethyl sulfoxide (1 ml), phenyl isoquinolin-5-ylcarbamate (90 mg) obtained in Step 6 of Example 21 and N,N-diisopropylethylamine (0.3 ml) were added to the obtained solid, and the mixture was stirred at room temperature for 1 hr. The reaction mixture was diluted with ethyl acetate. After washing with water, the solvent was evaporated. The obtained crude product was purified by reversed-phase high performance liquid chromatography (reversed-phase HPLC) (water-acetonitrile, each containing 0.1% trifluoroacetic acid (TFA)) to give N-(isoquinolin-5-yl)-N'-{(1S)-1-[(4-methylphenoxy)methyl]-3-(methylthio)propyl}urea TFA salt (4.4 mg) and N-(isoquinolin-5-yl)-N'-[(1S)-3-(4-methylphenoxy)-1-(methylthiomethyl)propyl]urea TFA salt (7.1 mg), respectively.

Example 128 $^1$H-NMR (300 MHz, DMSO-$d_6$) δ1.91 (2H, m), 2.12 (3H, s), 2.19 (3H, s), 2.72 (2H, d, J=6.5 Hz), 4.01 (1H, t, J=6.0 Hz), 4.05 (1H, m), 6.75 (1H, d, J=9.2 Hz), 6.81 (2H, d, J=9.4 Hz), 7.03 (2H, d, J=9.4 Hz), 7.75 (1H, dd, J=8.8, 8.8 Hz), 7.95 (1H, d, J=8.8 Hz), 8.19 (1H, d, J=6.8 Hz), 8.41 (1H, d, J=8.8 Hz), 8.60 (1H, d, J=6.8 Hz), 8.88 (1H, s), 9.53 (1H, s).

Example 129 $^1$H-NMR (300 MHz, DMSO-$d_6$) δ1.91 (2H, m), 2.06 (3H, s), 2.20 (3H, s), 2.56 (2H, m), 3.95 (1H, dd, J=5.8, 9.4 Hz), 4.02 (1H, dd, J=5.5, 9.4 Hz), 4.13 (1H, m), 6.88 (2H, d, J=8.8 Hz), 6.90 (1H, d, J=8.5 Hz), 7.07 (2H, d, J=8.8 Hz), 7.78 (1H, dd, J=7.6, 7.6 Hz), 7.94 (1H, d, J=7.6 Hz), 8.22 (1H, d, J=6.4 Hz), 8.47 (1H, d, J=7.6 Hz), 8.61 (1H, d, J=6.4 Hz), 8.93 (1H, s), 9.57 (1H, s).

Example 130

Synthesis of Compound of Example 130

The compound of Example 130 was synthesized in the same manner as in Example 129 except that p-cresol was changed to the corresponding phenol in Step 2 of Example 129.

Example 131

N-{(1R)-2-(3-fluorophenoxy)-1-[(methylsulfanyl)methyl]ethyl}-N'-(isoquinolin-5-yl)urea TFA salt Step 1: t-butyl (1R)-2-hydroxy-1-[(methylsulfanyl)methyl]ethylcarbamate By the operation similar to that in Steps 2-4 of Example 126 and using S-methyl-L-cysteine as a starting material, the title compound (8 g) was obtained.

Step 2: t-butyl (1R)-2-(3-fluorophenoxy)-1-[(methylsulfanyl)methyl]ethylcarbamate By the operation similar to that in Step 2 of Example 15 except that t-butyl (1R)-2-hydroxy-1-[(methylsulfanyl)methyl]ethylcarbamate (1 g) obtained in Step 1 was used as a starting material and m-cresol was changed to 3-fluorophenol, the title compound (300 mg) was obtained.

Step 3: N-{(1R)-2-(3-fluorophenoxy)-1-[(methylsulfanyl)methyl]ethyl}-N'-(isoquinolin-5-yl)urea TFA salt By the operation similar to that in Steps 5-7 of Example 21 and using t-butyl (1R)-2-(3-fluorophenoxy)-1-[(methylsulfanyl)methyl]ethylcarbamate (15 mg) obtained in Step 2 as a starting material, the title compound (13 mg) was obtained.

Example 132

Synthesis of Compound of Example 132

The compound of Example 132 was synthesized in the same manner as in Example 131 except that 3-fluorophenol was changed to the corresponding phenol in Step 2 of Example 131.

Example 133

N-(isoquinolin-5-yl)-N'-[2-(3-chlorophenoxy)-1-methylethyl]urea-N"-oxide

To N-(isoquinolin-5-yl)-N'-[2-(3-chlorophenoxy)-1-methylethyl]urea (25 mg) obtained in Example 38 were added dichloromethane (1 ml) and m-chloroperbenzoic acid (18 mg) and the mixture was stirred at room temperature for 7 hrs. The reaction mixture was diluted with dichloromethane, and washed with 1N aqueous sodium hydroxide solution containing 20% sodium thiosulfate. The organic layer was dried over anhydrous magnesium sulfate, and the solvent was evaporated. The obtained crude product was purified by reversed-phase high performance liquid chromatography (reversed-phase HPLC) (water-acetonitrile, each containing 0.1% trifluoroacetic acid (TFA)) to give N-(isoquinolin-5-yl)-N'-[2-(3-chlorophenoxy)-1-methylethyl]urea-N"-oxide (1.0 mg).

Example 134

N-(8-aminoisoquinolin-5-yl)-N'-[2-(3,5-difluorophenoxy)-1-methylethyl]urea 2 TFA salt Step 1: 8-amino-5-nitroisoquinoline To 5-nitroisoquinoline (2.0 g) were added hydroxylamine hydrochloride (5.0 g) and ethanol (120 ml). A solution of sodium hydroxide (10 g) in methanol (65 ml) was slowly added at 50° C. over 90 min. The reaction mixture was poured into ice water (700 g) and the resulting precipitate was collected by filtration. The residue was washed with ethanol and dried under reduced pressure to give 8-amino-5-nitroisoquinoline (1.25 g).

Step 2: N-(5-nitroisoquinolin-8-yl)trifluoroacetamide

To 8-amino-5-nitroisoquinoline (0.92 g) were added dichloromethane (30 ml), triethylamine (1.0 ml) and trifluoroacetic anhydride (0.83 ml), and the mixture was stirred at room temperature for 1 hr. The reaction mixture was diluted with dichloromethane, and washed with water. The organic layer was dried over anhydrous magnesium sulfate, and the solvent was evaporated. The obtained residue was washed with diethyl ether containing a small amount of ethyl acetate and dried under reduced pressure to give N-(5-nitroisoquinolin-8-yl)trifluoroacetamide (1.1 g).

Step 3: 8-(trifluoroacetylamino)isoquinolin-5-ylcarbamic acid phenyl ester

To N-(5-nitroisoquinolin-8-yl)trifluoroacetamide (200 mg) were added ethyl acetate (15 ml) and 5% palladium-carbon (wet, 20 mg) and the mixture was stirred at room temperature under hydrogen atmosphere for 1 hr. Tetrahydrofuran was added to the reaction mixture to dissolve the resultant crystals, and palladium catalyst was removed by celite filtration. The solvent was evaporated from the filtrate to give N-(5-aminoisoquinolin-8-yl)trifluoroacetamide as a crude product. Tetrahydrofuran (12 ml), pyridine (62 µl) and phenyl chloroformate (0.10 ml) were added to the obtained crude product, and the mixture was stirred at room temperature for 15 min. The reaction mixture was diluted with dichloromethane, and washed twice with saturated aqueous sodium hydrogen carbonate. The organic layer was dried over anhydrous magnesium sulfate, and the solvent was evaporated. The residue was washed with diethyl ether and dried under reduced pressure to give 8-(trifluoroacetylamino)isoquinolin-5-ylcarbamic acid phenyl ester (194 mg).

Step 4: N-[2-(3,5-difluorophenoxy)-1-methylethyl]-N'-[8-(trifluoroacetylamino)isoquinolin-5-yl]urea To 8-(trifluoroacetylamino)isoquinolin-5-ylcarbamic acid phenyl ester (35 mg) were added 2-(3,5-difluorophenoxy)-1-methylethylamine hydrochloride (22 mg) obtained in Example 52 as a synthetic intermediate, dimethyl sulfoxide (1 ml) and N,N-diisopropylethylamine (81 µl), and the mixture was stirred at room temperature for 30 min. The reaction mixture was diluted with ethyl acetate and, after washing with water, the solvent was evaporated. The obtained crude product was purified by reversed-phase high performance liquid chromatography (reversed-phase HPLC) (water-acetonitrile, each containing 0.1% trifluoroacetic acid (TFA)) to give N-[2-(3,5-difluorophenoxy)-1-methylethyl]-N'-[8-(trifluoroacetylamino)isoquinolin-5-yl]urea TFA salt (13.7 mg).

Step 5: N-(8-aminoisoquinolin-5-yl)-N'-[2-(3,5-difluorophenoxy)-1-methylethyl]urea 2 TFA salt To N-[2-(3,5-difluorophenoxy)-1-methylethyl]-N'-[8-(trifluoroacetylamino)isoquinolin-5-yl]urea (12.6 mg) were added methanol (1 ml) and 1N aqueous sodium hydroxide solution (1 ml), and the mixture was stirred at room temperature for 4 days. Water was added to the reaction mixture, and the mixture was extracted three times with dichloromethane. The organic layer was dried over magnesium sulfate, and the solvent was evaporated. The obtained crude product was purified by reversed-phase high performance liquid chromatography (reversed-phase HPLC) (water-acetonitrile, each containing 0.1% trifluoroacetic acid (TFA)) to give N-(8-aminoisoquinolin-5-yl)-N'-[2-(3,5-difluorophenoxy)-1-methylethyl]urea 2 TFA salt (1.6 mg).

Example 135-142

Synthesis of Compounds of Examples 135-142

The compounds of Examples 135-142 were synthesized in the same manner as in Example 1 except that 4-fluorophenol was changed to the corresponding phenol in Step 2 of Example 1, and 2-bromophenyl isocyanate was changed to the corresponding isocyanate in Step 3 of Example 1.

Example 143

N-(2-bromophenyl)-N'-((1S)-2-(3-methylphenoxy)-1-{[(3-nitrobenzyl)oxy]methyl}ethyl)urea Step 1: t-butyl (1S)-2-(3-methylphenoxy)-1-{[(3-nitrobenzyl)oxy]methyl}ethylcarbamate To t-butyl (1S)-2-hydroxy-1-[(3-methylphenoxy)methyl]ethylcarbamate (300 mg) obtained in Step 1 of Example 118 were added 3-nitrobenzyl bromide (254 mg), tetrabutylammonium sulfate (91 mg), benzene (2.3 ml) and 50% aqueous sodium hydroxide solution (2.3 ml), and stirred at room temperature for 1.5 hrs. The mixture was diluted with ethyl acetate and, after washing with water, the organic layer was dried over anhydrous sodium sulfate. The solvent was evaporated and the obtained crude product was purified by silica gel chromatography (ethyl acetate-hexane) to give the title compound (340 mg).

Step 2: N-(2-bromophenyl)-N'-((1S)-2-(3-methylphenoxy)-1-{[(3-nitrobenzyl)oxy]methyl}ethyl)urea The title compound (20 mg) was obtained by a step similar to Step 3 of Example 1 and using t-butyl (1S)-2-(3-methylphenoxy)-1-{[(3-nitrobenzyl)oxy]methyl}ethylcarbamate (33 mg) obtained in Step 1 as a starting material, and then purification by reversed-phase high performance liquid chromatography (reversed-phase HPLC) (water-acetonitrile, each containing 0.1% trifluoroacetic acid (TFA)).

Example 144 and Examples 146-160

The compounds of Example 144 and Examples 146-160 were synthesized in the same manner as in Example 143 except that 3-nitrobenzyl bromide was changed to the corresponding benzyl bromide in Step 1 of Example 143 and 2-bromophenyl isocyanate was changed to the corresponding isocyanate in Step 2 of Example 143.

Example 145

Synthesis of Compound of Example 145

The compound of Example 145 was obtained by the operation similar to that in Step 6 of Example 126 except that the compound obtained in Example 144 was used as a starting material and the compound was purified by reversed-phase high performance liquid chromatography (reversed-phase HPLC) (water-acetonitrile, each containing 0.1% trifluoroacetic acid (TFA)).

Example 161-165

Synthesis of Compounds of Examples 161-165

The compounds of Examples 161-165 were synthesized in the same manner as in Example 15 except that m-cresol was changed to the corresponding phenol in Step 2 of Example 15 and 1-naphthyl isocyanate was changed to the corresponding isocyanate in Step 3 of Example 15.

Example 166-170

Synthesis of Compounds of Examples 166-170

The compounds of Examples 166-170 were synthesized by performing Steps 1-2 of Example 15 where m-cresol was changed to the corresponding phenol in Step 2 of Example 15 and successively performing the Step of Example 119.

Example 171-173

Synthesis of Compounds of Examples 171-173

The compounds of Examples 171-173 were synthesized by performing Steps 1-2 of Example 15 where m-cresol was changed to the corresponding phenol in Step 2 of Example 15 and successively performing the Step of Example 119 where phenyl isoquinolin-5-ylcarbamate was changed to the corresponding carbamate in Example 119. Phenyl 2-chloro-7-hydroxy-1-naphthylcarbamate necessary for the synthesis in Example 173 was synthesized by the synthetic method of phenyl 7-hydroxy-1-naphthylcarbamate shown for the synthesis of Example 109 except that the starting substance was 7-chloro-8-amino-2-naphthol.

Example 174

N-(2-bromophenyl)-N'-{2-(3-methylphenoxy)-1-[(2-nitroanilino)methyl]ethyl}urea

Step 1: benzyl 2-amino-1-[(3-methylphenoxy)methyl]ethylcarbamate

To the compound (200 mg) obtained in Step 2 of Example 20 was added 4N solution (2 ml) of hydrogen chloride in dioxane at room temperature and the mixture was stirred for 4 hrs. The solvent was evaporated, and the obtained solid was dissolved in ethyl acetate and washed with saturated aqueous sodium hydrogen carbonate. The organic layer was dried over anhydrous sodium sulfate, and the solvent was evaporated to give the title compound as a crude product.

Step 2: benzyl 2-(3-methylphenoxy)-1-[(2-nitroanilino)methyl]ethylcarbamate

To the crude product obtained in Step 1 were added 2-fluoronitrobenzene (102 µl) and dioxane (4 ml), and the mixture was stirred overnight at 90° C. The mixture was diluted with ethyl acetate, and washed with saturated aqueous sodium hydrogen carbonate. The organic layer was dried over anhydrous sodium sulfate, and the solvent was evaporated. The obtained crude product was purified by silica gel chromatography (ethyl acetate-hexane) to give the title compound.

Step 3: 3-(3-methylphenoxy)-$N^1$-(2-nitrophenyl)-1,2-propanediamine hydrobromide To the compound obtained in Step 2 were added 30% hydrobromide/acetic acid (1 ml) and dichloromethane (2 ml), and the mixture was stirred at 0° C. for 2 hrs. The mixture was diluted with dichloromethane, and washed with saturated aqueous sodium hydrogen carbonate. The organic layer was dried over anhydrous sodium sulfate and the solvent was evaporated to give the title compound as a crude product.

Step 4: N-(2-bromophenyl)-N'-{2-(3-methylphenoxy)-1-[(2-nitroanilino)methyl]ethyl}urea The compound obtained in Step 3 was treated in the same manner as in Step 3 of Example 1, and purified by reversed-phase high performance liquid chromatography (reversed-phase HPLC)(water-acetonitrile, each containing 0.1% trifluoroacetic acid (TFA)) to give the title compound (7 mg).

Example 175-181

Synthesis of Compounds of Examples 175-181

The compounds of Examples 175-181 were synthesized in the same manner as in the Step of Example 174 using, as a starting material, the compound synthesized by Steps 1-2 of Example 20 using N-benzyloxycarbonyl-DL-asparagine, N-benzyloxycarbonyl-L-asparagine or N-benzyloxycarbonyl-D-asparagine as a starting substance in Step 1 of Example 20, where 2-fluoronitrobenzene was changed to the corresponding aryl halide or heteroaryl halide in Step 2 of Example 174.

Example 182

N-{(1S)-2-(1H-benzimidazol-1-yl)-1-[(3-methylphenoxy)methyl]ethyl}-N'-(1-naphthyl)urea TFA salt Step 1: $N^1$-[(2S)-2-amino-3-(3-methylphenoxy)propyl]-1,2-benzenediamine Benzyl (1S)-2-(3-methylphenoxy)-1-[(2-nitroanilino)methyl]ethylcarbamate (1 g) obtained as a synthetic intermediate in Example 178 was treated in the same manner as in Step 6 of Example 126 to give the title compound (550 mg).

Step 2: t-butyl (1S)-2-(2-aminoanilino)-1-[(3-methylphenoxy)methyl]ethylcarbamate The compound obtained in Step 1 was treated in the same manner as in Step 1 of Example 21 to give the title compound (400 mg).

Step 3: t-butyl (1S)-2-(1H-benzimidazol-1-yl)-1-[(3-methylphenoxy)methyl]ethylcarbamate To the compound (85 mg) obtained in Step 2 were added methyl orthformate (1 ml) and acetic acid (50 μl), and the mixture was stirred at 60° C. for 1 hr. The mixture was diluted with ethyl acetate, and washed with 1N sodium hydroxide. The organic layer was dried over anhydrous magnesium sulfate, and the solvent was evaporated. The obtained crude product was purified by silica gel chromatography (ethyl acetate-hexane) to give the title compound (60 mg).

Step 4: N-{(1S)-2-(1H-benzimidazol-1-yl)-1-[(3-methylphenoxy)methyl]-ethyl}-N'-(1-naphthyl)urea TFA salt The compound obtained in Step 3 was treated as a starting material in the same manner as in Step 3 of Example 15 to give the title compound.

Examples 183-185

Synthesis of Compounds of Examples 183-185

The compounds of Examples 183-185 were synthesized in the same manner as in the Step of Example 179 except that m-cresol was changed to the corresponding phenol.

Example 186

N-(2-bromophenyl)-N'-[(1S)-2-(3-methylphenoxy)-1-(phenoxymethyl)ethyl]urea

Step 1: t-butyl (1S)-2-(3-methylphenoxy)-1-(phenoxymethyl)ethylcarbamate

The title compound (75 mg) was obtained by the similar treatment as in Step 2 of Example 15 except that compound obtained in Step 1 of Example 118 was used as a starting material and m-cresol was changed to phenol in Step 2 of Example 15.

Step 2: N-(2-bromophenyl)-N'-[(1S)-2-(3-methylphenoxy)-1-(phenoxymethyl)ethyl]urea The title compound (10 mg) was obtained by the similar treatment as in Step 3 of Example 1 except that the compound (75 mg) obtained in Step 1 was used as a starting material and the obtained crude product was purified by silica gel chromatography (ethyl acetate-hexane).

Example 187

Synthesis of Compound of Example 187

The compound of Example 187 was synthesized in the same manner as in the Step of Example 186 except that phenol was changed to the corresponding phenol.

Example 188

N-(2-bromophenyl)-N'-{(1S)-1-[(3-methylphenoxy)methyl]-3-phenoxypropyl}urea

Step 1: benzyl (3S)-2-oxotetrahydro-3-furanylcarbamate

To L-homoserine (2 g) were added sodium hydrogen carbonate (3.7 g) and water (30 ml), and the mixture was stirred at room temperature for 1 hr. To the reaction mixture were further added benzyl chloroformate (3.9 ml) and ether (10 ml), and the mixture was stirred at room temperature for 18 hrs. The reaction mixture was diluted with ethyl acetate and washed with 1N hydrochloric acid. The organic layer was dried over anhydrous sodium sulfate and the solvent was evaporated. The obtained crude product was purified by silica gel chromatography (ethyl acetate-hexane) to give the title compound (2.5 g).

Step 2: methyl(2S)-2-{[(benzyloxy)carbonyl]amino}-4-hydroxybutanoate

To the compound (500 mg) obtained in Step 1 were added methanol (5 ml) and conc. sulfuric acid (30 μl), and the mixture was stirred overnight at 60° C. To the reaction mixture was further added sodium hydrogen carbonate (250 mg), and the mixture was stirred at room temperature for 2 hrs. After celite filtration of the reaction mixture, the solvent was evaporated to give the title compound as a crude product.

Step 3: methyl(2S)-2-{[(benzyloxy)carbonyl]amino}-4-phenoxybutanoate

The compound obtained in Step 2 was treated in the same manner as in Step 2 of Example 15 except that m-cresol was changed to phenol in Step 2 of Example 15 to give the title compound (280 mg).

Step 4: benzyl (1S)-1-(hydroxymethyl)-3-phenoxypropylcarbamate

The compound obtained in Step 3 was treated in the same manner as in Step 4 of Example 126 to give the title compound (240 mg).

Step 5: benzyl (1S)-1-[(3-methylphenoxy)methyl]-3-phenoxypropylcarbamate

The compound obtained in Step 4 was treated in the same manner as in Step 2 of Example 15 to give the title compound (70 mg).

Step 6: (2S)-1-(3-methylphenoxy)-4-phenoxy-2-butanamine

The compound (23 mg) obtained in Step 5 was treated in the same manner as in Step 6 of Example 126 to give a crude product of the title compound.

Step 7: N-(2-bromophenyl)-N'-{(1S)-1-[(3-methylphenoxy)methyl]-3-phenoxypropyl}urea To the crude product obtained in Step 6 were added 2-bromophenyl isocyanate (15 μl) and acetonitrile (500 μl) and the mixture was stirred at room temperature for 14 hrs. The precipitated solid was collected by filtration and dried to give the title compound (26 mg).

Example 189

Synthesis of Compound of Example 189

The compound of Example 189 was synthesized in the same manner as in the Step of Example 188 except that 2-bromophenyl isocyanate was changed to the corresponding isocyanate in Step 7 of Example 188.

Example 190-191

Synthesis of Compounds of Examples 190-191

The compounds of Examples 190-191 were synthesized in the same manner as in the Step of Example 21 except that 3-fluorophenol was changed to the corresponding phenol in Example 21.

Example 192-199

Synthesis of Compounds of Examples 192-199

The compounds of Examples 192-199 were synthesized in the same manner as in Example 21 except that L-alaninol was changed to the corresponding aminoalcohol in Step 1 of Example 21, and 3-fluorophenol was changed to the corresponding phenol in Step 4 of Example 21.

Examples 200-205

Synthesis of Compounds of Examples 200-205

The compounds of Examples 200-205 were synthesized by the operation similar to that in Steps 1-5 of Example 21 and Step 7 of Example 21 except that L-alaninol was changed to the corresponding aminoalcohol in Step 1 of Example 21, 3-fluorophenol was changed to the corresponding phenol in Step 4 of Example 21, and phenyl isoquinolin-5-ylcarbamate was changed to phenyl 7-hydroxy-1-naphthylcarbamate in Step 7 of Example 21. In addition, phenyl 7-hydroxy-1-naphthylcarbamate was synthesized in the same manner as in Examples 109-115.

Example 206

Synthesis of Compound of Example 206

The compound of Example 206 was synthesized in the same manner as in Example 133 using, as a starting material, N-{(1S)-1-[(3,5-difluorophenoxy)methyl]butyl}-N'-(isoquinolin-5-yl)urea obtained in Example 205.

Examples 207-208

Synthesis of Compounds of Examples 207-208

The compounds of Examples 207-208 were synthesized in the same manner as in Example 134 except that, in Step 4 of Example 134, 2-(3,5-difluorophenoxy)-1-methylethylamine hydrochloride was changed to hydrochloride of the corresponding amine obtained as an intermediate in Example 51 and Example 91.

Example 209

Synthesis of Compound of Example 209

The compound of Example 209 was obtained by purifying the synthetic intermediate of Example 207 by reversed-phase high performance liquid chromatography (reversed-phase HPLC) (water-acetonitrile, each containing 0.1% trifluoroacetic acid (TFA)).

Example 210

N-(1-amino-isoquinolin-5-yl)-N'-{(1S)-1-[(3,4-difluorophenoxy)methyl]butyl}urea TFA salt The compound (400 mg) obtained in Example 96 was dissolved in dichloromethane (5 ml), m-chloroperbenzoic acid (215 mg) was added, and the mixture was stirred at room temperature for 2 hrs. The mixture was diluted with dichloromethane and, after washing with water, the organic layer was dried over anhydrous magnesium sulfate. The solvent was evaporated and the obtained crude product was purified by reversed-phase high performance liquid chromatography (reversed-phase HPLC)(water-acetonitrile, each containing 0.1% trifluoroacetic acid (TFA)). The obtained purified product (40 mg) was dissolved in dichloromethane (5 ml), pyridine (0.016 ml) and tosyl chloride (23 mg) were added, and the mixture was stirred at room temperature for 2 hrs. The solvent was evaporated, to the residue was added aminoethanol (2 ml), and the mixture was stirred at room temperature for 2 hrs. The mixture was diluted with ethyl acetate and, after washing with water, the organic layer was dried over anhydrous magnesium sulfate. The solvent was evaporated and the obtained crude product was purified by reversed-phase high performance liquid chromatography (reversed-phase HPLC) (water-acetonitrile, each containing 0.1% trifluoroacetic acid (TFA)) to give the title compound (5 mg).

Examples 211-212

Synthesis of Compounds of Examples 211-212

The compounds of Examples 211-212 were synthesized in the same manner as in the Step of Example 21 except that 3-fluorophenol was changed to the corresponding phenol in Step 4 of Example 21, and 5-aminoisoquinoline was changed to 5-aminoquinoline in Step 6 of Example 21.

Example 213

N-[(1S)-2-(3-chlorophenoxy)-1-methylethyl]-N''-cyano-N'-(isoquinolin-5-yl)guanidine TFA salt To N-[(1S)-2-(3-chlorophenoxy)-1- methylethyl]-N'-(isoquinolin-5-yl)urea (20 mg) obtained in Example 38 was added phosphorus oxychloride (2 ml), and the mixture was stirred at 75° C. for 1 hr. The solvent was evaporated, dichloromethane (2 ml), N,N-diisopropylethylamine (0.1 ml) and cyanamide (15 mg) were added to the obtained residue, and the mixture was stirred at room temperature for 1 hr. The solvent was evaporated and the obtained crude product was purified by reversed-phase high performance liquid chromatography (reversed-phase HPLC)(water-acetonitrile, each containing 0.1% trifluoroacetic acid (TFA)) to give the title compound (12 mg).

Example 214

The compound of Example 214 was synthesized in the same manner as in Example 213 except that the compound obtained in Example 96 was used as a starting material and cyanamide was changed to hydroxylamine hydrochloride.

Examples 215-222

Synthesis of Compounds of Examples 215-222

The compounds of Examples 215-222 were obtained by converting the compounds obtained in the corresponding Examples (Examples 38, 51, 52, 80, 91, 92, 94, 96) from TFA salt to hydrochloride by the following methods. Conversion from TFA salt to hydrochloride The TFA salt obtained in each Example was suspended in ethyl acetate and washed with saturated aqueous sodium hydrogen carbonate. The organic layer was dried over anhydrous sodium sulfate and the solvent was evaporated. A 4N solution of hydrogen chloride in dioxane was added to the obtained residue and the mixture was stirred for 30 min. The solvent was evaporated to give hydrochloride of each compound. NMR data of each compound:

Example 215 $^1$H-NMR (300 MHz, DMSO-$d_6$) $\delta$1.23 (3H, d), 4.02 (3H, m), 6.97 (1H, m), 7.07 (1H, d), 7.30 (3H, m), 7.90 (1H, dd), 8.06 (1H, d), 8.68 (3H, m), 9.54 (1H, s), 9.78 (1H, s).

Example 216 $^1$H-NMR (300 MHz, DMSO-$d_6$) $\delta$1.25 (3H, d), 3.98 (3H, m), 6.82 (1H, m), 7.14 (1H, m), 7.33 (2H, m), 7.88 (1H, dd), 8.05 (1H, d), 8.71 (1H, m), 9.57 (1H, s), 9.77 (1H, s).

Example 217 $^1$H-NMR (300 MHz, DMSO-$d_6$) $\delta$1.24 (3H, d), 3.98 (3H, m), 6.77 (1H, m), 7.32 (1H, d), 7.86 (1H, dd), 8.05 (1H, d), 8.62 (3H, m), 9.49 (1H, s), 9.76 (1H, s).

Example 218 $^1$H-NMR (300 MHz, DMSO-$d_6$) $\delta$1.23 (3H, d), 1.68 (4H, m), 2.62 (4H, m), 3.91 (3H, m), 6.66 (2H, m), 6.92 (1H, d), 7.29 (1H, d), 7.87 (1H, dd), 8.05 (1H, d), 8.65 (3H, m), 9.51 (1H, s), 9.78 (1H, s).

Example 219 $^1$H-NMR (300 MHz, DMSO-$d_6$) $\delta$0.97 (3H, t), 1.63 (2H, m), 4.00 (3H, m), 6.82 (1H, m), 7.13 (1H, m), 7.35 (2H, m), 7.86 (1H, dd), 8.04 (1H, d), 8.66 (2H, dd), 8.77 (1H, d), 9.61 (1H, s), 9.75 (1H, s).

Example 220 $^1$H-NMR (300 MHz, DMSO-$d_6$) $\delta$0.97 (3H, t), 1.63 (2H, m), 4.00 (3H, m), 7.00 (1H, m), 7.28 (3H, m), 8.03 (1H, d), 8.63 (2H, t), 8.77 (1H, d), 9.59 (1H, s), 9.74 (1H, s).

Example 221 $^1$H-NMR (300 MHz, DMSO-$d_6$) $\delta$0.91 (3H, t), 1.53 (4H, m), 4.01 (3H, m), 6.86 (3H, m), 7.31 (2H, m), 7.85 (1H, t), 8.04 (1H, d), 8.68 (3H, m), 9.55 (1H, s), 9.75 (1H, s).

Example 222 $^1$H-NMR (300 MHz, DMSO-$d_6$) $\delta$0.90 (3H, t), 1.55 (4H, m), 4.00 (3H, m), 6.91 (1H, m), 7.15 (1H, m), 7.31 (1H, dd), 7.42 (1H, d), 7.89 (1H, t), 8.06 (1H, d), 8.68 (2H, d), 8.83 (1H, d), 9.65 (1H, s), 9.79 (1H, s).

Examples 223-224

Synthesis of Compounds of Examples 223-224

The compounds of Examples 223-224 were synthesized by the operation similar to that in Steps 1-5 of Example 21 and Step 7 of Example 21 except that L-alaninol was changed to the corresponding aminoalcohol in Step 1 of Example 21, 3-fluorophenol was changed to the corresponding phenol in Step 4 of Example 21, and phenyl isoquinolin-5-ylcarbamate was changed to phenyl 2-chloro-7-hydroxy-1-naphthylcarbamate in Step 7 of Example 21. In addition, phenyl 2-chloro-7-hydroxy-1-naphthylcarbamate was synthesized in the same manner as in Example 173.

Experimental Example 1

Acetic Acid-induced Writhing Method

The effect of the test compound in the writhing test method induced by acetic acid was examined using male ICR mouse (4-week-old). For intraperitoneal administration of the test compound, the test compound was dissolved in saline containing 5% DMSO and 5% Tween 80 to a suitable concentration, and administered at a dose of 5 ml/kg at 30 min before acetic acid administration. For oral administration of the test compound, the test compound was suspended in 0.5% CMC and administered at a dose of 5 ml/kg at 1 hr before acetic acid administration. Acetic acid was diluted with saline to 0.9%, intraperitoneally administered at a dose of 5 ml/kg and, starting 5 min thereafter, the number of writhing responses was counted for 15 min. Saline containing 5% DMSO and 5% Tween 80 was also intraperitoneally administered to the control group (vehicle administration group). As the standard product, indomethacin was used, which was suspended in 0.5% tragacanth gum and orally administered at 90 min before acetic acid administration. 0.5% Tragacanth gum was administered to the control group.

Figure 2:
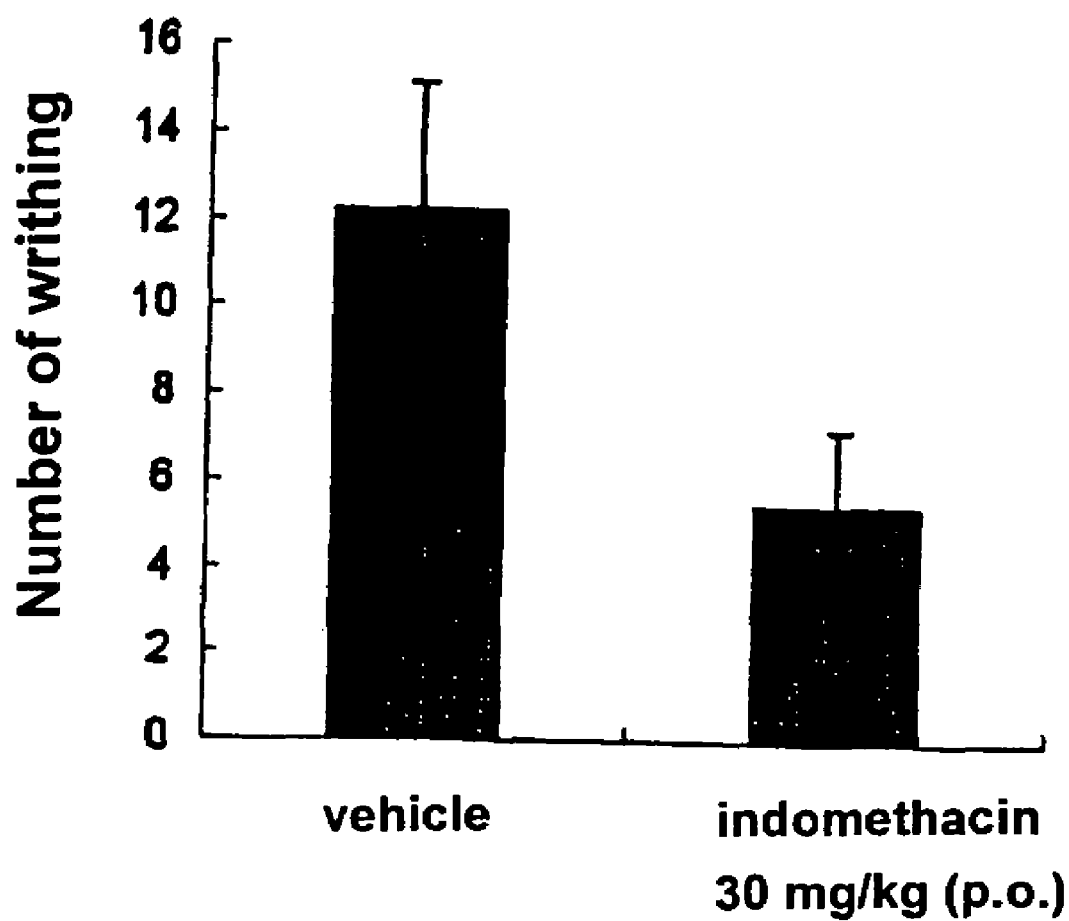
FIG. 2 shows the number of writhing in the acetic acid-induced writhing method when indomethacin was administered.

The number of writhing responses by each test compound is shown in FIG. 1 and the number of writhing responses by indomethacin is shown in FIG. 2.

The number of writhing responses of each compound administration group to the number of writhing responses is shown in Table 4 as inhibitory rate.

TABLE 4

| compound | dose (mg/kg) | administration route | inhibitory rate (%) |
|---|---|---|---|
| Example 1 | 10 | intraperitoneal | 76 |
| Example 122 | 10 | oral | 76 |
| indomethacin | 30 | oral | 56 |

Experimental Example 2

Carrageenin-induced Thermal Hyperalgesia Model Method

Male SD rats (6-8-week-old) were used. 2% Carrageenan (100 μl, dissolved in distilled water) was injected into the right hind paw, and a planter test was performed 3 hr later. The heat was irradiated on the right hind paw and the latency for nociceptive behavior was measured and used as an index. The compound was suspended in 0.5% CMC and orally administered at a dose of 5 ml/kg at 3 hr before the planter test. The inhibitory rate was calculated relative to the value measured before administration as 100%. The results are shown in Table 5.

TABLE 5

| compound | dose (mg/kg) | inhibitory rate (%) |
| --- | --- | --- |
| Example 70 | 3 | 92 |
| Example 192 | 1 | >100 |
| Example 201 | 30 | 70 |
| Example 217 | 10 | 88 |
| Example 218 | 10 | >100 |
| Example 219 | 10 | 64 |
| Example 220 | 10 | 63 |
| Example 222 | 10 | >100 |

| compound | $ED_{50}$ |
| --- | --- |
| Example 222 | 0.035 mg/kg |

Experimental Example 3

Mustard Oil-induced Thermal Hyperalgesia Model

Method

Male ICR mice (5 to 7-week-old) were used. Mustard oil 10% (diluted with distilled water) was subcutaneously injected into both hind paws, and a hot plate test was performed 30 min 10 later. The animal was placed on a hot plate and the latency for nociceptive behavior was measured and used as an index. The compound was suspended in 0.5% CMC and orally administered at a dose of 5 ml/kg at 1 hr before the hot plate test. The inhibitory rate was calculated relative to the index measured before administration as 100%. The results are shown in Table 6.

TABLE 6

| compound | dose (mg/kg) | inhibition rate (%) |
| --- | --- | --- |
| Example 38 | 1.0 | 57 |
| Example 80 | 1.0 | 72 |

Experimental Example 4

Dextran Sodium Sulfate-induced Enteritis Model (DSS Model)

Figure 3:
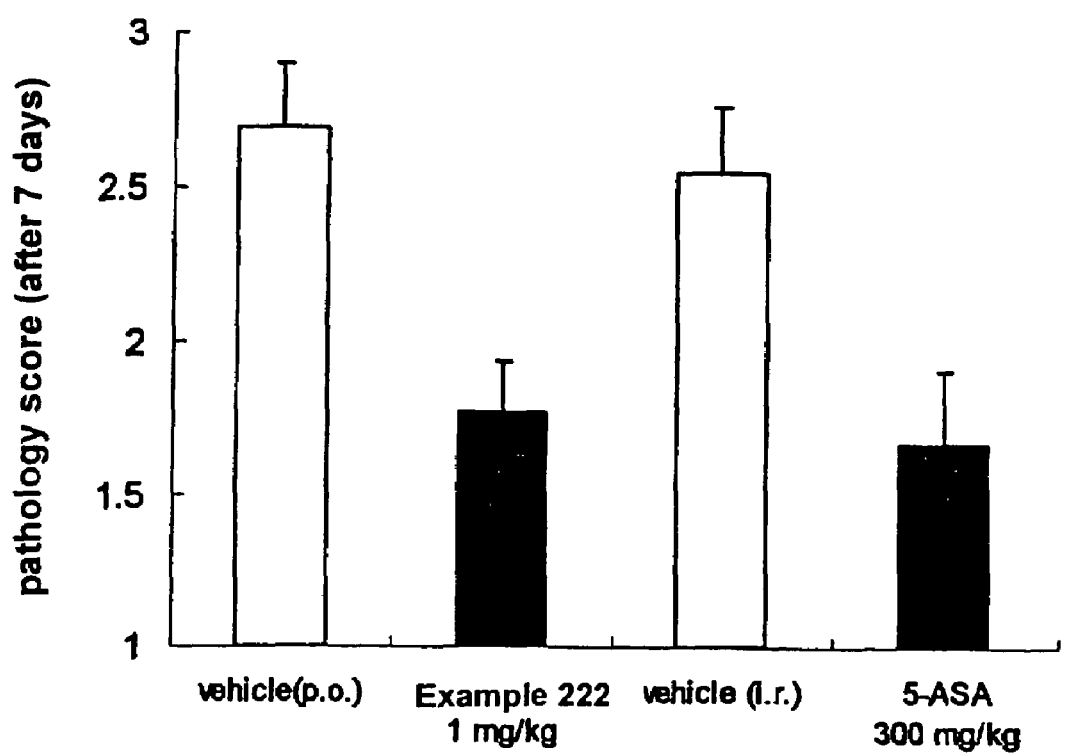
FIG. 3 shows the pathology score in DSS model when the compound of the present invention was administered.
Figure 4:
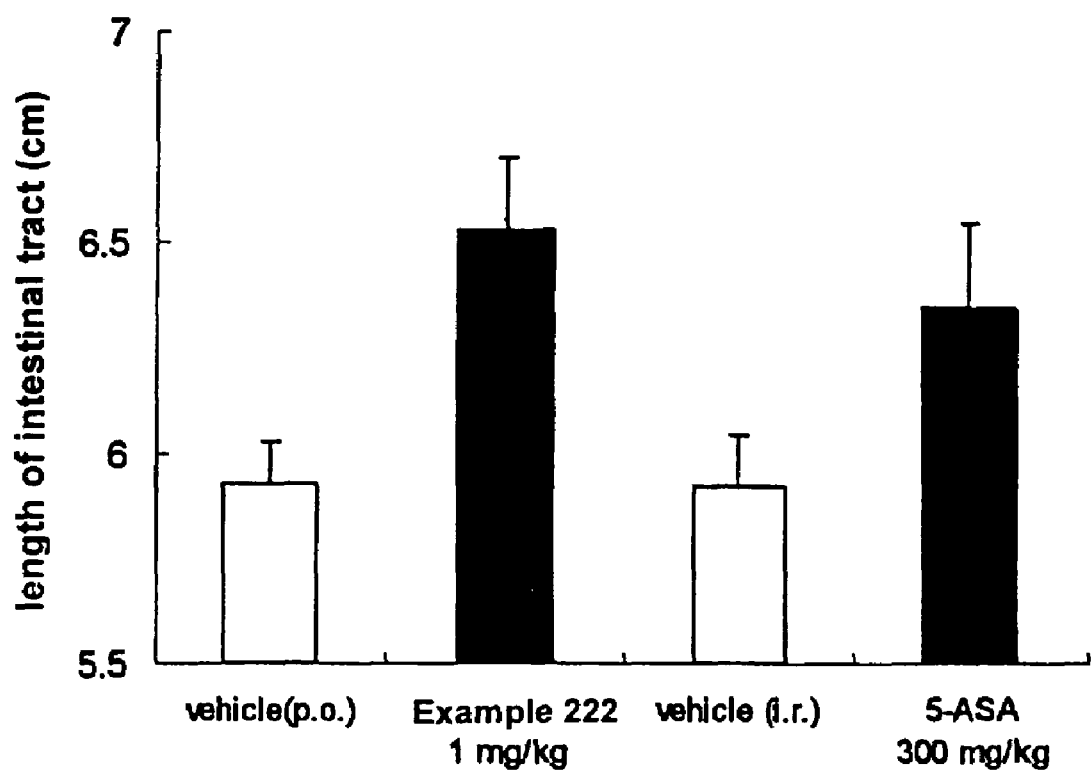
FIG. 4 shows the length of the intestinal tract in DSS model when the compound of the present invention was administered.

Male C57BL/6Cr slc mice (Japan SLC, Inc.) (8-week-old) were used. The mice were allowed to freely drink DSS (molecular weight: 5000 kDa, WAKO) 3% (dissolved in tap water) for 7 days to induce colitis. Each compound was suspended in 0.5% CMC (10 mL/kg) and orally administered at a frequency of once a day. 5-ASA (5-aminosalicylic acid) was suspended in 0.5% CMC (5 mL/kg), and administrated via an enema at 300 mg/kg once a day. The amount of water drunk, the amount of feed taken and the body weight were measured for 7 days from the start of drinking water, and the levels of stool characteristics and bleeding were scored and calculated as the disease activity index (DAI). On day 7, the mice were autopsied and the length of the intestinal tract was measured. The standard of DAI and the test results are shown in Table 7 and FIGS. 3 and 4.

TABLE 7

| | Pathological score | | |
| --- | --- | --- | --- |
| score | weight loss | stool characteristics | bleeding |
| 0 | None | normal | None |
| 1 | 1-5% | | |
| 2 | 5-10% | loose stool | occult blood |
| 3 | 10-20% | | |
| 4 | >20% | diarrhea | hemorrhage |

INDUSTRIAL APPLICABILITY

The present invention provides a novel ether derivative. The ether derivatives (I) and (III) of the present invention have superior anti-inflammatory and analgesic activities and are capsaicin-like agonistic substances or substances antagonizing capsaicin action. Therefore, they are suitable as therapeutic agents for general pain such as headache, toothache, muscle ache, menstrual cramps, wound pain and the like, as well as neuropathic pain associated with diabetic neuropathy, trigeminal neuropathy, herpes zoster, hyperalgesia and the like, or inflammatory bowel diseases (Crohn's disease, ulcerative colitis etc.), articular rheumatism, steoarthrosis, Raynaud's disease, pruritus, allergic and nonallergic rhinitis, cystitis, pollakiuria and/or incontinentia, apoplexy, irritable bowel syndrome, respiratory diseases (asthma, chronic obstructive pulmonary disease etc.), dermatitis, gastric ulcer, duodenal ulcer, functional dyspepsia, dysphagia and esophageal reflux, and are particularly useful for inflammatory bowel disease, incontinentia and/or pollakiuria and asthma.

This application is based on a patent application Nos. 2003-354086 and 2004-199934 filed in Japan, the contents of which are hereby incorporated by reference. The references cited herein, including patents and patent applications, are hereby incorporated in their entireties by reference, to the extent that they have been disclosed herein.

The structures of the compounds produced in respective Examples are described in the following Table 8-Table 31. $[M+H]^+$ shows measured values of Mass.

TABLE 8

| Example (Ex) | Ar1 R5 R6 R7 R8 R4 | Ar2 R9 R10 R11 R12 R13 | salt | Mass found ([M + H]$^+$) | NMR |
|---|---|---|---|---|---|
| 1 | 4-F—Ph | 2-Br—Ph | — | 353 | $^1$H-NMR (300 MHz, DMSO-d$_6$) δ 3.47 (2H, q), 4.02 (2H, t), 6.90 (1H, t), 6.79-7.02 (2H, m), 7.10-7.16 (2H, m), 7.28 (1H, t), 7.35 (1H, brt), 7.55 (1H, dd), 7.96 (1H, s), 8.05 (1H, dd) |
| 2 | 4-F—Ph | 1-naphthyl | — | 325 | — |
| 3 | 3-Me—Ph | 2-Br—Ph | — | 349 | — |
| 4 | 3-Me—Ph | 1-naphthyl | — | 321 | — |
| 5 | 4-Me—Ph | 2-Br—Ph | — | 349 | $^1$H-NMR (300 MHz, DMSO-d$_6$) δ 2.23 (3H, s), 3.48 (2H, q), 3.99 (2H, t), 6.85-6.89 (3H, m), 7.09 (2H, d), 7.28 (1H, t), 7.34 (1H, brt), 7.55 (1H, d), 7.96 (1H, s), 7.05 (1H, d) |
| 6 | 4-Me—Ph | 1-naphthyl | — | 321 | — |
| 7 | 2-pyridyl | 4-t-butyl | TFA | 314 | $^1$H-NMR (300 MHz, DMSO-d$_6$) δ 1.24 (9H, s), 3.48 (2H, brs), 4.29 (2H, t), 6.32 (1H, m), 6.84 (1H, dd), 6.96-7.01 (1H, m), 7.23 (2H, d), 7.29 (2H, d), 7.70-7.78 (1H, m), 8.18 (1H, dd), 8.44 (1H, s) |
| 8 | 2-pyridyl | 1-naphthyl | TFA | 308 | — |
| 9 | 2-Cl-6-pyridyl | 4-t-butyl | TFA | 348 | — |
| 10 | 2-Cl-6-pyridyl | 1-naphthyl | TFA | 342 | — |
| 11 | 4-OH—Ph | 4-t-butyl | — | 329 | — |
| 12 | 3-CF3-2-pyridyl | 4-t-butyl | TFA | 382 | — |
| 13 | 4-Cl—Ph | 1-naphthyl | — | 341 | — |
| 14 | 4-Br—Ph | 2-Br—Ph | — | 414 | $^1$H-NMR (300 MHz, DMSO-d$_6$) δ 3.48 (2H, m), 4.03 (2H, t), 6.88-6.98 (3H, m), 7.27 (1H, td), 7.36 (1H, t), 7.47 (2H, d), 7.55 (1H, d), 7.96 (1H, s), 8.06 (1H, d) |

TABLE 9

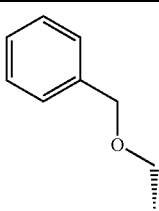

| Ex | A | Ar2 R9 R10 R11 R12 R13 | salt | [M + H]$^+$ | NMR |
|---|---|---|---|---|---|
| 15 | | 1-naphthyl | — | 441 | — |

TABLE 9-continued

| Ex | A | Ar2/R9-R13 | salt | [M + H]⁺ | NMR |
|----|---|------------|------|----------|-----|
| 16 | (R)-benzyloxymethyl (CH with wedge to OCH₂Ph) | 2-Br—Ph | — | 469 | ¹H-NMR (300 MHz, DMSO-d₆) δ 2.27 (3H, s), 3.62 (2H, m), 4.05 (2H, m), 4.18 (1H, m), 4.55 (2H, s), 6.74-6.79 (3H, m), 6.91 (1H, t), 7.17 (1H, t), 7.24-7.33 (6H, m), 7.39 (1H, d), 7.55 (1H, d), 8.03-8.07 (2H, m) |
| 17 | (S)-benzyloxymethyl (CH with wedge to OCH₂Ph) | 2-Br—Ph | — | 469 | — |
| 18 | benzylsulfonylmethyl (CH₂S(O)₂CH₂Ph) | 1-naphtyl | — | 489 | — |
| 19 | benzylsulfonylmethyl | 2-Br—Ph | — | 517 | ¹H-NMR (300 MHz, DMSO-d₆) δ 2.28 (3H, s), 3.38-3.52 (2H, m), 4.02-4.19 (2H, m), 4.55-4.63 (3H, m), 6.74-6.79 (3H, m), 6.92 (1H, td), 7.18 (1H, td), 7.31 (1H, td), 7.38-7.42 (5H, m), 7.58 (2H, td), 8.02-8.08 (2H, m) |
| 20 | N-ethylbenzamide (PhC(O)NHCH₂-) | 1-naphtyl | — | 454 | — |

TABLE 10

[Structure: Ar4-O-CH2-CH(CH3)-NH-C(=O)-NH-isoquinolin-5-yl, with (S) stereochemistry]

| Ex | Ar4 | salt | [M + H]+ |
|---|---|---|---|
| 21 | 3-F—Ph | TFA | 340 |
| 22 | 4-F—Ph | TFA | 340 |
| 23 | 3-Me—Ph | TFA | 336 |
| 24 | 4-Me—Ph | TFA | 336 |
| 25 | 3-CF3—Ph | TFA | 390 |
| 26 | 4-CF3—Ph | TFA | 390 |
| 27 | 3-OMe—Ph | TFA | 352 |
| 28 | 4-OMe—Ph | TFA | 352 |
| 29 | 3-OCF3—Ph | TFA | 406 |
| 30 | 4-OCF3—Ph | TFA | 406 |
| 31 | 3-iPr—Ph | TFA | 364 |
| 32 | 4-iPr—Ph | TFA | 364 |
| 33 | 3-tBu—Ph | TFA | 378 |
| 34 | 4-tBu—Ph | TFA | 378 |
| 35 | 3-Et—Ph | TFA | 350 |
| 36 | 4-Et—Ph | TFA | 350 |
| 37 | 2-F—Ph | TFA | 340 |
| 38 | 3-Cl—Ph | TFA | 356 |
| 39 | 4-Cl—Ph | TFA | 356 |
| 40 | 3-Br—Ph | TFA | 400 |
| 41 | 4-Br—Ph | TFA | 400 |
| 42 | 3-I—Ph | TFA | 448 |
| 43 | 4-I—Ph | TFA | 448 |
| 44 | 3-NO2—Ph | TFA | 367 |
| 45 | 4-NO2—Ph | TFA | 367 |
| 46 | 4-SMe—Ph | TFA | 368 |
| 47 | 4-CO2Et | TFA | 394 |
| 48 | 2,3-di-F—Ph | TFA | 358 |
| 49 | 2,4-di-F—Ph | TFA | 358 |
| 50 | 2,5-di-F—Ph | TFA | 358 |
| 51 | 3,4-di-F—Ph | TFA | 358 |
| 52 | 3,5-di-F—Ph | TFA | 358 |
| 53 | 3-Cl-4-F—Ph | TFA | 374 |
| 54 | 3-F-4-Cl—Ph | TFA | 374 |
| 55 | 3,4-di-Cl—Ph | TFA | 390 |
| 56 | 3,5-di-Cl—Ph | TFA | 390 |
| 57 | 3-F-4-Me—Ph | TFA | 354 |
| 58 | 3-Me-4-F—Ph | TFA | 354 |
| 59 | 3-F-5-CF3—Ph | TFA | 406 |
| 60 | 3-Me-4-Cl—Ph | TFA | 370 |
| 61 | 3-CF3-4-Cl—Ph | TFA | 424 |
| 62 | 2,4-di-Me—Ph | TFA | 350 |
| 63 | 3,4-di-Me—Ph | TFA | 350 |
| 64 | 3,5-di-Me—Ph | TFA | 350 |
| 65 | 3,4,5-tri-Me—Ph | TFA | 364 |
| 66 | 3-Me-5-OMe—Ph | TFA | 366 |
| 67 | 3,4-di-OMe—Ph | TFA | 382 |
| 68 | 3,5-di-OMe—Ph | TFA | 382 |
| 69 | 3,4,5-tri-OMe—Ph | TFA | 412 |
| 70 | 2,3,4-tri-F—Ph | TFA | 376 |
| 71 | 3,4,5-tri-F—Ph | TFA | 376 |
| 72 | 2,4,5-tri-F—Ph | TFA | 376 |
| 73 | penta-F—Ph | TFA | 412 |
| 74 | 3-biphenyl | TFA | 398 |
| 75 | 4-biphenyl | TFA | 398 |
| 76 | 2-naphthyl | TFA | 372 |
| 77 | quinolin-5-yl | TFA | 373 |
| 78 | isoquinolin-7-yl | 2TFA | 373 |
| 79 | [indanyl structure] | TFA | 362 |

TABLE 10-continued

[Structure: Ar4-O-CH2-CH(CH3)-NH-C(=O)-NH-isoquinolin-5-yl, with (S) stereochemistry]

| Ex | Ar4 | salt | [M + H]+ |
|---|---|---|---|
| 80 | [tetrahydronaphthyl structure] | TFA | 376 |
| 81 | 6-CF3-pyrimidin-4-yl | 2TFA | 392 |
| 82 | 4-NH2—Ph | 2TFA | 337 |
| 83 | 4-NMe2—Ph | 2TFA | 365 |
| 84 | 3-NMe2-4-NO2—Ph | TFA | 410 |

TABLE 11

[Structure: Ar4-O-CH2-CH(A)-NH-C(=O)-NH-isoquinolin-5-yl]

| Ex | A | Ar4 | salt | [M + H]+ |
|---|---|---|---|---|
| 85 | Me | 3-F—Ph | TFA | 340 |
| 86 | Me | 4-Me—Ph | TFA | 336 |
| 87 | Et | 3-F—Ph | TFA | 354 |
| 88 | Et | 4-Me—Ph | TFA | 350 |
| 89 | Et | 3-Cl—Ph | TFA | 370 |
| 90 | Et | 2,3-di-F—Ph | TFA | 372 |
| 91 | Et | 3,4-di-F—Ph | TFA | 372 |
| 92 | Et | 3-Cl-4-F—Ph | TFA | 388 |

TABLE 11-continued

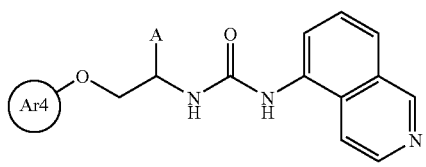

| Ex | A | Ar4 | salt | [M + H]+ |
|---|---|---|---|---|
| 93 | Et | 6-methyl-tetrahydronaphthyl | TFA | 390 |
| 94 | nPr | 3-F—Ph | TFA | 368 |
| 95 | nPr | 4-Me—Ph | TFA | 364 |
| 96 | nPr | 3,4-di-F—Ph | TFA | 386 |
| 97 | nPr | 3-Cl-4-F—Ph | TFA | 402 |
| 98 | iPr | 3-F—Ph | TFA | 368 |
| 99 | iPr | 4-Me—Ph | TFA | 364 |
| 100 | iPr | 3-F—Ph | TFA | 368 |
| 101 | iBu | 3-F—Ph | TFA | 382 |
| 102 | iBu | 4-F—Ph | TFA | 382 |
| 103 | iBu | 3-Me—Ph | TFA | 378 |
| 104 | iBu | 4-Me—Ph | TFA | 378 |
| 105 | iBu | 3-F—Ph | TFA | 382 |
| 106 | iBu | 4-Me—Ph | TFA | 378 |
| 107 | Ph | 3-F—Ph | TFA | 402 |
| 108 | Ph | 4-Me—Ph | TFA | 398 |

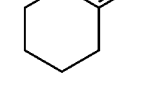

TABLE 12

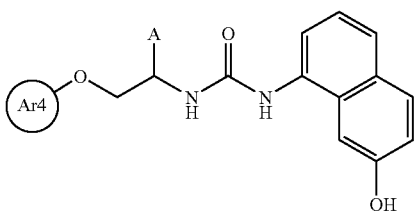

| Ex | A | Ar4 | salt | [M + H]+ |
|---|---|---|---|---|
| 109 | H | 3-F—Ph | — | 341 |
| 110 | H | 4-F—Ph | — | 341 |
| 111 | H | 3-Me—Ph | — | 337 |
| 112 | H | 4-Me—Ph | — | 337 |
| 113 | H | 4-Cl—Ph | — | 357 |
| 114 | Me | 3-F—Ph | — | 355 |
| 115 | Me | 4-Me—Ph | — | 351 |

TABLE 13

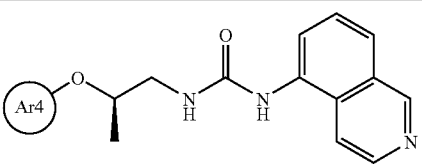

| Ex | Ar4 | salt | [M + H]+ |
|---|---|---|---|
| 116 | 3-F—Ph | TFA | 340 |
| 117 | 4-Me—Ph | TFA | 336 |

TABLE 14

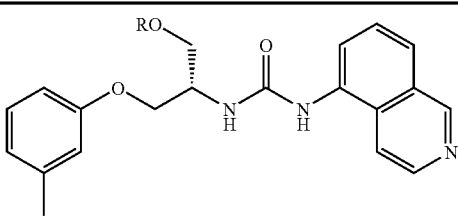

| Ex | R | salt | [M + H]+ |
|---|---|---|---|
| 118 | Me | TFA | 365 |
| 119 | H | TFA | 352 |
| 120 | COCH3 | TFA | 394 |
| 121 | COiBu | TFA | 436 |
| 122 | COtBu | TFA | 436 |
| 123 | COPh | TFA | 456 |
| 124 | cyclopropylcarbonyl | TFA | 420 |

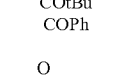

TABLE 14-continued

[Structure: RO-CH2-C*H(NHC(O)NH-isoquinolin-5-yl)-CH2-O-(3-methylphenyl)]

| Ex | R | salt | [M + H]+ |
|---|---|---|---|
| 125 | (acetylcyclopentyl group) | TFA | 448 |

TABLE 15

[Structure: 3-F-phenyl-O-CH2-C*H(A)(NHC(O)NH-isoquinolin-5-yl)]

| Ex | A | salt | [M + H]+ |
|---|---|---|---|
| 126 | BocNH-CH2-CH2- | TFA | 455 |
| 127 | H2N-CH2- | 2TFA | 355 |

TABLE 16

[Structure: Ar4-O-(CH2)m-CH(A)-NHC(O)NH-isoquinolin-5-yl]

| Ex | A | Ar4 | m | salt | [M + H]+ |
|---|---|---|---|---|---|
| 128 | SMe (propyl) | 4-Me—Ph | 1 | TFA | 396 |
| 129 | MeS (allyl) | 4-Me—Ph | 2 | TFA | 396 |

TABLE 16-continued

[Structure: Ar4-O-(CH2)m-CH(A)-NHC(O)NH-isoquinolin-5-yl]

| Ex | A | Ar4 | m | salt | [M + H]+ |
|---|---|---|---|---|---|
| 130 | SMe (propyl) | 3-F—Ph | 1 | TFA | 400 |
| 131 | MeS (ethyl) | 3-F—Ph | 1 | TFA | 386 |
| 132 | MeS (ethyl) | 4-Me—Ph | 1 | TFA | 382 |

TABLE 17

[Structure: Ar4-O-CH2-C*H(Me)-NHC(O)NH-isoquinolinyl with R13' and V1]

| Ex | Ar4 | R13' | V1 | salt | [M + H]+ |
|---|---|---|---|---|---|
| 133 | 3-Cl—Ph | H | N+—O− | — | 372 |
| 134 | 3,5-di-F—Ph | NH2 | N | 2TFA | 373 |

TABLE 18

[Structure: Ar1-O-CH2-CH2-NHC(O)NH-Ar2]

| Ex | Ar1 | Ar2 | salt | [M + H]+ |
|---|---|---|---|---|
| 135 | 3-F—Ph | 2-Br—Ph | — | 353 |
| 136 | 3-F—Ph | 4-tBu—Ph | — | 331 |
| 137 | 3-F—Ph | 1-naphthyl | — | 325 |
| 138 | 3,4-di-F—Ph | 2-Br—Ph | — | 371 |
| 139 | 3,4-di-F—Ph | 1-naphthyl | — | 343 |
| 140 | 5-Cl-pyridin-2-yl | 1-naphthyl | TFA | 342 |
| 141 | 5-CF3-pyridin-2-yl | 2-Br—Ph | TFA | 404 |
| 142 | 5-CF3-pyridin-2-yl | 1-naphthyl | TFA | 376 |

TABLE 19

| Ex | Ar3 | Ar2 | salt | [M + H]+ |
|---|---|---|---|---|
| 143 | 3-NO2-Ph | 2-Br—Ph | — | 514 |
| 144 | 3-NO2-Ph | 1-naphthyl | — | 486 |
| 145 | 3-NH2-Ph | 1-naphthyl | TFA | 456 |
| 146 | 4-CN—Ph | 2-Br—Ph | — | 494 |
| 147 | 4-Me—Ph | 2-Br—Ph | — | 463 |
| 148 | 4-Me—Ph | 1-naphthyl | — | 455 |
| 149 | 3-Me—Ph | 1-naphthyl | — | 455 |
| 150 | 3-CO2Me—Ph | 2-Br—Ph | — | 527 |
| 151 | 3-CO2Me—Ph | 1-naphthyl | — | 499 |
| 152 | 4-CO2Me—Ph | 1-naphthyl | — | 499 |
| 153 | 2-F—Ph | 2-Br—Ph | — | 487 |
| 154 | 2-F—Ph | 1-naphthyl | — | 459 |
| 155 | 3-F—Ph | 2-Br—Ph | — | 487 |
| 156 | 4-F—Ph | 2-Br—Ph | — | 487 |
| 157 | 4-F—Ph | 4-tBu—Ph | — | 465 |
| 158 | 4-F—Ph | 1-naphthyl | — | 459 |
| 159 | pyridin-3-yl | 1-naphthyl | TFA | 442 |
| 160 | pyridin-4-yl | 1-naphthyl | TFA | 442 |

TABLE 20

| Ex | Ar1 | Ar2 | salt | [M + H]+ |
|---|---|---|---|---|
| 161 | 3-F—Ph | 2-Br—Ph | — | 473 |
| 162 | 3-F—Ph | 1-naphthyl | — | 445 |
| 163 | 4-F—Ph | 2-Br—Ph | — | 473 |
| 164 | 4-F—Ph | 1-naphthyl | — | 445 |
| 165 | 5-CF3-pyridin-2-yl | 2-Br—Ph | TFA | 524 |
| 166 | 3-Me—Ph | isoquinolin-5-yl | TFA | 442 |
| 167 | 4-Me—Ph | isoquinolin-5-yl | TFA | 442 |
| 168 | 3-F—Ph | isoquinolin-5-yl | TFA | 446 |
| 169 | 4-F—Ph | isoquinolin-5-yl | TFA | 446 |
| 170 | 4-CF3-Ph | isoquinolin-5-yl | TFA | 496 |
| 171 | 3-Me—Ph | 7-OH-1-naphthyl | — | 457 |
| 172 | 3-F—Ph | 7-OH-1-naphthyl | — | 461 |
| 173 | 3-Me—Ph | 2-Cl-7-OH-1-naphthyl | — | 490 |

TABLE 21

| Ex | A | Ar2 | salt | [M + H]+ |
|---|---|---|---|---|
| 174 | 2-(NO2)-N-ethyl-anilinyl | 2-Br—Ph | — | 499 |
| 175 | 2-(NO2)-N-ethyl-anilinyl | 4-tBu—Ph | — | 477 |
| 176 | 4-F-2-(NO2)-N-ethyl-anilinyl | 2-Br—Ph | — | 517 |
| 177 | 4-F-2-(NO2)-N-ethyl-anilinyl | 1-naphthyl | — | 489 |

TABLE 21-continued

[Structure: 3-methylphenoxy-CH2-CH(A)-NH-C(=O)-NH-Ar2]

| Ex | A | Ar2 | salt | [M + H]+ |
|---|---|---|---|---|
| 178 | 2-nitrophenyl-NH-CH2- | isoquinolin-5-yl | TFA | 472 |
| 179 | 2-nitrophenyl-NH-CH(Et)- | isoquinolin-5-yl | TFA | 472 |
| 180 | 3-nitropyridin-2-yl-NH-CH(Et)- | isoquinolin-5-yl | 2TFA | 473 |
| 181 | 4-nitro-2-CF3-phenyl-NH-CH(Et)- | isoquinolin-5-yl | 2TFA | 540 |
| 182 | 1-ethyl-benzimidazol-2-yl- | 1-naphthyl | TFA | 451 |

TABLE 22

[Structure: Ar4-O-CH2-CH(CH2-NH-(2-nitrophenyl))-NH-C(=O)-NH-isoquinolin-5-yl]

| Ex | Ar4 | salt | [M + H]+ |
|---|---|---|---|
| 183 | 4-Me—Ph | TFA | 472 |
| 184 | 3-F—Ph | TFA | 476 |
| 185 | 4-F—Ph | TFA | 476 |

TABLE 23

[Structure: 3-methylphenoxy-CH2-CH(A)-NH-C(=O)-NH-(2-bromophenyl)]

| Ex | A | salt | [M + H]+ |
|---|---|---|---|
| 186 | phenoxymethyl | — | 455 |
| 187 | (4-fluoro-2-F-phenoxy)methyl | — | 473 |

TABLE 24

| Ex | Ar2 | salt | [M + H]+ |
|---|---|---|---|
| 188 | 2-Br—Ph | — | 469 |
| 189 | 1-naphthyl | — | 441 |

TABLE 25

| Ex | R8' | salt | [M + H]+ |
|---|---|---|---|
| 190 | 4-CN—Ph | TFA | 347 |
| 191 | 3-CN—Ph | TFA | 347 |

TABLE 26

| Ex | A | R8' | salt | [M + H]+ |
|---|---|---|---|---|
| 192 | Et | 3,5-di-F—Ph | TFA | 372 |
| 193 | Et | 2,5-di-F—Ph | TFA | 372 |

TABLE 26-continued

| Ex | A | R8' | salt | [M + H]+ |
|---|---|---|---|---|
| 194 | Et | 2,4-di-F—Ph | TFA | 372 |
| 195 | Et | 2,4,5-tri-F—Ph | TFA | 390 |
| 196 | nPr | 3,5-di-F—Ph | TFA | 386 |
| 197 | nPr | 2,4-di-F—Ph | TFA | 386 |
| 198 | nPr | 2,5-di-F—Ph | TFA | 386 |
| 199 | nPr | 2,3-di-F—Ph | TFA | 386 |

TABLE 27

| Ex | A | R8' | salt | [M + H]+ |
|---|---|---|---|---|
| 200 | Me | 3,5-di-F—Ph | — | 373 |
| 201 | Me | 3,4-di-F—Ph | — | 373 |
| 202 | Et | 3-F—Ph | — | 369 |
| 203 | Et | 3,5-di-F—Ph | — | 387 |
| 204 | nPr | 3-F—Ph | — | 383 |
| 205 | nPr | 3,5-di-F—Ph | — | 401 |

TABLE 28

[Structure with R4', R5', R6', R7', R8', Ar4, A, V1, V2, R13']

| Ex | Ar4 R5'/R6'/R7'/R8' | A | V1 | V2 | R13' | salt | [M + H]+ |
|---|---|---|---|---|---|---|---|
| 206 | 3,5-di-F—Ph | nPr | CH | N+—O− | H | — | 402 |
| 207 | 3,4-di-F—Ph | Me | CH | N | NH2 | 2TFA | 373 |
| 208 | 3,4-di-F—Ph | Et | CH | N | NH2 | 2TFA | 387 |
| 209 | 3,4-di-F—Ph | Me | CH | N | NHCOCF3 | TFA | 469 |
| 210 | 3,4-di-F—Ph | nPr | C—NH2 | N | H | TFA | 401 |
| 211 | 3-F—Ph | Me | N | CH | H | TFA | 340 |
| 212 | 3,4-di-F—Ph | Me | N | CH | H | TFA | 358 |

TABLE 29

[Structure]

| Ex | Ar4 | A | X' | salt | [M + H]+ |
|---|---|---|---|---|---|
| 213 | 3-Cl—Ph | Me | N—CN | TFA | 380 |
| 214 | 3,4-di-F—Ph | nPr | N—OH | TFA | 401 |

TABLE 30

[Structure]

| Ex | A | Ar4 | salt |
|---|---|---|---|
| 215 | Me | 3-Cl—Ph | HCl |
| 216 | Me | 3,4-di-F—Ph | HCl |

TABLE 30-continued

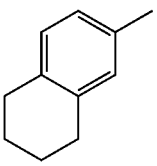

| Ex | A | Ar4 | salt |
|---|---|---|---|
| 217 | Me | 3,5-di-F—Ph | HCl |
| 218 | Me | [tetralin-methyl] | HCl |
| 219 | Et | 3,4-di-F—Ph | HCl |
| 220 | Et | 3-Cl-4-F—Ph | HCl |
| 221 | nPr | 3-F—Ph | HCl |
| 222 | nPr | 3,4-di-F—Ph | HCl |

TABLE 31

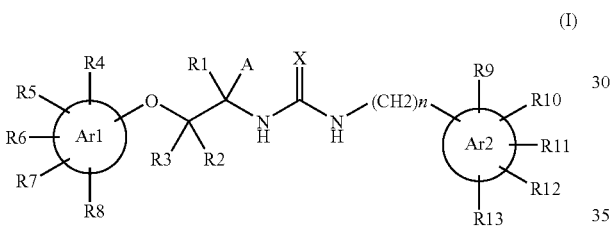

| Ex | A | | salt | [M + H]⁺ |
|---|---|---|---|---|
| 223 | Me | 3,5-di-F—Ph | — | 407 |
| 224 | Me | 3,4-di-F—Ph | — | 407 |

What is claimed is:

1. An ether compound of formula (I), a pharmaceutically acceptable salt thereof, or a hydrate thereof:

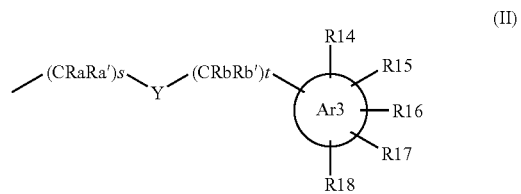

wherein

Ar1 is an aryl group,

Ar2 is a pyridazinyl group, pyrimidinyl group, pyrazinyl group, furyl group, thienyl group, pyrrolyl group, isoxazolyl group, oxazolyl group, isothiazolyl group, pyrazolyl group, imidazolyl group, benzofuranyl group, benzothienyl group, indolyl group, isoindolyl group, benzoxazolyl group, benzthiazolyl group, benzimidazolyl group, indazolyl group, benzisoxazolyl group, benzisothiazolyl group, quinolyl group, isoquinolyl group, cinnolinyl group, phthalazinyl group, quinazolinyl group or quinoxalinyl group, X is an oxygen atom or a sulfur atom, n is 0, R1-R3 are each independently a hydrogen atom or a $C_{1-6}$ alkyl group, R4-R8 are each independently a hydrogen atom, a halogen atom, a $C_{1-6}$ alkyl group, a $C_{2-6}$ alkenyl group, a $C_{2-6}$ alkynyl group, a $C_{1-3}$ penfluoroalkyl group, a hydroxyl group, a alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{2-6}$ aryl-carbonylamino group, a $C_{1-6}$ alkyl group substituted by one or more hydroxy groups, a carboxyl group, a phenyl group, or a naphthyl group, R9-R13 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{2-6}$ aryl-carbonylamino group, a $C_{1-6}$ alkyl group substituted by one or more hydroxy groups, a carboxyl group, a $C_{1-6}$ alkoxy group substituted by one or more amino groups, or a alkoxy group substituted by one or more hydroxy groups, and A is a hydrogen atom, a $C_{1-6}$ alkyl group, a $C_{1-6}$ alkyl group substituted by one or more hydroxy groups, a $C_{1-6}$ alkyl group substituted by one or more carboxyl groups, a alkyl group substituted by one or more amino groups, a $C_{1-6}$ alkyl group substituted by one or more amino groups which are monosubstituted by a $C_{1-6}$ alkyl group, a $C_{1-6}$ alkyl group substituted by one or more amino groups which are disubstituted by $C_{1-6}$ alkyl groups, or a group represented by the formula (II):

$$\text{—(CRaRa')}_s\text{—Y—(CRbRb')}_t\text{—Ar3}\begin{matrix}R14\\R15\\R16\\R17\\R18\end{matrix} \quad (II)$$

wherein

Ar3 is an aryl group, a heteroaryl group, or a nonaromatic heterocyclic group,

Y is —O—, —CH₂—, —NR19-, —S—, —S(O)—, —SO₂—, —NR19SO₂—, —SO₂NR19-, —C(O)NR19-, —NR19C(O)—, —NR19C(O)O1—or —OC(O)NR19-,

Ra, Ra', Rb and Rb' are each independently a hydrogen atom or a $C_{1-6}$ alkyl group, s is an integer of 1 or 2, t is an integer of 0-2, R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_1$-$C_6$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{6-12}$ aryl-carbonylamino group, a $C_{1-6}$ alkyl group substituted by one or more hydroxy groups, a carboxyl group, a $C_1$-$C_6$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkoxy-carbonyl group, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and R19 is hydrogen atom or a $C_{1-6}$ alkyl group, provided that:
(1) when Ar2 is a bicyclic heteroaryl containing at least one nitrogen atom, then A is a group other than a hydrogen atom, and
(2) the following compounds (X-1)-(X-7) are excluded

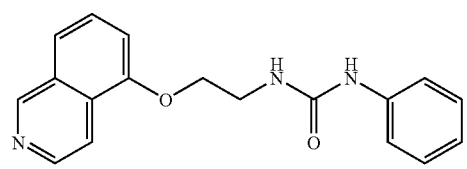
(X-1)

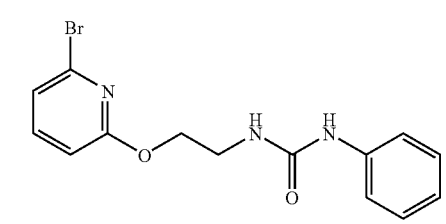
(X-2)

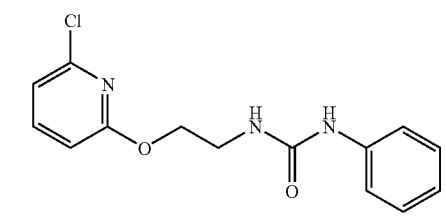
(X-3)

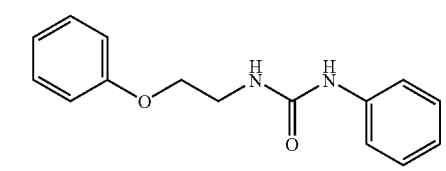
(X-4)

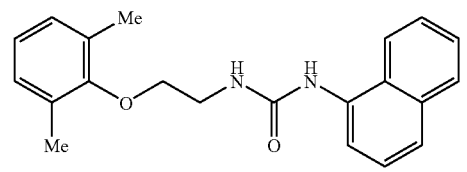
(X-5)

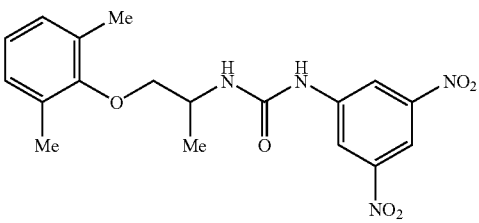
(X-6)

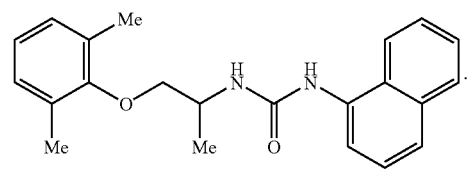
(X-7)

2. An ether compound represented by formula (I), a pharmaceutically acceptable salt thereof, or a hydrate thereof:

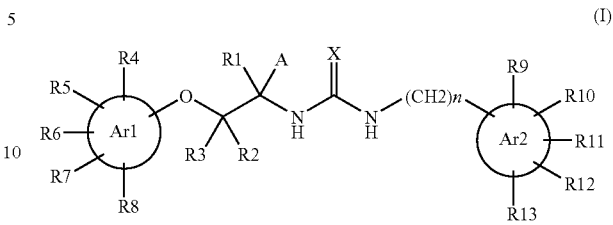
(I)

wherein
Ar1 is a phenyl group,
Ar2 is a pyridazinyl group, pyrimidinyl group, pyrazinyl group, furyl group, thienyl group, pyrrolyl group, isoxazolyl group, oxazolyl group, isothiazolyl group, pyrazolyl group, imidazolyl group, benzofuranyl group, benzothienyl group, indolyl group, isoindolyl group, benzoxazolyl group, benzthiazolyl group, benzimidazolyl group, indazolyl group, benzisoxazolyl group, benzisothiazolyl group, quinolyl group, isoquinolyl group, cinnolinyl group, phthalazinyl group, quinazolinyl group or quinoxalinyl group,
X is an oxygen atom or a sulfur atom,
n is 0,
R1-R3 are each independently a hydrogen atom or a $C_{1-6}$ alkyl group,
R4-R8 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a $C_{1-6}$ acylamino group, a $C_{1-6}$ alkyl group substituted by one or more hydroxy groups, a carboxyl group, a phenyl group or a naphthyl group,
R9-R13 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a $C_{1-6}$ acylamino group, a $C_{1-6}$ alkyl group substituted by one or more hydroxy groups, a carboxyl group, a $C_{1-6}$ alkoxy group substituted by one or more amino groups, or a $C_{1-6}$ alkoxy group substituted by one or more hydroxy groups, and
A is a hydrogen atom, a $C_{1-6}$ alkyl group, a $C_{1-6}$ alkyl group substituted by one or more hydroxy groups, a $C_{1-6}$ alkyl group substituted by one or more carboxyl groups, a $C_{1-6}$ alkyl group substituted by one or more amino groups, a $C_{1-6}$ alkyl group substituted by one or more amino groups which are monosubstituted by a $C_{1-6}$ alkyl group, a $C_{1-6}$ alkyl group substituted by one or more amino groups which are disubstituted by $C_{1-6}$ alkyl groups, or a group represented by formula (II):

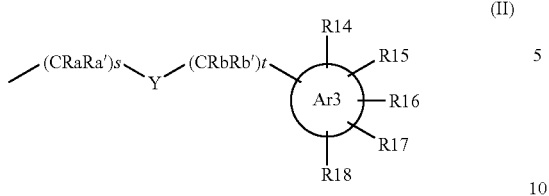

(II)

wherein

Ar3 is a phenyl group, a naphthyl group, a heteroaryl group, an indolinyl group, or an isoindolinyl group, Y is —O—, —$CH_2$—, —NR19-, —S—, —S(O)—, —$SO_2$—, —$NR19SO_2$—, —$SO_2NR19$—, —C(O)NR19-, —NR19C(O)—, —NR19C(O)O—, or —OC(O)NR19-, Ra, Ra', Rb and Rb' are each independently a hydrogen atom or a $C_{1-6}$ alkyl group, s is an integer of 1 or 2, t is an integer of 0-2, R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a $C_{1-6}$ acylamino group, a $C_{1-6}$ alkyl group substituted by one or more hydroxy groups, a carboxyl group, a $C_{1-6}$, alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkoxy-carbonyl group, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and R19 is a hydrogen atom or a $C_{1-6}$ alkyl group, provided that:

(1) when Ar2 is a bicyclic heteroaryl containing at least one nitrogen atom, then A is a group other than a hydrogen atom, and (2) the following compounds (X-1)-(X-7) are excluded:

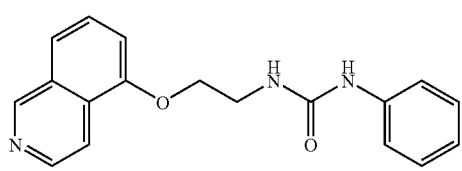

(X-1)

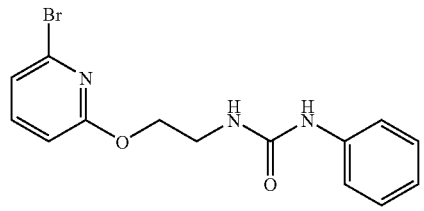

(X-2)

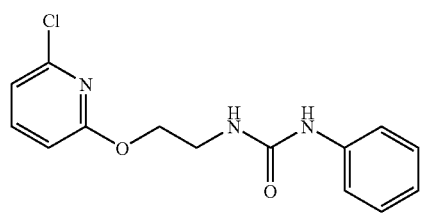

(X-3)

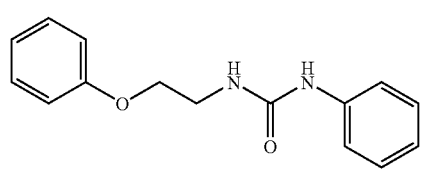

(X-4)

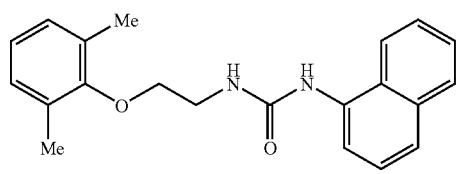

(X-5)

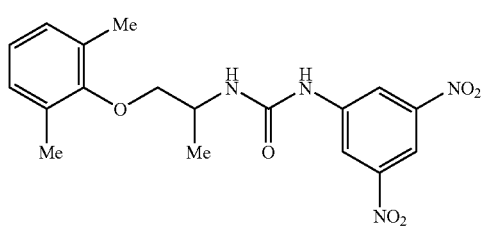

(X-6)

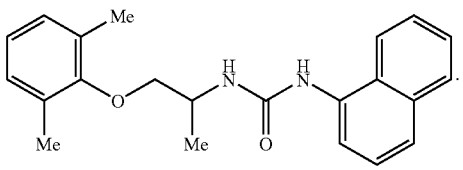

(X-7)

3. The ether compound of claim 1, having formula (I), wherein

A is a hydrogen atom,

Ar1 is a phenyl group,

X is an oxygen atom, n is 0, and

R1-R3 are each independently a hydrogen atom, a pharmaceutically acceptable salt thereof, or a hydrate thereof.

4. The ether compound of claim 1, having formula (I), wherein

A is a group represented by formula (II):

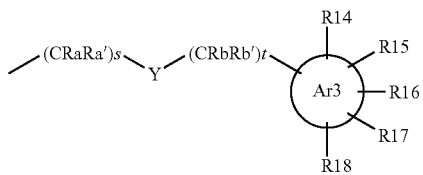
(II)

Ar3 is a phenyl group, a naphthyl group, a heteroaryl group, an indolinyl group, or an isoindolinyl group, Y is —O—, —CH$_2$—, —NR19-, —S—, —S(O)—, —SO$_2$—, —NR19SO$_2$—, —SO$_2$NR19-, —C(O)NR 19-, —NR 19C(O)—, —NR19C(O)O—, or —OC(O)NR19-, Ra, Ra', Rb and Rb' are each independently a hydrogen atom or a C$_{1-6}$ alkyl group, s is an integer of 1 or 2, t is an integer of 0-2, R14-R18 are each independently a hydrogen atom, a halogen atom, a C$_{1-6}$ alkyl group, a C$_{2-6}$ alkenyl group, a C$_{2-6}$ alkynyl group, a C$_{1-3}$ perfluoroalkyl group, a hydroxyl group, a C$_{1-6}$ alkylthio group, a C$_{1-6}$ alkylsulfinyl group, a C$_{1-6}$ alkylsulfonyl group, a C$_{1-6}$ alkoxy group, a C$_{1-3}$ perfluoroalkoxy group, a cyano group, a nitro group, a C$_{1-6}$ alkyl-carbonyl group, an amino group, an amino group monosubstituted by a C$_{1-6}$ alkyl group, an amino group disubstituted by C$_{1-6}$ alkyl groups, a C$_{1-6}$ alkylsulfonylamino group, a C$_{1-6}$ acylamino group, a C$_{1-6}$ alkyl group substituted by one or more hydroxy groups, a carboxyl group, a alkoxy group substituted by one or more amino groups, a C$_{1-6}$ alkoxy group substituted by one or more hydroxy groups, a C$_{3-8}$ cycloalkyl group, a nonaromatic heterocyclic group, a carbamoyl group monosubstituted by a C$_{1-6}$ alkyl group, a carbamoyl group disubstituted by C$_{1-6}$ alkyl groups, a C$_{1-6}$ alkoxycarbonyl group, a C$_{1-6}$ alkyl group substituted by one or more amino groups, a C$_{1-6}$ alkyl group substituted by one or more amino groups which are monosubstituted by a C$_{1-6}$, alkyl group, or a C$_{1-6}$ alkyl group substituted by one or more amino groups which are disubstituted by C$_{1-6}$ alkyl groups, Ar1 is a phenyl group, X is an oxygen atom, n is 0, and R1-R3 are each independently a hydrogen atom, a pharmaceutically acceptable salt thereof, or a hydrate thereof.

5. The ether compound of claim 1, having formula (I), wherein

A is a group represented by formula (II)

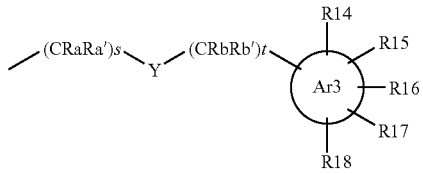
(II)

Ar3 is a phenyl group, a naphthyl group, a heteroaryl group, an indolinyl group, or an isoindolinyl group, Y is —O—, —CH$_2$—, —NR19-, —S—, —S(O)—, —SO$_2$—, —NR19SO$_2$—, —SO$_2$NR19-, —C(O)NR19-, —NR19C(O)—, —NR19C(O)O—, or —OC(O)NR19-, Ra, Ra', Rb and Rb' are each independently a hydrogen atom or a C$_{1-6}$ alkyl group, s is an integer of 1 or 2, t is an integer of 0-2, R14-R18 are each independently a hydrogen atom, a halogen atom, a C$_{1-6}$ alkyl group, a C$_{2-6}$ alkenyl group, a C$_{2-6}$ alkynyl group, a C$_{1-3}$ perfluoroalkyl group, a hydroxyl group, a C$_{1-6}$ alkylthio group, a C$_{1-6}$ alkylsulfinyl group, a C$_{1-6}$ alkylsulfonyl group, a C$_{1-6}$ alkoxy group, a C$_{1-3}$ perfluoroalkoxy group, a cyano group, a nitro group, a C$_{1-6}$, alkyl-carbonyl group, an amino group, an amino group monosubstituted by a C$_{1-6}$ alkyl group, an amino group disubstituted by C$_{1-6}$ alkyl groups, a C$_{1-6}$ alkylsulfonylamino group, a C$_{1-6}$ acylamino group, a C$_{1-6}$ alkyl group substituted by one or more hydroxy groups, a carboxyl group, a alkoxy group substituted by one or more amino groups, a C$_{1-6}$ alkoxy group substituted by one or more hydroxy groups, a C$_{3-8}$ cycloalkyl group, a nonaromatic heterocyclic group, a carbamoyl group monosubstituted by a C$_{1-6}$ alkyl group, a carbamoyl group disubstituted by C$_{1-6}$ alkyl groups, a C$_{1-6}$ alkoxycarbonyl group, a C$_{1-6}$ alkyl group substituted by one or more amino groups, a C$_{1-6}$ alkyl group substituted by one or more amino groups which are monosubstituted by a C$_{1-6}$ alkyl group, or a C$_{1-6}$ alkyl group substituted by one or more amino groups which are disubstituted by C$_{1-6}$ alkyl groups, Ar1 is a phenyl group, Ar2 is a quinolyl group, an isoquinolyl group, an indolyl group, or an isoindolyl group, X is an oxygen atom, n is 0, R1-R3 are each independently a hydrogen atom, Ar3 is a phenyl group or a pynidyl group, Y is —O—, —SO$_2$—, or —NHC(O)—, Ra, Ra', Rb and Rb' are each independently a hydrogen atom, s is 1, t is 0 or 1, and a pharmaceutically acceptable salt thereof, or a hydrate thereof.

6. An ether compound represented by formula (III), a pharmaceutically acceptable salt thereof, or a hydrate thereof:

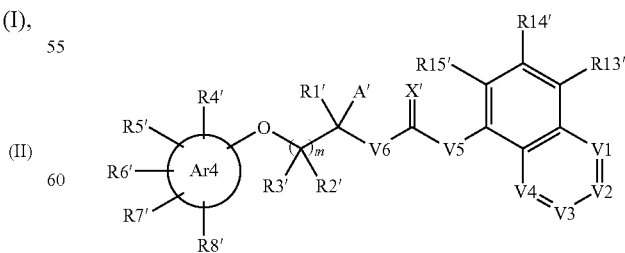
(III)

wherein

Ar4 is an aryl group or a heteroaryl group,

X' is an oxygen atom, a sulfur atom, N—CN, or N—OH,

V1 is a nitrogen atom, N→O, or CR9',
V2 is a nitrogen atom, N→O, or CR10',
V3 is a nitrogen atom or CR11',
V4 is a nitrogen atom or CR12',
V5 is NRc or CReRe',
V6 is NRd or CRfRf',
m is an integer of 1-3,
R1'-R3' are each independently a hydrogen atom or a $C_{1-6}$ alkyl group and when m is
2 or 3, and R2' and R3' present in plurality each R2' and R3' may be the same or different,
R4'-R15' are each independently a hydrogen atom, a halogen atom, a hydroxy group, a cyano group, a nitro group, a carboxyl group, a $C_{1-6}$ alkyl group optionally having one or more substituents, a $C_{2-6}$ alkenyl group optionally having one or more substituents, a alkynyl group optionally having one or more substituents, a $C_{3-8}$ cyclic alkyl group which optionally contains one or more hetero atoms in the ring, an aryl group optionally having one or more substituents, a heteroaryl group optionally having one or more substituents, a $C_{1-6}$ alkyl group substituted by one or more aryl groups optionally having one or more substituents, a $C_{1-6}$, alkyl group substituted by one or more heteroaryl groups which optionally have one or more substituents, a $C_{1-6}$, alkoxy group optionally having one or more substituents, a $C_{1-6}$ alkylthio group optionally having one or more substituents, a $C_{1-6}$ alkoxy group substituted by one or more aryl groups which optionally have one or more substituents, a $C_{1-6}$, alkylthio group substituted by one or more aryl groups which optionally have one or more substituents, a $C_{1-6}$, alkoxy group substituted by one or more heteroaryl groups which optionally have one or more substituents, a $C_{1-6}$ alkylthio group substituted by one or more heteroaryl groups which optionally have one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$ alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$, alkyl groups, a $C_{1-6}$ alkanoyl group optionally having one or more substituents, a $C_{7-12}$ aroyl group optionally having one or more substituents, a $C_{1-6}$ alkylsulfonylamino group, an arylsulfonylamino group optionally having one or more substituents, a heteroarylsulfonylamino group optionally having one or more substituents, a formylamino group, a $C_{1-6}$, alkyl-carbonylamino group, a $C_{2-6}$ alkenyl-carbonylamino group, a $C_{6-12}$ aryl-carbonylamino group, a $C_{1-6}$, perfluoroalkyl-carbonylamino group, a perfluoroalkenyl-carbonylamino group, a $C_{6-12}$ perfluoroaryl-carbonylamino group, a $C_{1-6}$ alkylsulfonyl group, or a $C_{1-6}$ alkylsulfinyl group, or
of R4', R5', R6', R7' and R8', those bonded to adjacent carbon atoms are optionally bonded to each other to form, together with the constituent carbon atoms of Ar4, a saturated or unsaturated ring, wherein the ring formed optionally contains one or more hetero atoms,
A' is a hydrogen atom, a halogen atom, a hydroxy group, a cyano group, a nitro group, a carboxyl group, a $C_{1-6}$ alkyl group optionally having one or more substituents, a alkenyl group optionally having one or more substituents, a $C_{2-6}$ alkynyl group optionally having one or more substituents, a $C_{3-8}$ cyclic alkyl group which optionally contains one or more hetero atoms in the ring, an aryl group optionally having one or more substituents, a heteroaryl group optionally having one or more substituents, a $C_{1-6}$ alkyl group substituted by one or more aryl groups which optionally have one or more substituents, a $C_{1-6}$ alkyl group substituted by one or more heteroaryl groups which optionally have one or more substituents, a $C_{1-6}$ alkoxy group optionally having one or more substituents, a $C_{1-6}$ alkylthio group optionally having one or more substituents, a $C_{1-6}$ alkoxy group substituted by one or more aryl groups which optionally have one or more substituents, a $C_{1-6}$ alkylthio group substituted by one or more aryl groups which optionally have one or more substituents, a $C_{1-6}$ alkoxy group substituted by one or more heteroaryl groups which optionally have one or more substituents, a $C_{1-6}$ alkylthio group substituted by one or more heteroaryl groups which optionally have one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$ alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$, alkyl groups, a $C_{1-6}$ alkanoyl group optionally having one or more substituents, a $C_{7-12}$ aroyl group optionally having one or more substituents, a $C_{1-6}$ alkylsulfonylamino group, an arylsulfonylamino group optionally having one or more substituents, a heteroarylsulfonylamino group optionally having one or more substituents, a formylamino group, a $C_{1-6}$ alkyl-carbonylamino group, a $C_{2-6}$ alkenyl-carbonylamino group, a $C_{1-6}$ aryl-carbonylamino group, a $C_{1-6}$ alkylsulfonyl group, a alkylsulfinyl group, or a group represented by the formula (II):

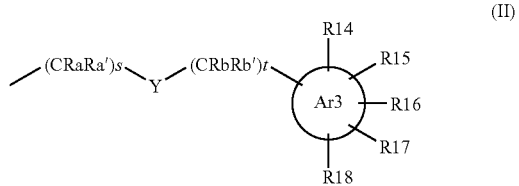

(II)

wherein
Ar3 is an aryl group, a heteroaryl group, or a nonaromatic heterocyclic group,
Y is —O—, —CH$_2$—, —NR19-, —S—, —S(O)—, —SO$_2$—, —NR19SO$_2$—, —SO$_2$NR19-, —C(O)NR19-, —NR19C(O)—, —NR19C(O)O— or —OC(O)NR19-,
Ra, Ra', Rb and Rb' are each independently a hydrogen atom or a $C_{1-6}$ alkyl group,
s is an integer of 1 or 2,
t is an integer of 0-2,
R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkylthio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$ alkyl-carbonyl group, an amino group, an amino group monosubstituted by a $C_{1-6}$ alkyl group, an amino group disubstituted by $C_{1-6}$ alkyl groups, a $C_{1-6}$ alkylsulfonylamino group, a formylamino group, a $C_{1-6}$ alkyl-carbonylamino group, a $C_{2-6}$ alkenyl-carbonylamino group, a $C_{7-12}$ aryl-carbonylamino group, a $C_{1-6}$ alkyl group substituted by one or more hydroxy groups, a carboxyl group, a $C_{1-6}$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkoxycarbonyl group, a $C_{1-6}$ alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and R19 is hydrogen atom or a $C_{1-6}$, alkyl group, and Rc, Rd, Re, Re', Rf and Rf' are each independently a hydrogen atom or a $C_{1-6}$ alkyl group, provided that:

(1) when at least one of V1, V2, V3, and V4 is a nitrogen atom, then at least one of R1', R2', R3', and A' is a group other than a hydrogen atom, and (2) the following compounds (X-5) and (X-7) are excluded:

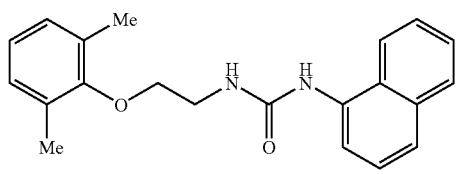
(X-5)

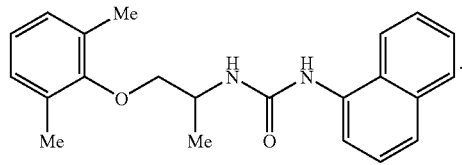
(X-7)

7. An ether compound represented by formula (III), a pharmaceutically acceptable salt thereof, or a hydrate thereof:

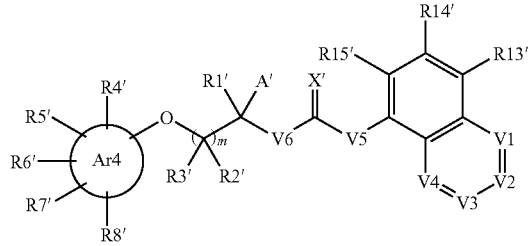
(III)

wherein

Ar4 is a phenyl group, a naphthyl group, or a heteroaryl group,

X' is an oxygen atom, a sulfur atom, N—CN, or N—OH,

V1 is a nitrogen atom, N→O, or CR9',

V2 is a nitrogen atom, N→O, or CR10',

V3 is a nitrogen atom or CR11',

V4 is a nitrogen atom or CR12',

V5 is NRc or CReRe',

V6 is NRd or CRfRf', m is an integer of 1-3,

R1'-R3' are each independently a hydrogen atom or a $C_{1-6}$ alkyl group and when m is 2 or 3, and R2' or R3' are present in multiplicity each of R2' or R3' may be the same or different, R4'-R15' are each independently a hydrogen atom, a halogen atom, a hydroxy group, a cyano group, a nitro group, a carboxyl group, a $C_{1-6}$ alkyl group optionally having one or more substituents, a $C_{2-6}$ alkenyl group optionally having one or more substituents, a $C_{2-6}$ alkynyl group optionally having one or more substituents, a $C_{3-8}$ cyclic alkyl group which optionally contains one or more hetero atoms in the ring, an aryl group optionally having one or more substituents, a heteroaryl group optionally having one or more substituents, a $C_{1-6}$, alkyl group substituted by one or more aryl groups which optionally have one or more substituents, a $C_{1-6}$, alkyl group substituted by one or more heteroaryl groups which optionally have one or more substituents, a $C_{1-6}$ alkoxy group optionally having one or more substituents, a $C_{1-6}$ alkylthio group optionally having one or more substituents, a $C_{1-6}$ alkoxy group substituted by one or more aryl groups which optionally have one or more substituents, a $C_{1-6}$ alkylthio group substituted by one or more aryl groups which optionally have one or more substituents, a $C_{1-6}$ alkoxy group substituted by one or more heteroaryl groups which optionally have one or more substituents, a $C_{1-6}$ alkylthio group substituted by one or more heteroaryl groups which optionally have one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$ alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$ alkyl groups, a $C_{1-6}$ alkanoyl group, a $C_{7-12}$ aroyl group optionally having one or more substituents, a $C_{1-6}$ alkylsulfonylamino group, an arylsulfonylamino group optionally having one or more substituents, a heteroarylsulfonylamino group optionally having one or more substituents, a $C_{1-6}$ acylamino group, a $C_{2-6}$ perfluoroacylamino group, a $C_{1-6}$, alkylsulfonyl group, or a $C_{1-6}$ alkylsulfinyl group, or of R4', R5', R6', R7' and R8', those bonded to adjacent carbon atoms are optionally bonded to each other to form, together with the constituent carbon atoms of Ar4, a saturated or unsaturated ring, wherein the ring formed optionally contains one or more hetero atoms, A' is a hydrogen atom, a halogen atom, a hydroxy group, a cyano group, a nitro group, a carboxyl group, a $C_{1-6}$, alkyl group optionally having one or more substituents, a alkenyl group optionally having one or more substituents, a $C_{2-6}$ alkynyl group optionally having one or more substituents, a $C_{3-8}$ cyclic alkyl group which optionally contains one or more hetero atoms in the ring, an aryl group optionally having one or more substituents, a heteroaryl group optionally having one or more substituents, a $C_{1-6}$ alkyl group substituted by one or more aryl groups which optionally have one or more substituents, a $C_{1-6}$ alkyl group substituted by one or more heteroaryl groups which optionally have one or more substituents, a $C_{1-6}$ alkoxy group optionally having one or more substituents, a $C_{1-6}$, alkylthio group optionally having one or more substituents, a $C_{1-6}$, alkoxy group substituted by one or more aryl groups which optionally have one or more substituents, a $C_{1-6}$ alkylthio group substituted by one or more aryl groups which optionally have one or more substituents, a $C_{1-6}$ alkoxy group substituted by one or more heteroaryl groups which optionally have one or more substituents, a $C_{1-6}$ alkylthio group substituted by one or more heteroaryl groups which optionally have one or more substituents, a $C_{3-8}$ cyclic alkyloxy group which optionally contains one or more hetero atoms in the ring, an aryloxy group optionally having one or more substituents, a heteroaryloxy group optionally having one or more substituents, an amino group, an amino group monosubstituted by a $C_{1-6}$ alkyl group, an amino group disubstituted by $C_{1-6}$, alkyl groups, a $C_{1-6}$ alkoxy-carbonyl group, a carbamoyl group, a carbamoyl group monosubstituted by a $C_{1-6}$ alkyl group, a carbamoyl group disubstituted by $C_{1-6}$ alkyl groups, a sulfamoyl group, a sulfamoyl group monosubstituted by a $C_{1-6}$ alkyl group, a sulfamoyl group disubstituted by $C_{1-6}$ alkyl groups, a $C_{1-6}$ alkanoyl group, a aroyl group optionally having one or more substituents, a $C_{1-6}$, alkyl-sulfonylamino group, an arylsulfonylamino group optionally having one or more substituents, a heteroarylsulfonylamino group optionally having one or more substituents, a $C_{1-6}$ acylamino group, a $C_{1-6}$ alkylsulfonyl group, a $C_{1-6}$ alkylsulfinyl group, or a group represented by the formula (II):

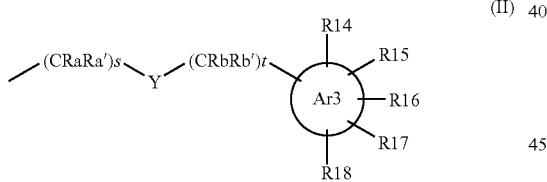

(II)

wherein
Ar3 is an aryl group, a heteroaryl group, or a nonaromatic heterocyclic group,
Y is —O—, —CH$_2$—, —NR19-, —S—, —S(O)—, —SO$_2$—, —NR19SO$_2$—, —SO$_2$NR19-, —C(O)NR19-, —NR19C(O)—, —NR19C(O)O— or —OC(O)NR19-,
Ra, Ra', Rb and Rb' are each independently a hydrogen atom or a $C_{1-6}$ alkyl group,
s is an integer of 1 or 2,
t is an integer of 0-2,
R14-R18 are each independently a hydrogen atom, a halogen atom, a $C_{1-6}$ alkyl group, a $C_{2-6}$ alkenyl group, a $C_{2-6}$ alkynyl group, a $C_{1-3}$ perfluoroalkyl group, a hydroxyl group, a $C_{1-6}$ alkyhhio group, a $C_{1-6}$ alkylsulfinyl group, a $C_{1-6}$ alkylsulfonyl group, a $C_{1-6}$ alkoxy group, a $C_{1-3}$ perfluoroalkoxy group, a cyano group, a nitro group, a $C_{1-6}$, alkyl-carbonyl group, an amino group, an amino group monosubstituted by a $C_{1-6}$, alkyl group, an amino group disubstituted by $C_{1-6}$ alkyl groups, a $C_{1-6}$, alkylsulfonylamino group, a formylamino group, a $C_{1-6}$ alkyl-carbonylamino group, a $C_{2-6}$ alkenyl-carbonylamino group, a $C_{7-12}$ aryl-carbonylamino group, a $C_{1-6}$ alkyl group substituted by one or more hydroxy groups, a carboxyl group, a $C_{1-6}$ alkoxy group substituted by one or more amino groups, a $C_{1-6}$ alkoxy group substituted by one or more hydroxy groups, a $C_{3-8}$ cycloalkyl group, a nonaromatic heterocyclic group, a carbamoyl group monosubstituted by a $C_{1-6}$ alkyl group, a carbamoyl group disubstituted by $C_{1-6}$ alkyl groups, a $C_{1-6}$ alkoxy-carbonyl group, a $C_{1-6}$-, alkyl group substituted by one or more amino groups, a $C_{1-6}$ alkyl group substituted by one or more amino groups which are monosubstituted by a $C_{1-6}$ alkyl group, or a $C_{1-6}$ alkyl group substituted by one or more amino groups which are disubstituted by $C_{1-6}$ alkyl groups, and R19 is hydrogen atom or a $C_{1-6}$ alkyl group, and Rc, Rd, Re, Re', Rf and Rf' are each independently a hydrogen atom or a $C_{1-6}$ alkyl group, provided that:

(1) when at least one of V1, V2, V3, and V4 is a nitrogen atom, then at least one of R1', R2', R3', and A' is a group other than a hydrogen atom, and (2) the following compounds (X-5) and (X-7) are excluded:

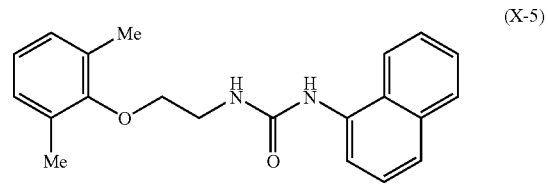

(X-5)

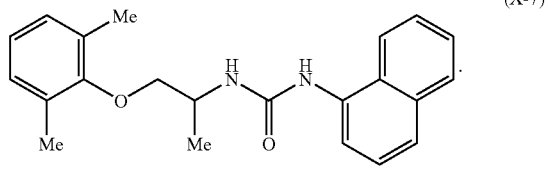

(X-7)

8. The ether compound of claim 6, having formula (III), wherein
m is 1, and
V5 and V6 are each NH,
a pharmaceutically acceptable salt thereof, or a hydrate thereof.

9. The ether compound of claim 8, having formula (III), wherein
X' is an oxygen atom,
a pharmaceutically acceptable salt thereof, or a hydrate thereof.

10. The ether compound of claim 8, having formula (III), wherein
VI is CR9',
V2 is a nitrogen atom or N→O,
V3 is CR11', and
V4 is CR12',
a pharmaceutically acceptable salt thereof or a hydrate thereof.

11. The ether compound of claim 8, having formula (III), wherein
V1 is CR9',
V2 is CR10',
V3 is C—OH, and V4 is CR12',
a pharmaceutically acceptable salt thereof, or a hydrate thereof.

12. The ether compound of claim 8, having formula (III), wherein
A' is a hydrogen atom or a $C_{1-6}$, alkyl group optionally having one or more substituents, and
R1', R2', and R3' are each a hydrogen atom,
a pharmaceutically acceptable salt thereof, or a hydrate thereof.

13. The ether compound of claim 8, having formula (III), wherein
Ar4 is a phenyl group, a naphthyl group, a pyridyl group, a quinolyl group, an isoquinolyl group, or a pyrimidinyl group, and R4', R5', R6', R7', and R8' are each independently a hydrogen atom, a $C_{1-6}$ alkyl group, a halogen atom, a $C_{1-6}$ alkoxy group, a $C_{1-6}$ alkylthio group, a trifluoromethyl group, an aryl group, a cyano group, a nitro group, an amino group or an amino group mono- or di-substituted by $C_{1-6}$ alkyl group(s), or
of R4', R5', R6', R7', and R8', those bonded to adjacent carbon atoms are bonded to each other to form, together with the constituent carbon atoms of Ar4, an unsaturated ring which optionally contains one or more hetero atoms in the ring,
a pharmaceutically acceptable salt thereof, or a hydrate thereof.

14. The ether compound of claim 10, having formula (III), wherein
X' is an oxygen atom,
A' is a $C_{1-6}$ alkyl group optionally having one or more substituents, and
R1', R2', and R3' are each a hydrogen atom,
a pharmaceutically acceptable salt thereof, or a hydrate thereof.

15. The ether compound of claim 11, having formula (III), wherein
X' is an oxygen atom,
A' is a hydrogen atom or a $C_{1-6}$ alkyl group optionally having one or more substituents, and
R1', R2', and R3' are each a hydrogen atom,
a pharmaceutically acceptable salt thereof, or a hydrate thereof.

16. The ether compound of claim 10, having formula (III), wherein
X' is an oxygen atom,
Ar4 is a phenyl group, a naphthyl group, a pyridyl group, a quinolyl group, an isoquinolyl group, or a pyrimidinyl group, and
R4', R5', R6', R7', and R8' are each independently a hydrogen atom, a $C_{1-6}$ alkyl group, a halogen atom, a $C_{1-6}$ alkoxy group, a $C_{1-6}$ alkylthio group, a trifluoromethyl group, an aryl group, a cyano group, a nitro group, an amino group or an amino group mono- or di-substituted by $C_{1-6}$ alkyl group(s), or
of R4', R5', R6', R7', and R8', those bonded to adjacent carbon atoms are bonded to each other to form, together with the constituent carbon atoms of Ar4, an unsaturated ring which optionally contains one or more hetero atoms in the ring,
a pharmaceutically acceptable salt thereof, or a hydrate thereof.

17. The ether compound of claim 11, having formula (III), wherein
X' is an oxygen atom,
Ar4 is a phenyl group, a naphthyl group, a pyridyl group, a quinolyl group, an isoquinolyl group, or a pyrimidinyl group, and
R4', R5', R6', R7', and R8' are each independently a hydrogen atom, a $C_{1-6}$ alkyl group, a halogen atom, a $C_{1-6}$ alkoxy group, a $C_{1-6}$ alkylthio group, a trifluoromethyl group, an aryl group, a cyano group, a nitro group, an amino group or an amino group mono- or di-substituted by $C_{1-6}$ alkyl group(s), or
of R4', R5', R6', R7' and R8', those bonded to adjacent carbon atoms are bonded to each other to form, together with the constituent carbon atoms of Ar4, an unsaturated ring which optionally contains one or more hetero atoms in the ring,
a pharmaceutically acceptable salt thereof, or a hydrate thereof.

18. The ether compound of claim 9, having formula (III), wherein
V1 is CH,
V2 is a nitrogen atom or N→O,
V3 is CH,
V4 is CH,
A' is a $C_{1-6}$ alkyl group optionally having one or more substituents, and
R1', R2', and R3' are each a hydrogen atom,
a pharmaceutically acceptable salt thereof, or a hydrate thereof.

19. The ether compound of claim 9, having formula (III), wherein
V1 is CH,
V2 is CH,
V3 is C—OH,
V4 is CH,
A' is a hydrogen atom, or a $C_{1-6}$ alkyl group optionally having one or more substituents, and
R1', R2', and R3' are each a hydrogen atom,
a pharmaceutically acceptable salt thereof, or a hydrate thereof.

20. The ether compound of claim 9, having formula (III), wherein
Ar4 is a phenyl group,
R4', R5', R6', R7', and R8' are each independently a hydrogen atom, a $C_{1-6}$ alkyl group, or a halogen atom, or
of R4', R5', R6', R7' and R8', those bonded to adjacent carbon atoms are bonded to each other to form, together with Ar4, a tetrahydronaphthalene ring or an indan ring,
V1 is CH,
V2 is a nitrogen atom or N→O,
V3 is CH,
V4 is CH,
A' is a $C_{1-6}$ alkyl group, and
R1', R2', and R3' are each a hydrogen atom,
a pharmaceutically acceptable salt thereof, or a hydrate thereof.

21. The ether compound of claim 9, having formula (III), wherein
Ar4 is a phenyl group,
R4', R5', R6', R7', and R8' are each independently a hydrogen atom, a $C_{1-6}$ alkyl group, or a halogen atom, or
of R4', R5', R6', R7', and R8', those bonded to adjacent carbon atoms are bonded to each other to form, together with Ar4, a tetrahydronaphthalene ring or an indan ring,
V1 is CH,
V2 is CH, V3 is C—OH,
V4 is CH,
A' is a hydrogen atom or a $C_{1-6}$ alkyl group, and
R1', R2', and R3' are each a hydrogen atom,
a pharmaceutically acceptable salt thereof, or a hydrate thereof.

22. The ether compound of claim 9, which is represented by the formula

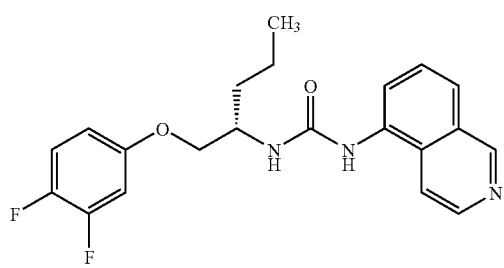

or a pharmaceutically acceptable salt thereof, or a hydrate thereof.

23. The ether compound of claim 9, which is represented by the formula

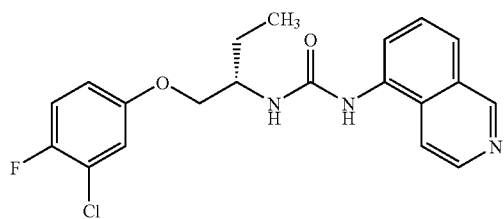

or a pharmaceutically acceptable salt thereof, or a hydrate thereof.

24. The ether compound of claim 9, which is represented by the formula

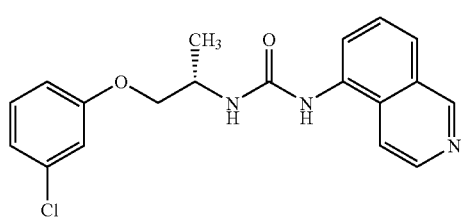

or a pharmaceutically acceptable salt thereof, or a hydrate thereof.

25. The ether compound of claim 9, which is represented by the formula

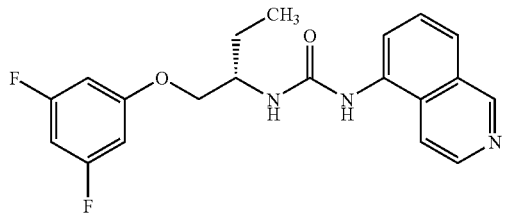

or a pharmaceutically acceptable salt thereof or a hydrate thereof.

26. The ether compound of claim 9, which is represented by the formula

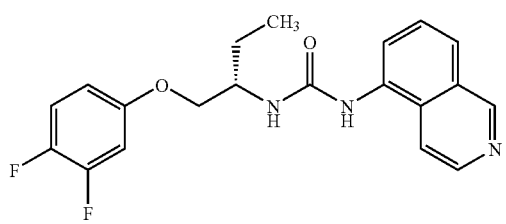

or a pharmaceutically acceptable salt thereof, or a hydrate thereof.

27. The ether compound of claim 9, which is represented by the formula

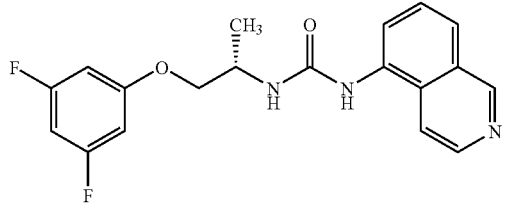

or a pharmaceutically acceptable salt thereof, or a hydrate thereof.

28. The ether compound of claim 9, which is represented by the formula

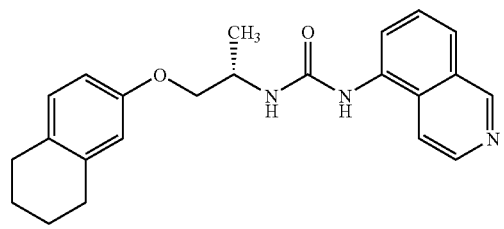

or a pharmaceutically acceptable salt thereof, or a hydrate thereof.

29. The ether compound of claim 9, which is represented by the formula

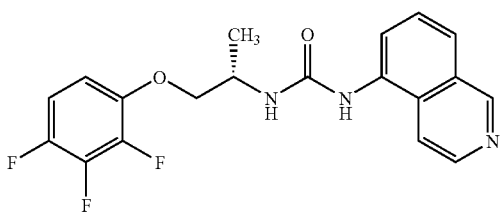

or a pharmaceutically acceptable salt thereof, or a hydrate thereof.

30. A pharmaceutical composition, comprising an ether compound of claim 1, a pharmaceutically acceptable salt thereof, or a hydrate thereof, and a pharmaceutically acceptable carrier.

31. A method of treating inflammation or pain, comprising administering an effective amount of a compound according to claim 1 to a subject in need thereof.

32. A method of treating inflammatory bowel disease, comprising administering an effective amount of a compound according to claim 1 to a subject in need thereof.

33. A method of treating pollakiuria and/or incontinentia, comprising administering an effective amount of a compound according to claim 1 to a subject in need thereof.

34. A method of treating asthma, comprising administering an effective amount of a compound according to claim 1 to a subject in need thereof.

35. A package, comprising a pharmaceutical composition comprising an ether compound of claim 1, a pharmaceutically acceptable salt thereof, or a hydrate thereof, and a written matter describing a use of said pharmaceutical composition.

36. A pharmaceutical composition comprising an ether compound of claim 6, a pharmaceutically acceptable salt thereof, or a hydrate thereof, and a pharmaceutically acceptable carrier.

37. A method of treating inflammation or pain, comprising administering an effective amount of a compound according to claim 6 to a subject in need thereof.

38. A method of treating inflammatory bowel disease, comprising administering an effective amount of a compound according to claim 6 to a subject in need thereof.

39. A method of treating pollakiuria and/or incontinentia, comprising administering an effective amount of a compound according to claim 6 to a subject in need thereof.

40. A method of treating asthma, comprising administering an effective amount of a compound according to claim 6 to a subject in need thereof.

41. A package comprising a pharmaceutical composition comprising an ether compound of claim 6, a pharmaceutically acceptable salt thereof, or a hydrate thereof, and a written matter describing a use of said pharmaceutical composition.

* * * * *

UNITED STATES PATENT AND TRADEMARK OFFICE
CERTIFICATE OF CORRECTION

PATENT NO. : 7,728,005 B2
APPLICATION NO. : 11/402958
DATED : June 1, 2010
INVENTOR(S) : Tatsuya Okuzumi et al.

It is certified that error appears in the above-identified patent and that said Letters Patent is hereby corrected as shown below:

Column 1, Line 7:
"PCTIJP04/15556" should read --PCT/JP04/15556--.

Column 87, Line 57:
"group, a alkylthio group," should read --group, a $C_{1-6}$ alkylthio group,--.

Column 88, Line 15:
", or a alkoxy group" should read --, or a $C_{1-6}$ alkoxy group--;

Lines 19-20:
", a alkyl group" should read --, a $C_{1-6}$ alkyl group--;

Line 42:
"–NR19C(O)O1—or" should read -- —NR19C(O)O—or--;

Line 61:
", a $C_1$-$C_6$ alkoxy group" should read --, a $C_{1-6}$ alkoxy group--.

Column 91, Line 38:
"a $C_{1-6}$, alkoxy group" should read --a $C_{1-6}$ alkoxy group--.

Column 93, Line 19:
"—NR 19C(O)—" should read -- —NR19C(O)— --;

Line 44:
", by a $C_{1-6}$, alkyl group" should read --, by a $C_{1-6}$ alkyl group--.

Column 94, Lines 16-17:
", a $C_{1-6}$, alkyl-carbonyl group" should read --, a $C_{1-6}$ alkyl-carbonyl group--;

Signed and Sealed this

Thirtieth Day of November, 2010

David J. Kappos
*Director of the United States Patent and Trademark Office*

Line 22:
", a alkoxy group" should read --, a $C_{1-6}$ alkoxy group--.

Column 95, Line 16:
", a alkynyl group" should read --, a $C_{2-6}$ alkynyl group--;

Line 23:
", a $C_{1-6}$, alkyl group" should read --, a $C_{1-6}$ alkyl group--;

Line 25:
", a $C_{1-6}$, alkoxy group" should read --, a $C_{1-6}$ alkoxy group--;

Lines 29-30:
", a $C_{1-6}$, alkylthio group" should read --, a $C_{1-6}$ alkylthio group--;

Lines 31-32:
", a $C_{1-6}$, alkoxy group" should read --, a $C_{1-6}$ alkoxy group--;

Line 46:
", by a $C_{1-6}$, alkyl group" should read --, by a $C_{1-6}$ alkyl group--;

Lines 47-48:
", a $C_{1-6}$, alkanoyl group" should read --, a $C_{1-6}$ alkanoyl group--;

Line 53:
", a $C_{1-6}$, alkyl-carbonylamino" should read --, a $C_{1-6}$ alkyl-carbonylamino--;

Line 55:
", a $C_{1-6}$, perfluoroalkyl-carbonylamino" should read --, a $C_{1-6}$ perfluoroalkyl-carbonylamino--;

Line 56:
", perfluoroalkyl-carbonylamino" should read --, a $C_{2-6}$ perfluoroalkyl-carbonylamino--;

Lines 66-67:
", a alkenyl group" should read --, a $C_{2-6}$ alkenyl group--.

Column 96, Lines 31-32:
", by $C_{1-6}$, alkyl group" should read --, by $C_{1-6}$ alkyl group--;

Lines 39-40:
", a $C_{1-6}$, aryl-carbonylamino" should read --, a $C_{6-12}$ aryl-carbonylamino--;

Lines 40-41:
", a alkylsulfinyl group" should read --, a $C_{1-6}$ alkylsulfinyl group--.

Column 97, Line 23:
", a $C_{1-6}$, alkyl group" should read --, or a $C_{1-6}$ alkyl group--.

Column 98, Line 11:
"R2' or R3' maybe the same" should read --R2' or R3' may be the same--;

Line 22:
", a C$_{1-6}$, alkyl group" should read --, a C$_{1-6}$ alkyl group--;

Line 24:
", a C$_{1-6}$, alkyl group" should read --, a C$_{1-6}$ alkyl group--;

Line 55:
", a C$_{1-6}$, alkylsulfinyl group" should read --, a C$_{1-6}$ alkylsulfinyl group--;

Lines 63-64:
", a C$_{1-6}$, alkyl group" should read --, a C$_{1-6}$ alkyl group--;

Line 65:
", a alkenyl group" should read --, a C$_{2-6}$ alkenyl group--.

Column 99, Line 9:
", a C$_{1-6}$, alkylthio group" should read --, a C$_{1-6}$ alkylthio group--;

Line 10:
", a C$_{1-6}$, alkoxy group" should read --, a C$_{1-6}$ alkoxy group--;

Line 24:
", a C$_{1-6}$, alkyl group" should read --, a C$_{1-6}$ alkyl group--;

Line 30:
", a aroyl group" should read --, a C$_{7-12}$ aroyl group--;

Lines 31-32:
", a C$_{1-6}$, alkylsulfonylamino group" should read --, a C$_{1-6}$ alkylsulfonylamino group--;

Line 66:
", a C$_{1-6}$, alkyl-carbonyl group" should read --, a C$_{1-6}$ alkyl-carbonyl group--;

Line 67:
", by a C$_{1-6}$, alkyl group" should read --, by a C$_{1-6}$ alkyl group--.

Column 100, Lines 1-2:
", a C$_{1-6}$, alkylsulfonylamino group" should read --, a C$_{1-6}$ alkylsulfonylamino group--;

Line 12:
", a C$_{1-6}$, alkyl group" should read --, a C$_{1-6}$ alkyl group--;

Line 63:
"salt thereof or a hydrate" should read --salt thereof, or a hydrate--.

CERTIFICATE OF CORRECTION (continued)
U.S. Pat. No. 7,728,005 B2

<u>Column 101, Line:</u>
"or a $C_{1-6}$, alkyl group" should read --or a $C_{1-6}$ alkyl group--.